United States Patent
Betageri et al.

(10) Patent No.: US 8,546,442 B2
(45) Date of Patent: Oct. 1, 2013

(54) PYRAZOLOPIPERIDINE COMPOUNDS AS CCR1 RECEPTOR ANTAGONISTS

(75) Inventors: Rajashekhar Betageri, Bethel, CT (US); Brian Nicholas Cook, Danbury, CT (US); Darren DiSalvo, New Milford, CT (US); Christian Harcken, New Milford, CT (US); Daniel Kuzmich, Danbury, CT (US); Pingrong Liu, Southbury, CT (US); John Lord, Poughkeepsie, NY (US); Can Mao, New Milford, CT (US); Hossein Razavi, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 96 days.

(21) Appl. No.: 13/328,199

(22) Filed: Dec. 16, 2011

(65) Prior Publication Data

US 2012/0322790 A1    Dec. 20, 2012

Related U.S. Application Data

(60) Provisional application No. 61/426,550, filed on Dec. 23, 2010.

(51) Int. Cl.
| | | |
|---|---|---|
| *A01N 43/56* | (2006.01) | |
| *A01N 43/42* | (2006.01) | |
| *A61K 31/415* | (2006.01) | |
| *A61K 31/44* | (2006.01) | |
| *C07D 231/54* | (2006.01) | |
| *C07D 487/02* | (2006.01) | |

(52) U.S. Cl.
USPC .................. 514/406; 514/303; 548/360.5

(58) Field of Classification Search
None
See application file for complete search history.

(56) References Cited

U.S. PATENT DOCUMENTS

| | | | |
|---|---|---|---|
| 4,999,363 A | 3/1991 | Oshima et al. | |
| 5,118,701 A | 6/1992 | Oshima et al. | |
| 5,242,931 A | 9/1993 | Oshima et al. | |
| 5,302,596 A | 4/1994 | Oshima et al. | |
| 5,534,481 A | 7/1996 | Suzuki et al. | |
| 5,612,360 A | 3/1997 | Boyd et al. | |
| 5,616,537 A | 4/1997 | Yokota et al. | |
| 5,670,452 A | 9/1997 | Suzuki et al. | |
| 5,760,028 A | 6/1998 | Jadhav et al. | |
| 5,763,616 A | 6/1998 | Suzuki et al. | |
| 5,770,544 A | 6/1998 | Yokota et al. | |
| 5,973,156 A | 10/1999 | Chambers et al. | |
| 6,025,374 A | 2/2000 | Castro Pineiro et al. | |
| 6,107,321 A | 8/2000 | Madin | |
| 6,211,219 B1 | 4/2001 | MacLeod et al. | |
| 6,326,382 B1 | 12/2001 | Villalobos et al. | |
| 6,331,640 B1 | 12/2001 | Fotouhi et al. | |
| 6,498,255 B2 | 12/2002 | Villalobos et al. | |
| 6,716,978 B2 | 4/2004 | Marfat | |
| 6,784,182 B2 | 8/2004 | Liebeschuetz et al. | |
| 6,803,384 B2 | 10/2004 | Fotouhi et al. | |
| 6,855,715 B1 | 2/2005 | Liebeschuetz et al. | |
| 6,878,725 B2 | 4/2005 | Liebeschuetz et al. | |
| 6,900,196 B2 | 5/2005 | Liebeschuetz et al. | |
| 6,936,611 B2 | 8/2005 | Liebeschuetz et al. | |
| 7,049,297 B2 | 5/2006 | Zhang et al. | |
| 7,053,078 B2 | 5/2006 | Liebeschuetz et al. | |
| 7,129,264 B2 | 10/2006 | Smallheer et al. | |
| 7,223,782 B2 | 5/2007 | Atkinson et al. | |
| 7,429,609 B2 | 9/2008 | Ohi et al. | |
| 7,879,873 B2 | 2/2011 | Cook et al. | |
| 8,063,065 B2 | 11/2011 | Cook et al. | |
| 2002/0037860 A1 | 3/2002 | D'Andrea et al. | |
| 2002/0052373 A1 | 5/2002 | Zorn et al. | |
| 2004/0127536 A1 | 7/2004 | Bhagwat et al. | |
| 2005/0009876 A1 | 1/2005 | Bhagwat et al. | |
| 2005/0020564 A1 | 1/2005 | Atkinson et al. | |
| 2005/0108582 A1 | 5/2005 | Fung | |
| 2005/0208582 A1 | 9/2005 | Ohi et al. | |
| 2005/0261339 A1 | 11/2005 | Ohi et al. | |

(Continued)

FOREIGN PATENT DOCUMENTS

| | | |
|---|---|---|
| EP | 345747 A2 | 12/1989 |
| EP | 1201268 A2 | 5/2002 |

(Continued)

OTHER PUBLICATIONS

Alzheimer's Disease. Retrieved online Dec. 15, 2010. http:/www.cnn.com/HEALTH/mentalhealt/alzheimers.

(Continued)

*Primary Examiner* — Jeffrey S. Lundgren
*Assistant Examiner* — Michael Schmitt
(74) *Attorney, Agent, or Firm* — Michael P. Morris; Anthony P. Bottino

(57) ABSTRACT

Disclosed are compounds of the formula (I), useful for treating a variety of diseases and disorders that are mediated or sustained through the activity of CCR1 including autoimmune diseases, such as rheumatoid arthritis and multiple sclerosis.

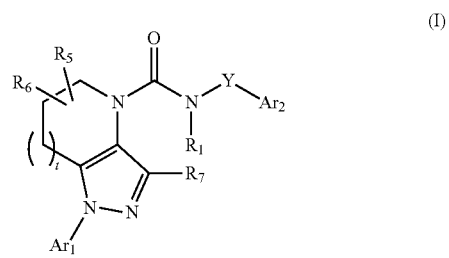

(I)

Also disclosed are methods of making and methods of using same.

17 Claims, No Drawings

(56) References Cited

U.S. PATENT DOCUMENTS

| | | |
|---|---|---|
| 2006/0252781 A1 | 11/2006 | Basarab et al. |
| 2006/0281739 A1 | 12/2006 | Gadek et al. |
| 2007/0004761 A1 | 1/2007 | Basarab et al. |
| 2008/0262040 A1 | 10/2008 | Callahan et al. |
| 2009/0054397 A1 | 2/2009 | Ohi et al. |
| 2010/0093724 A1 | 4/2010 | Cook et al. |
| 2011/0034512 A1 | 2/2011 | Disalvo et al. |
| 2011/0086846 A1 | 4/2011 | Cook et al. |
| 2011/0137042 A1 | 6/2011 | Razavi et al. |
| 2011/0230521 A1 | 9/2011 | Cook et al. |
| 2011/0294808 A1 | 12/2011 | Kuzmich et al. |

FOREIGN PATENT DOCUMENTS

| | | |
|---|---|---|
| JP | 10001478 A | 1/1998 |
| WO | 9217475 A1 | 10/1992 |
| WO | 9401415 A1 | 1/1994 |
| WO | 9500509 | 5/1995 |
| WO | 9617842 A1 | 6/1996 |
| WO | 9711945 A1 | 4/1997 |
| WO | 9719073 A1 | 5/1997 |
| WO | 9723480 A1 | 7/1997 |
| WO | 9803504 A1 | 1/1998 |
| WO | 9923076 A1 | 5/1999 |
| WO | 0021920 A1 | 4/2000 |
| WO | 0076970 A2 | 12/2000 |
| WO | 0076971 A2 | 12/2000 |
| WO | 0100656 A2 | 1/2001 |
| WO | 0210137 A2 | 2/2002 |
| WO | 03087085 A1 | 10/2003 |
| WO | 03101968 A1 | 12/2003 |
| WO | 03105853 A1 | 12/2003 |
| WO | 2004043924 A1 | 5/2004 |
| WO | 2004056831 A1 | 7/2004 |
| WO | 2004094372 A2 | 11/2004 |
| WO | 2005016929 A1 | 2/2005 |
| WO | 2006091496 A2 | 8/2006 |
| WO | 2006125119 A1 | 11/2006 |
| WO | 2007002293 A2 | 1/2007 |
| WO | 2007028083 A2 | 3/2007 |
| WO | 2007102883 A2 | 9/2007 |
| WO | 2008011131 | 1/2008 |
| WO | 2009024585 A2 | 2/2009 |
| WO | 2009037570 A2 | 3/2009 |
| WO | 2009134666 A1 | 11/2009 |
| WO | 2009137338 A1 | 11/2009 |
| WO | 2010036632 A1 | 4/2010 |
| WO | 2011049917 A1 | 4/2011 |
| WO | 2011056440 A1 | 5/2011 |
| WO | 2011071730 A1 | 6/2011 |

OTHER PUBLICATIONS

CAPLUS: 1990:478384, Bruneau, 1990.
CAPLUS: 2008:94643, Kitamura, 2008.
CAPLUS: 2009:583109, Doherty, 2009.
Carter, P.H. et al., "N-aryl pyrazoles, indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.
Cheng, J-F, et al., "CCR1 Antagonists". Molecular Diversity, Kluwer Academic Publishers, vol. 12, No. 1, Jun. 17, 2008, p. 17-23.
Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.
Gerard, C. et al., "Chemokines and disease". 2001 Nature Publishing Group, Chemokine Reviews, Nature Immunology, vol. 2, No. 2, Feb. 2001, p. 108-115.
Haringman, J.J. et al., "Chemokine blockade and chronic inflammatory disease: proof of concept in patients with rheumatoid arthritis". Ann Rheum Dis, 2003, 62, p. 715-721.
Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.
Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.
Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.
Plater-Zyberk, C. et al., "Effect of a CC chemokine receptor antagonist on collagen induced arthritis in DBA/1 mice". Immunology Letters, 57, 1997, p. 117-120.
Revesz, L. et al., "Novel CCR1 antagonists with oral activity in the mouse collagen induced arthritis". Bioorganice and Medicinal Chemistry Letters, 2005, p. 1-5.
Trebst, C. et al., "CCR1+/CCR5+ Mononuclear Phagocytes Accumulate in the Central Nervous System on Patients with Multiple Sclerosis." American Journal of Pathology, vol. 159, No. 4, Nov. 2001, p. 1701-1710.
Volin, M.V. et al., "RANTES Expression and Contribution to Monocyte Chemotaxix in Arthritis". Clinical Immunology and Immunopathology, vol. 89, No. 1, Oct. 1998, Article II984590, p. 44-53.

PYRAZOLOPIPERIDINE COMPOUNDS AS CCR1 RECEPTOR ANTAGONISTS

APPLICATION DATA

This application claims benefit to U.S. provisional application Ser. No. 61/426,550 filed Dec. 23, 2010.

FIELD OF THE INVENTION

This invention relates to pyrazolopiperidines that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) *American J of Pathology* 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) *Nature Immunology*). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) *Clin. Immunol. Immunopathology*; Koch et al. (1994) *J. Clin. Investigation*; Conlon et al. (1995) *Eur. J. Immunology*). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) *Eur. J. Immunology*). Furthermore, administration of small molecule antagonist of CCR1, with moderate affinity ($K_i$=120 nM) for rat CCR1, was shown to delay the onset and reduce the severity of EAE when administered intravenously (Liang et al. (2000) *J. Biol. Chemistry*). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) *J. Immunology*; Karpus and Kennedy (1997) *J. Leukocyte Biology*). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) *Immunology Letters*). Another publication described potent antagonists of murine CCR1 that reduced severity (58%) in LPS-accelerated collagen-induced arthritis (CIA), when administered orally (*Biorg. Med. Chem. Lett*. 2005, 15, 5160-5164). Published results from a Phase Ib clinical trial with an oral CCR1 antagonist demonstrated a trend toward clinical improvement in the absence of adverse side effects (Haringman et al. (2003) *Ann. Rheum. Dis.*). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provides a compound of the formula (I)

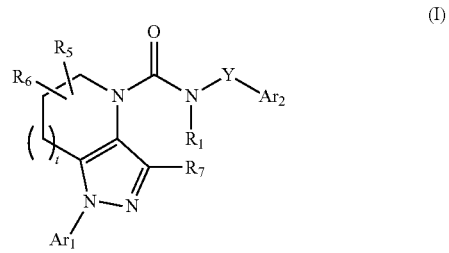

wherein t is 0, 1 or 2 such that the nitrogen containing ring in the formula (I) can be 5, 6 or 7 membered ring fused to the pyrazole ring to form a bicyclic ring system;

$Ar_1$ is carbocycle, heteroaryl or heterocyclyl each optionally substituted by one to three $R_a$;

$Ar_2$ is carbocycle, heteroaryl or heterocyclyl, each optionally substituted by one to three $R_b$;

Y is a bond or $(CR_2R_3)_m$;

$R_1$ is hydrogen, $C_{1-6}$ alkyl or $C_{1-6}$ alkoxy$C_{1-6}$ alkyl;

$R_2$, $R_3$ are each independently hydrogen, $C_{1-6}$ alkyl or $C_{2-6}$ alkenyl, wherein the $C_{1-6}$ alkyl or $C_{2-6}$ alkenyl is optionally partially or fully halogenated or substituted with one to three groups independently selected from hydroxyl, —$CO_2C_{1-6}$ alkyl, —$C(O)N(R_e)(R_f)$, —$N(R_e)(R_f)$, and heterocyclyl;

or $R_2$, $R_3$ can form a carbocycle, or heterocycle each optionally substituted by one to three $R_g$ provided that $R_2$ and $R_3$ are on the same carbon atom, $R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4$—$S(O)_m$—NH—, $R_4$—NH—$S(O)_m$—, aryl or carboxyl;

$R_b$ is hydroxyl, carboxyl, halogen, —$(CH_2)_n$—CN, —$(CH_2)_n$—$CO_2C_{1-6}$alkyl, nitro, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —$(CH_2)_n$—$NR_cR_d$, $R_4$—$S(O)_m(CH_2)_{0-1}$—, $R_4$—$S(O)_m$—$NR_e$—, $R_4$—$NR_e$—$S(O)_m(CH_2)_{0-1}$—, —$NR_f$—C(O)—$R_e$, —$(CH_2)_x$—C(O)—$(CH_2)_n$—$NR_cR_d$, heterocyclyl, aryl or heteroaryl, each $R_b$ is optionally substituted with 1 to 3 halogen, $C_{1-6}$ alkyl, $C_{1-6}$ acyl, $C_{1-6}$ alkoxycarbonyl, $C_{1-6}$ alkyl-S(O)_m—, aryl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, $C_{1-6}$ alkyl$C_{1-6}$ alkoxy, $C_{1-6}$ alkyl sulfonyl, $C_{1-6}$ alkoxycarbonyl $C_{0-3}$alkyl or —$(CH_2)_n$—$NR_eR_f$;

each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono- or di-$C_{1-6}$alkylamino$C_{1-6}$alkyl, hydroxy$C_{1-6}$ alkyl or $C_{1-6}$ acyl;

$R_g$ is $C_{1-6}$ alkyl, wherein the $C_{1-6}$ alkyl is optionally partially or fully halogenated, $C_{2-6}$ alkenyl, carbocycle, $C_{1-6}$ alkoxy, hydroxy$C_{1-6}$ alkyl, cyano, halogen, hydroxyl, —$(CH_2)_n$—$CO_2C_{1-6}$ alkyl, —$(CH_2)_n$—$C(O)N(R_e)(R_f)$, —$(CH_2)_n$—$N(R_e)(R_f)$ or oxo;

$R_4$ is hydrogen, heterocyclyl or $C_{1-6}$ alkyl optionally substituted by $C_{1-4}$ alkoxy, hydroxyl, heterocyclyl, heteroaryl or aryl each ring is further optionally substituted with 1 to 3 $C_{1-6}$ alkyl, $C_{3-6}$cycloalkyl, $C_{1-6}$alkoxy, halogen, hydroxyl, oxo, carboxyl, —$C(O)NR_eR_f$, amino, mono- or di-$C_{1-6}$ alkylamino, $C_{1-6}$ alkoxycarbonyl or $C_{1-6}$ acylamino;

each n, x are independently 0-3;

each m is independently 0-2;

$R_5$ is covalently attached at the 5, 6 or 7 position and is hydrogen, $C_{1-6}$ alkyl, $C_{3-6}$cycloalkyl, heterocyclyl$(CH_2)_{0-1}$, mono- or di-$C_{1-6}$ alkylamino, mono- or di-$C_{1-6}$alkylamino$(CH_2)_{2-3}N(R_e)$—, $C_{1-6}$alkyl$CO_2$—, carboxyl, $N(R_e)(R_f)$—C(O)—, cyano, $R_4$—$S(O)_n$—, $R_4$—$NR_e$—$S(O)_m$—, aryl or heteroaryl each optionally substituted with $C_{1-6}$ alkyl, $C_{3-6}$cycloalkyl, $C_{1-6}$alkoxy, halogen, hydroxyl, oxo, carboxyl, —$C(O)NR_eR_f$, amino, mono- or di-$C_{1-6}$ alkylamino, $C_{1-6}$ alkoxycarbonyl or $C_{1-6}$ acylamino;

$R_6$ is covalently attached at the 5, 6 or 7 position and is hydrogen, $C_{1-6}$ alkyl, each optionally substituted with 1 to 3 $C_{1-6}$ alkyl, or halogen;

or $R_5$, $R_6$ can form a $C_{3-6}$ cycloalkyl ring provided that $R_5$ and $R_6$ are on the same carbon atom, $R_7$ is hydrogen or $C_{1-6}$ alkyl;

or a pharmaceutically acceptable salt thereof;

wherein each alkyl group defined in this embodiment can be optionally partially or fully halogenated.

In another embodiment of the invention there is provided a compound of the formula (I) according to any of the embodiments disclosed herein, and wherein $Ar_1$ is aryl substituted by one to three $R_a$;

$Ar_2$ is aryl or heteroaryl, each optionally substituted by one to three $R_b$;

Y is $(CR_2R_3)_m$;

$R_1$ is hydrogen;

each $R_e$, $R_f$ are independently hydrogen, $C_{1-6}$ alkyl or hydroxy$C_{1-6}$ alkyl;

$R_2$, $R_3$ are each independently hydrogen, $C_{1-6}$ alkyl or $C_{2-6}$ alkenyl, wherein the $C_{1-6}$ alkyl or $C_{2-6}$ alkenyl is optionally partially or fully halogenated, or $R_2$, $R_3$ can form a $C_{3-7}$ cycloalkyl ring provided that $R_2$, $R_3$ are attached to the same carbon atom, $R_5$ is hydrogen, $C_{1-6}$alkyl$CO_2$—, carboxyl, $N(R_e)(R_f)$—C(O)— or $C_{1-6}$ alkyl optionally partially or fully halogenated;

$R_6$ is hydrogen, $C_{1-6}$ alkyl;

$R_7$ is hydrogen.

In another embodiment of the invention there is provided a compound of the formula (I) according to any of the embodiments disclosed herein, and wherein $Ar_1$ is phenyl substituted by one to three $R_a$;

$Ar_2$ is phenyl or heteroaryl chosen from furanyl, pyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, quinolinyl, isoquinolinyl, quinazolinyl, indazolyl, indolyl, isoindolyl, benzofuranyl, benzopyranyl, pyrrolopyridinyl and benzodioxolyl;

each optionally substituted by one to three $R_b$.

In another embodiment of the invention there is provided a compound of the formula (I) according to any of the embodiments disclosed herein, and wherein $Ar_2$ is phenyl, benzyl, phenethyl or heteroaryl chosen from pyridinyl, pyrimidinyl, pyridazinyl and pyrazinyl;

each optionally substituted by one to three $R_b$.

In another embodiment of the invention there is provided a compound of the formula (I) according to any of the embodiments disclosed herein, and wherein $Ar_2$ is phenyl, benzyl, phenethyl or pyridinyl;

each optionally substituted by one to three $R_b$.

In another embodiment of the invention there is provided a compound of the formula (I) according to any of the embodiments disclosed herein, and wherein $R_b$ is halogen, $C_{1-5}$ alkyl optionally halogenated, $C_{1-5}$ alkoxy, hydroxyl, $R_4$—$S(O)_m$— or $R_4$—$NR_e$—$S(O)_m$—;

$R_4$ is morpholinyl, thiomorpholinyl, pyrrolidinyl, piperadinyl, piperazinyl, dioxalanyl, dioxanyl, tetrahydropyranyl, tetrahydrofuranyl or $C_{1-4}$ alkyl optionally substituted by $C_{1-4}$ alkoxy, morpholinyl, thiomorpholinyl, pyrrolidinyl, piperadinyl, piperazinyl, dioxalanyl, dioxanyl, tetrahydropyranyl or tetrahydrofuranyl;

$R_e$ is hydrogen or $C_{1-3}$ alkyl or hydroxy$C_{1-6}$ alkyl;

$R_2$, $R_3$ are each independently hydrogen or $C_{1-6}$ alkyl optionally partially or fully halogenated, or $R_2$, $R_3$ can form a $C_{3-6}$ cycloalkyl ring provided that $R_2$, $R_3$ are attached to the same carbon atom, In another embodiment of the invention there is provided a compound of the formula (I) according to any of the embodiments disclosed herein, and wherein $R_b$ is halogen, $C_{1-3}$ alkyl optionally halogenated, $C_{1-3}$ alkoxy, hydroxyl, $R_4$—$S(O)_m$— or $R_4$—$NR_e$—$S(O)_m$—;

$R_4$ is $C_{1-3}$ alkyl substituted by $C_{1-3}$ alkoxy, morpholinyl or tetrahydropyranyl;

$R_2$, $R_3$ are each independently hydrogen or $C_{1-6}$ alkyl optionally partially or fully halogenated, or $R_2$, $R_3$ can form a $C_{3-5}$ cycloalkyl ring provided that $R_2$, $R_3$ are attached to the same carbon atom.

In another embodiment of the invention there is provided a compound of the formula (I) according to any of the embodiments disclosed herein, and wherein $Ar_1$ is phenyl substituted by one to three halogen;

$Ar_2$ is phenyl or pyridinyl;

$R_b$ is —$OCH_3$, —$CH_3$, F, Cl, Br, —$CF_3$, hydroxyl, —$S(O)_2$—$CH_3$, —$S(O)_2$—NH—$CH_3$, —$S(O)_2$—$N(CH_3)_2$, —$S(O)_2$—NH—$(CH_2)_2$—$OCH_3$, —$S(O)_2$—NH—CH($CH_3$)—$CH_2OH$,

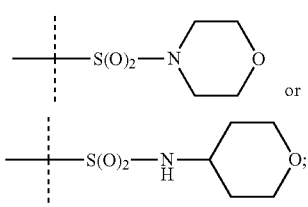

R₂, R₃ are each independently hydrogen, C₁₋₆ alkyl, or R₂, R₃ can form a cyclopropyl ring provided that R₂, R₃ are attached to the same carbon atom, R₅ is hydrogen, —CH₃, —CF₃, —C(O)₂CH₂CH₃, —C(O)NHCH₃ or —C(O)NH(CH)₂OH;

R₆ is hydrogen, —CH₃.

In another embodiment of the invention there is provided a compound of the formula (I) according to any of the embodiments disclosed herein, and wherein Ar₁ is

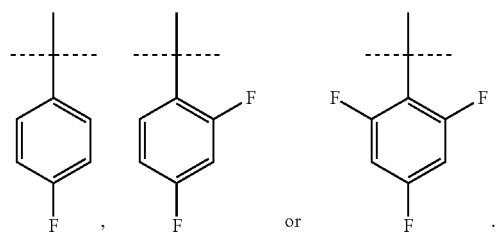

In another embodiment of the invention there is provided a compound of the formula (I) according to any of the embodiments disclosed herein, and wherein Ar₁ is

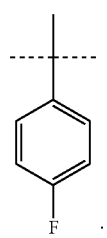

In another embodiment of the invention there is provided a compound of the formula (I) according to any of the embodiments disclosed herein, and wherein Ar₂ is

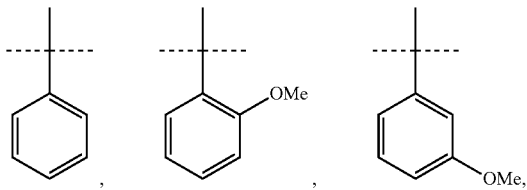

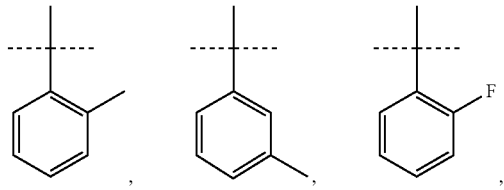

-continued

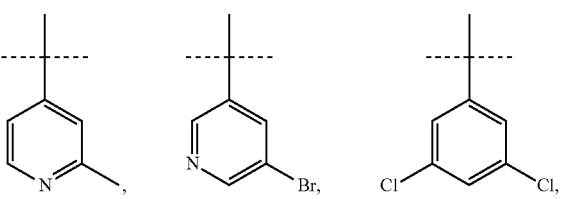

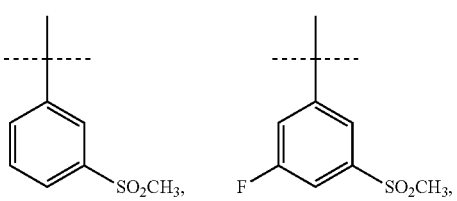

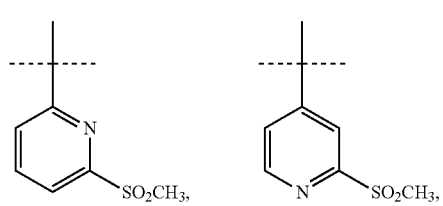

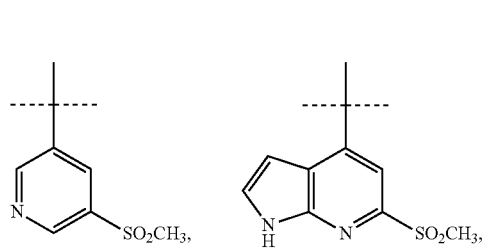

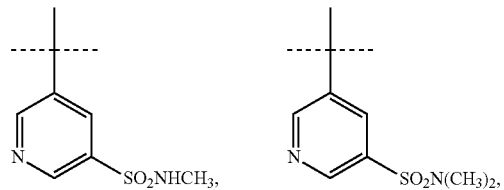

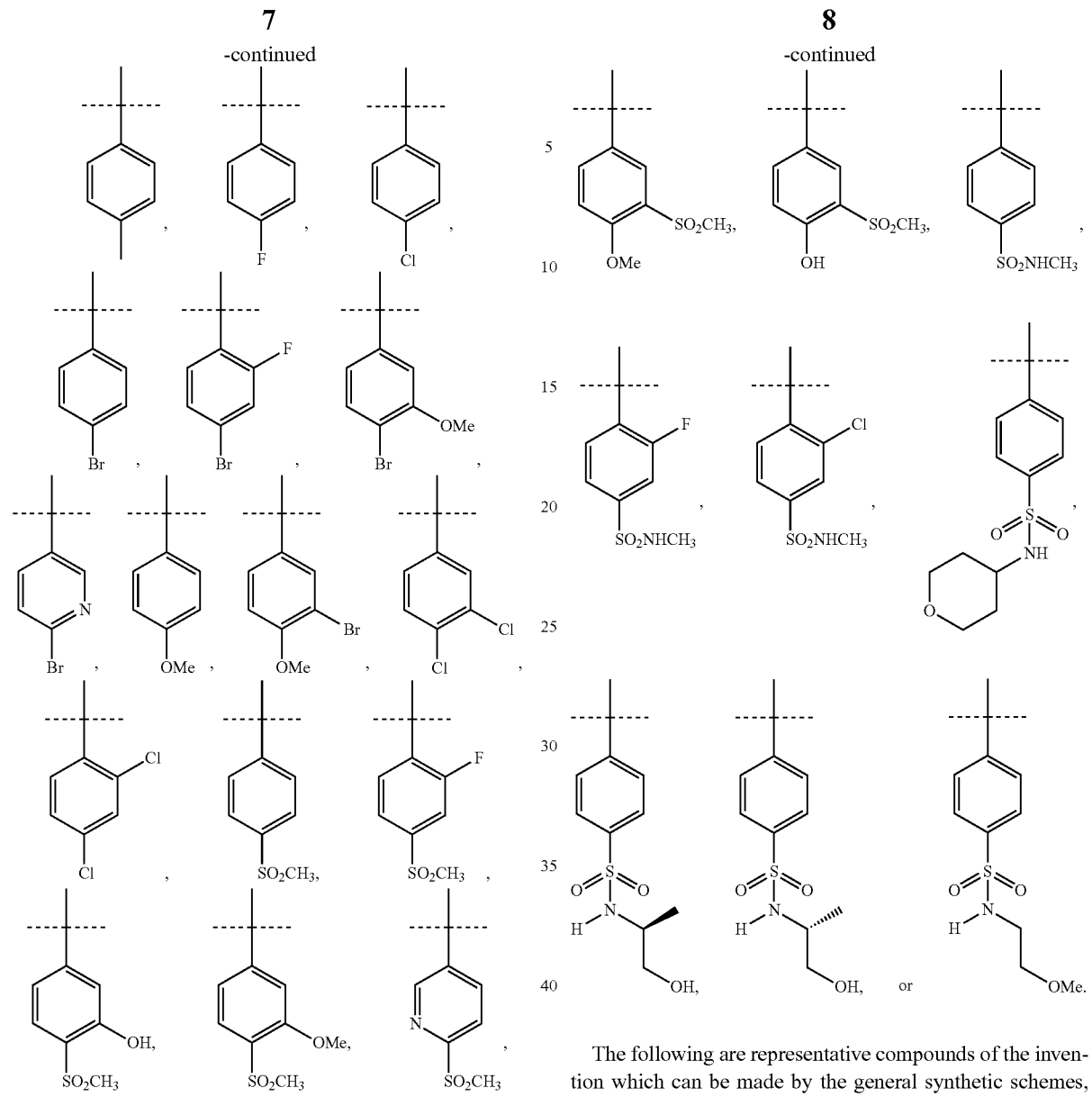
The following are representative compounds of the invention which can be made by the general synthetic schemes, examples, and known methods in the art.
TABLE I
| Example # | Structure | HPLC-MS Data [a] m/z [M + H]+ [b] | Retention time (min) |
|---|---|---|---|
| 1 | 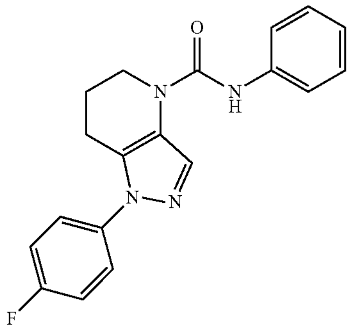 [SMILES: O=C(Nc1ccccc1)N1CCCc2c1cnn2-c1ccc(F)cc1] | 337.2 | 0.90 |

TABLE I-continued

| Example # | Structure | HPLC-MS Data [a] m/z [M + H]+ [b] | Retention time (min) |
|---|---|---|---|
| 2 | 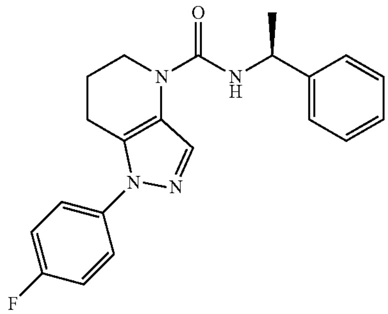 [SMILES: C[C@H](NC(=O)N1CCCc2c1cnn2-c1ccc(F)cc1)c1ccccc1] | 365.0 | 0.91 |
| 3 | 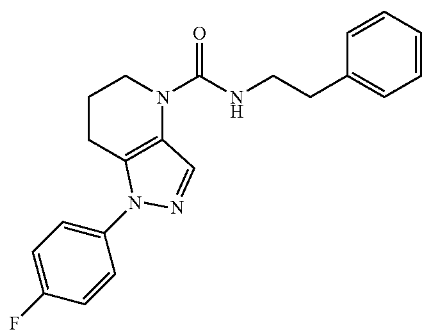 [SMILES: O=C(NCCc1ccccc1)N1CCCc2c1cnn2-c1ccc(F)cc1] | 365.1 | 0.98 |
| 4 | 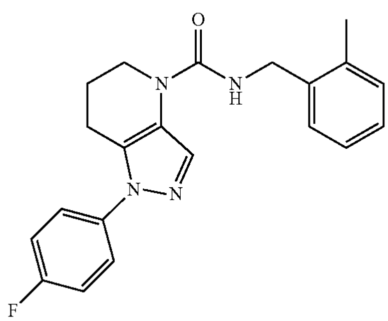 [SMILES: Cc1ccccc1CNC(=O)N1CCCc2c1cnn2-c1ccc(F)cc1] | 365.1 | 0.94 |
| 5 | 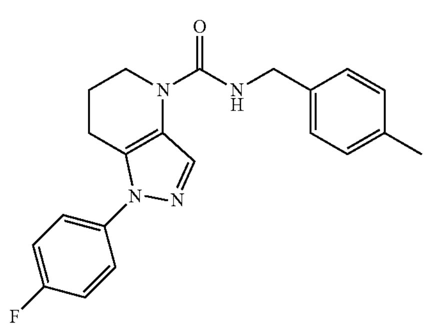 [SMILES: Cc1ccc(CNC(=O)N2CCCc3c2cnn3-c2ccc(F)cc2)cc1] | 364.9 | 0.91 |

TABLE I-continued
| Example # | Structure | m/z [M + H]+ [b] | Retention time (min) |
|---|---|---|---|
| 6 | 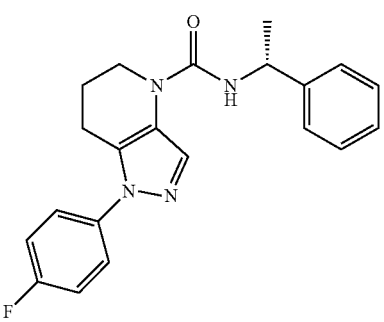 | 364.9 | 0.93 |
| 7 | 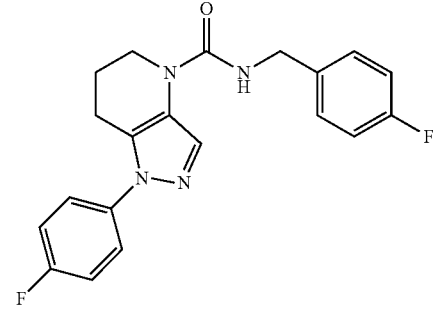 [SMILES: O=C(NCc1ccc(F)cc1)N1CCCc2c1cnn2-c1ccc(F)cc1] | 369.1 | 0.94 |
| 8 | 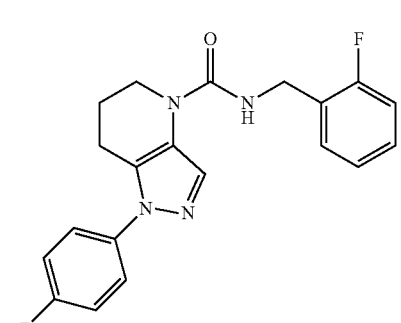 | 369.0 | 0.91 |
| 9 | 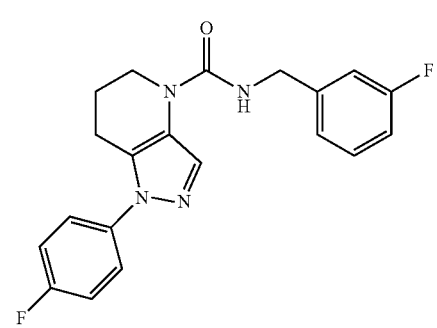 [SMILES: O=C(NCc1cccc(F)c1)N1CCCc2c1cnn2-c1ccc(F)cc1] | 369.1 | 1.05 |
HPLC-MS Data [a]

TABLE I-continued
| Example # | Structure | HPLC-MS Data [a] m/z [M + H]+ [b] | Retention time (min) |
|---|---|---|---|
| 10 | 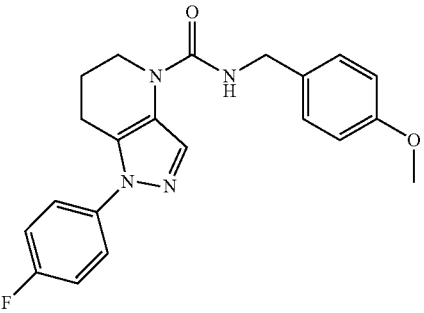 [SMILES: COc1ccc(CNC(=O)N2CCCc3c2cnn3-c2ccc(F)cc2)cc1] | 381.2 | 0.95 |
| 11 | 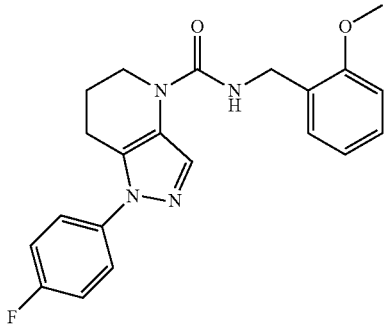 | 380.9 | 0.89 |
| 12 | 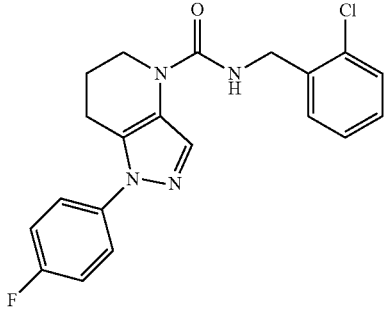 | 385.1 | 1.05 |
| 13 | 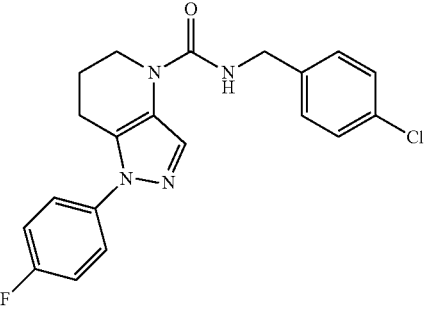 [SMILES: O=C(NCc1ccc(Cl)cc1)N1CCCc2c1cnn2-c1ccc(F)cc1] | 385.1 | 0.96 |

TABLE I-continued

| Example # | Structure | HPLC-MS Data m/z [M + H]+ [b] | Retention time (min) |
|---|---|---|---|
| 14 | 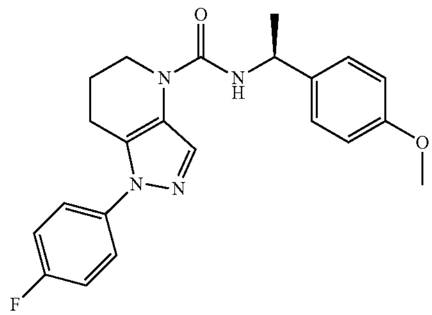 [SMILES: COc1ccc([C@H](C)NC(=O)N2CCCc3c2cnn3-c2ccc(F)cc2)cc1] | 395.0 | 0.93 |
| 15 | 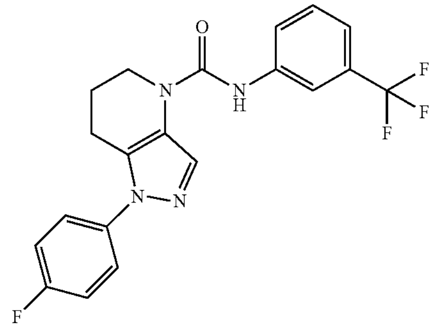 [SMILES: O=C(Nc1cccc(C(F)(F)F)c1)N1CCCc2c1cnn2-c1ccc(F)cc1] | 404.9 | 1.06 |
| 16 | 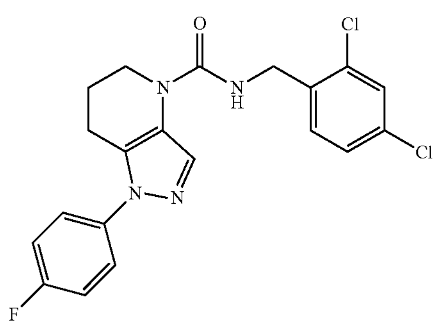 [SMILES: O=C(NCc1ccc(Cl)cc1Cl)N1CCCc2c1cnn2-c1ccc(F)cc1] | 419.1 | 0.97 |
| 17 | 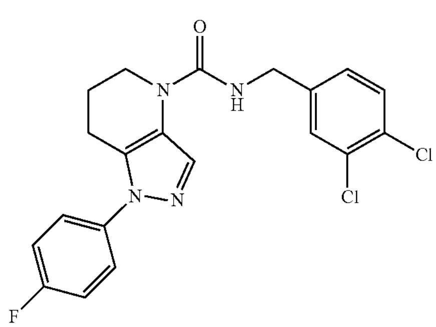 [SMILES: O=C(NCc1ccc(Cl)c(Cl)c1)N1CCCc2c1cnn2-c1ccc(F)cc1] | 419.1 | 1.04 |

TABLE I-continued

| Example # | Structure | HPLC-MS Data [a] m/z [M + H]+ [b] | Retention time (min) |
|---|---|---|---|
| 18 | 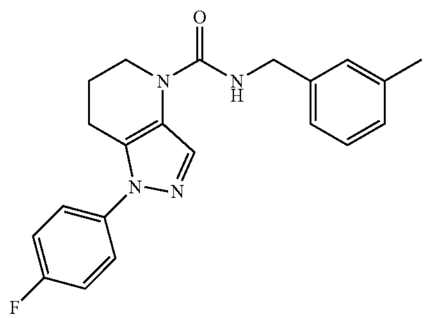 [SMILES: Cc1cccc(CNC(=O)N2CCCc3c2cnn3-c2ccc(F)cc2)c1] | 365.8 | 1.63 |
| 19 | 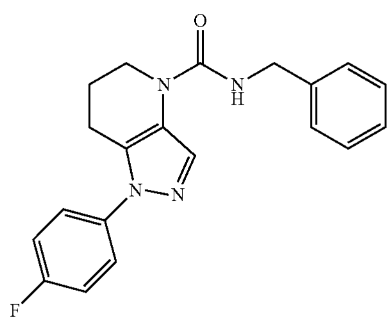 [SMILES: O=C(NCc1ccccc1)N1CCCc2c1cnn2-c1ccc(F)cc1] | 351.6 | 1.58 |
| 20 | 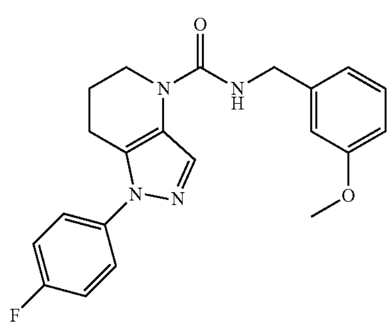 [SMILES: COc1cccc(CNC(=O)N2CCCc3c2cnn3-c2ccc(F)cc2)c1] | 381.7 | 1.57 |
| 21 | 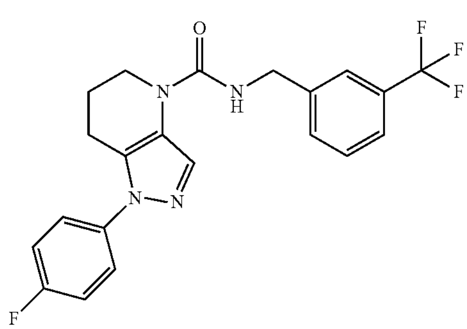 [SMILES: O=C(NCc1cccc(C(F)(F)F)c1)N1CCCc2c1cnn2-c1ccc(F)cc1] | 419.7 | 1.71 |

TABLE I-continued

| Example # | Structure | HPLC-MS Data [a] m/z [M + H]+ [b] | Retention time (min) |
|---|---|---|---|
| 22 | 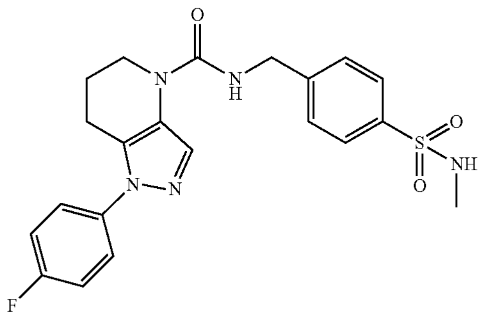 [SMILES: CNS(=O)(=O)c1ccc(CNC(=O)N2CCCc3c2cnn3-c2ccc(F)cc2)cc1] | 444.7 | 1.39 |
| 23 | 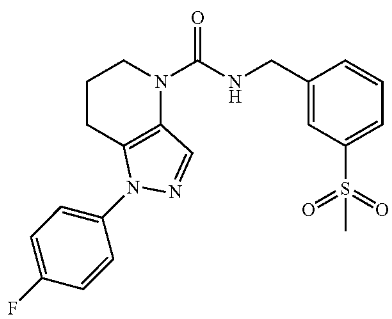 | 429.6 | 1.39 |
| 24 | 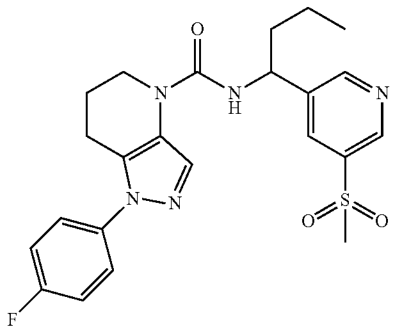 [SMILES: CCCC(NC(=O)N1CCCc2c1cnn2-c1ccc(F)cc1)c1cncc(S(C)(=O)=O)c1] | 472.7 | 1.49 |
| 25 | 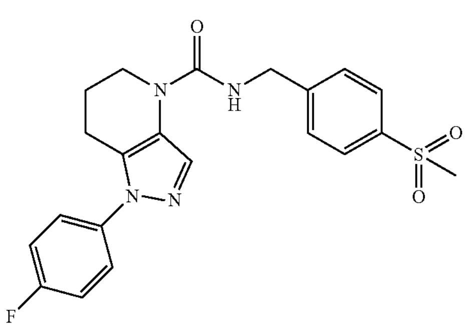 [SMILES: CS(=O)(=O)c1ccc(CNC(=O)N2CCCc3c2cnn3-c2ccc(F)cc2)cc1] | 429.6 | 1.40 |

TABLE I-continued

| Example # | Structure | m/z [M + H]+ (b) | Retention time (min) |
|---|---|---|---|
| 26 | 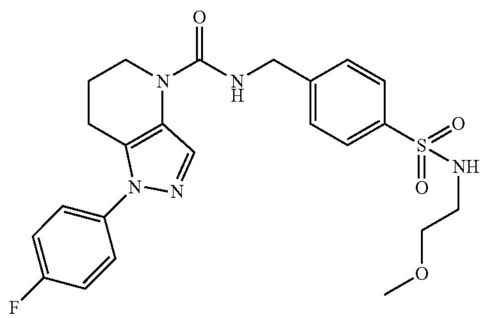 [SMILES: COCCNS(=O)(=O)c1ccc(CNC(=O)N2CCCc3c2cnn3-c2ccc(F)cc2)cc1] | 488.7 | 1.50 |
| 27 | 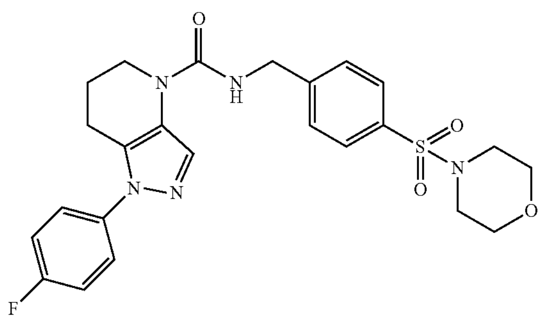 [SMILES: O=C(NCc1ccc(S(=O)(=O)N2CCOCC2)cc1)N1CCCc2c1cnn2-c1ccc(F)cc1] | 500.7 | 1.50 |
| 28 | 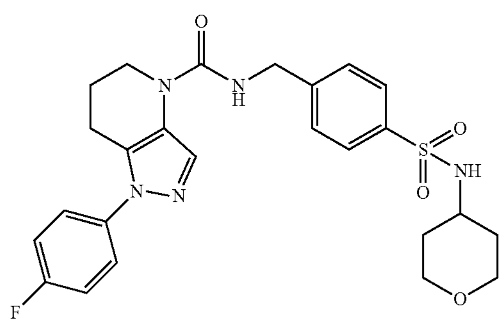 [SMILES: O=C(NCc1ccc(S(=O)(=O)NC2CCOCC2)cc1)N1CCCc2c1cnn2-c1ccc(F)cc1] | 514.7 | 1.42 |
| 29 | 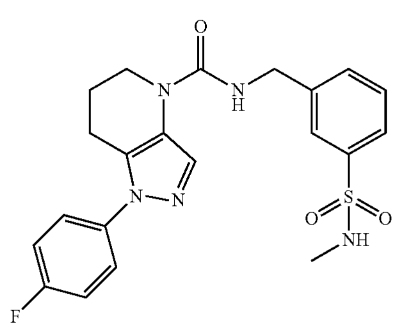 [SMILES: CNS(=O)(=O)c1cccc(CNC(=O)N2CCCc3c2cnn3-c2ccc(F)cc2)c1] | 444.3 | 1.43 |

HPLC-MS Data (a)

TABLE I-continued

| Example # | Structure | m/z [M + H]+ (b) | Retention time (min) |
|---|---|---|---|
| 30 | 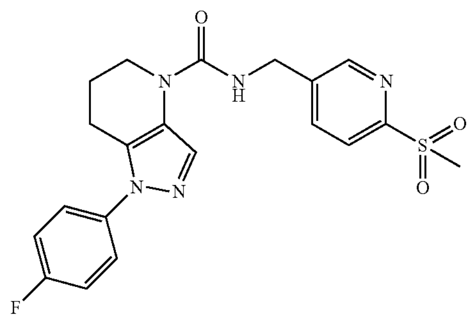 [SMILES: CS(=O)(=O)c1ccc(CNC(=O)N2CCCc3c2cnn3-c2ccc(F)cc2)cn1] | 430.7 | 1.35 |
| 31 | 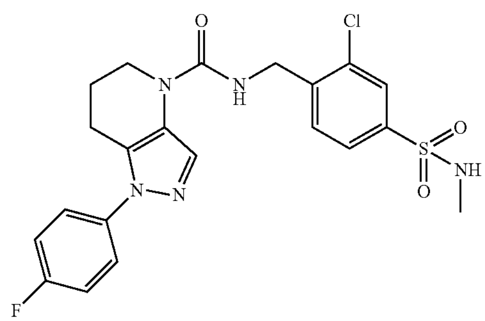 | 478.6 | 1.53 |
| 32 | 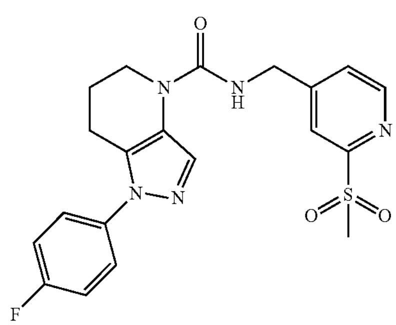 [SMILES: CS(=O)(=O)c1cc(CNC(=O)N2CCCc3c2cnn3-c2ccc(F)cc2)ccn1] | 430.7 | 1.34 |
| 33 | 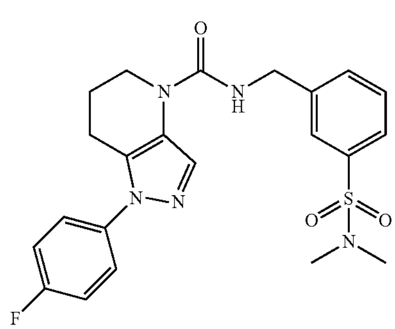 [SMILES: CN(C)S(=O)(=O)c1cccc(CNC(=O)N2CCCc3c2cnn3-c2ccc(F)cc2)c1] | 458.7 | 1.55 |

TABLE I-continued

| Example # | Structure | m/z [M + H]+ (b) | Retention time (min) |
|---|---|---|---|
| 34 | 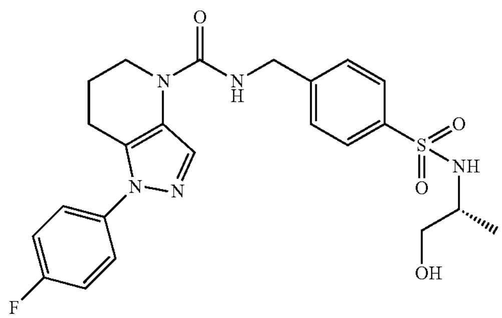 [SMILES: C[C@H](CO)NS(=O)(=O)c1ccc(CNC(=O)N2CCCc3c2cnn3-c2ccc(F)cc2)cc1] | 488.7 | 1.48 |
| 35 | 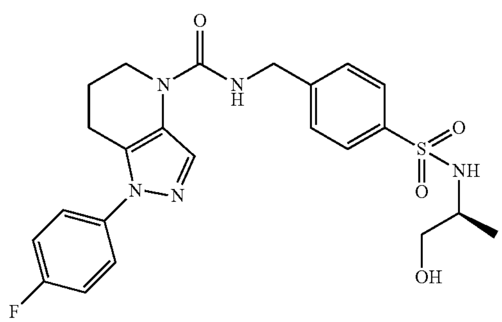 [SMILES: C[C@@H](CO)NS(=O)(=O)c1ccc(CNC(=O)N2CCCc3c2cnn3-c2ccc(F)cc2)cc1] | 488.7 | 1.49 |
| 36 | 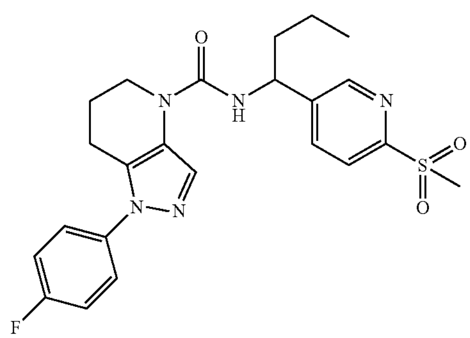 [SMILES: CCCC(NC(=O)N1CCCc2c1cnn2-c1ccc(F)cc1)c1ccc(S(C)(=O)=O)nc1] | 472.7 | 1.54 |
| 37 | 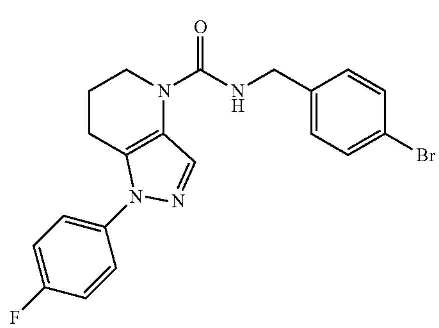 [SMILES: O=C(NCc1ccc(Br)cc1)N1CCCc2c1cnn2-c1ccc(F)cc1] | 429.6 431.6 | 1.70 |

TABLE I-continued

| Example # | Structure | HPLC-MS Data [a] m/z [M + H]+ [b] | Retention time (min) |
|---|---|---|---|
| 38 | 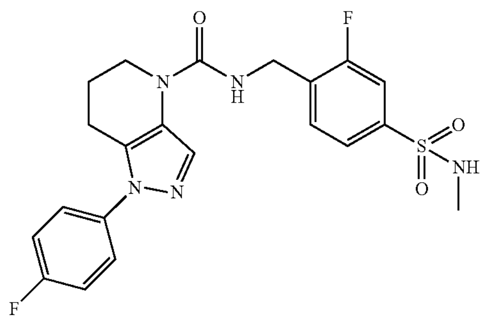 [SMILES: CNS(=O)(=O)c1ccc(CNC(=O)N2CCCc3c2cnn3-c2ccc(F)cc2)c(F)c1] | 462.7 | 1.47 |
| 39 | 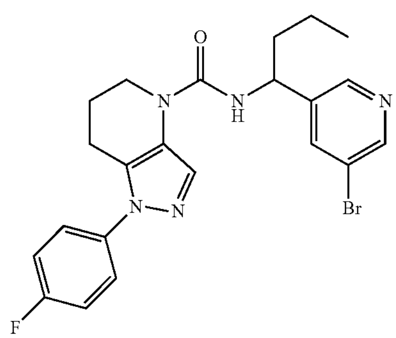 [SMILES: CCCC(NC(=O)N1CCCc2c1cnn2-c1ccc(F)cc1)c1cncc(Br)c1] | 472.6 474.6 | 1.69 |
| 40 | 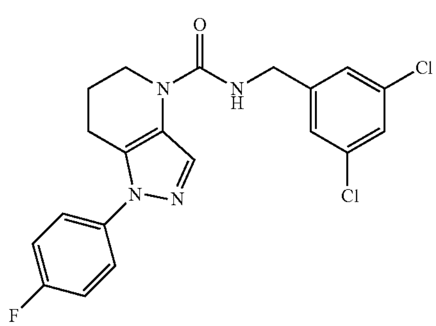 [SMILES: O=C(NCc1cc(Cl)cc(Cl)c1)N1CCCc2c1cnn2-c1ccc(F)cc1] | 419.6 | 1.80 |
| 41 | 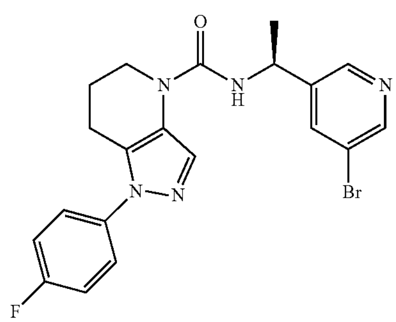 [SMILES: C[C@H](NC(=O)N1CCCc2c1cnn2-c1ccc(F)cc1)c1cncc(Br)c1] | 444.5 446.5 | 1.52 |

TABLE I-continued

| Example # | Structure | m/z [M + H]+ (b) | Retention time (min) |
|---|---|---|---|
| 42 | 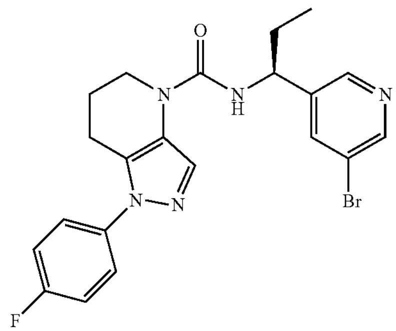 [SMILES: CC[C@H](NC(=O)N1CCCc2c1cnn2-c1ccc(F)cc1)c1cncc(Br)c1] | 458.5 460.5 | 1.60 |
| 43 | 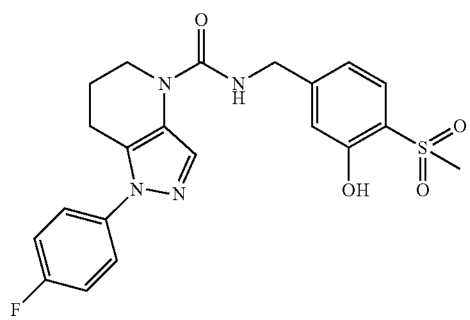 [SMILES: CS(=O)(=O)c1ccc(CNC(=O)N2CCCc3c2cnn3-c2ccc(F)cc2)cc1O] | 445.7 | 1.35 |
| 44 | 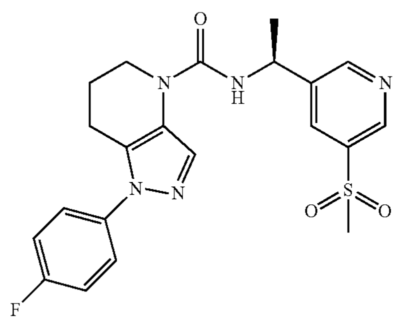 [SMILES: C[C@H](NC(=O)N1CCCc2c1cnn2-c1ccc(F)cc1)c1cncc(S(C)(=O)=O)c1] | 444.7 | 1.35 |
| 45 | 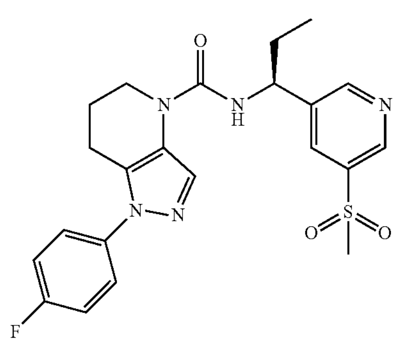 [SMILES: CC[C@H](NC(=O)N1CCCc2c1cnn2-c1ccc(F)cc1)c1cncc(S(C)(=O)=O)c1] | 458.7 | 1.41 |

TABLE I-continued

| Example # | Structure | m/z [M + H]+ [b] | Retention time (min) |
|---|---|---|---|
| 46 | 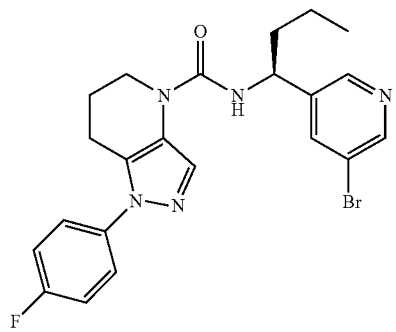 [SMILES: CCC[C@H](NC(=O)N1CCCc2c1cnn2-c1ccc(F)cc1)c1cncc(Br)c1] | 472.6 474.6 | 1.69 |
| 47 | 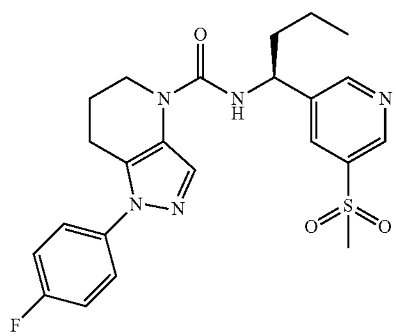 [SMILES: CCC[C@H](NC(=O)N1CCCc2c1cnn2-c1ccc(F)cc1)c1cncc(S(C)(=O)=O)c1] | 472.7 | 1.50 |
| 48 | 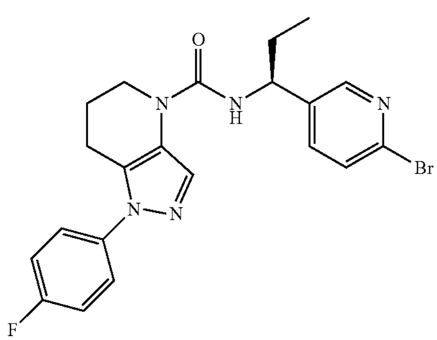 [SMILES: CC[C@H](NC(=O)N1CCCc2c1cnn2-c1ccc(F)cc1)c1ccc(Br)nc1] | 458.6 460.6 | 1.59 |
| 49 | 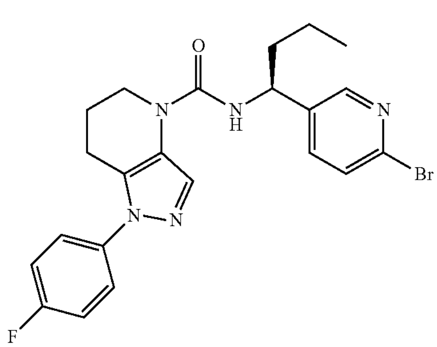 [SMILES: CCC[C@H](NC(=O)N1CCCc2c1cnn2-c1ccc(F)cc1)c1ccc(Br)nc1] | 472.6 474.6 | 1.68 |

HPLC-MS Data [a]

TABLE I-continued

| Example # | Structure | m/z [M + H]+ (b) | Retention time (min) |
|---|---|---|---|
| 50 | 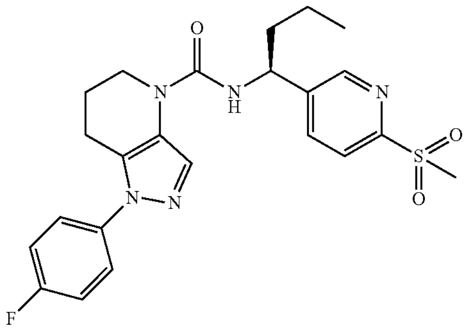 [SMILES: CCC[C@H](NC(=O)N1CCCc2c1cnn2-c1ccc(F)cc1)c1ccc(S(C)(=O)=O)nc1] | 472.7 | 1.52 |
| 51 | 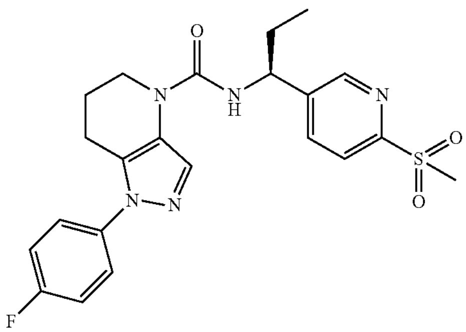 [SMILES: CC[C@H](NC(=O)N1CCCc2c1cnn2-c1ccc(F)cc1)c1ccc(S(C)(=O)=O)nc1] | 458.7 | 1.44 |
| 52 | 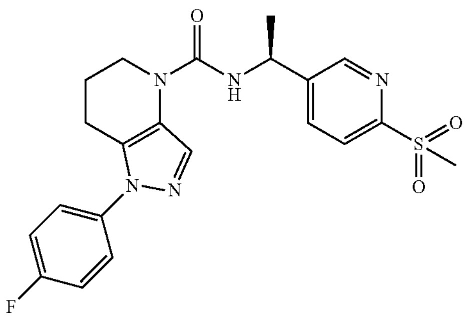 [SMILES: C[C@H](NC(=O)N1CCCc2c1cnn2-c1ccc(F)cc1)c1ccc(S(C)(=O)=O)nc1] | 444.7 | 1.37 |
| 53 | 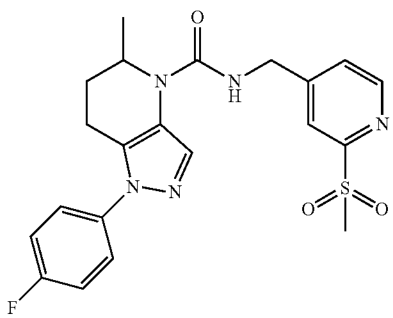 [SMILES: CC1CCc2c(cnn2-c2ccc(F)cc2)N1C(=O)NCc1ccnc(S(C)(=O)=O)c1] | 444.7 | 1.39 |

TABLE I-continued

| Example # | Structure | HPLC-MS Data [a] m/z [M + H]+ [b] | Retention time (min) |
|---|---|---|---|
| 54 | 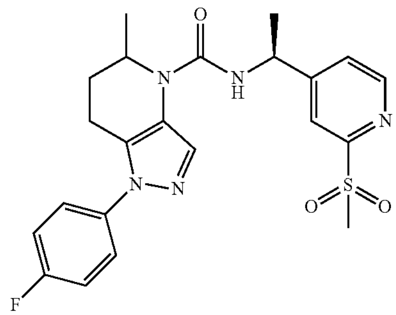 [SMILES: CC1CCc2c(cnn2-c2ccc(F)cc2)N1C(=O)N[C@@H](C)c1ccnc(S(C)(=O)=O)c1] | 458.8 | 1.45 |
| 55 | 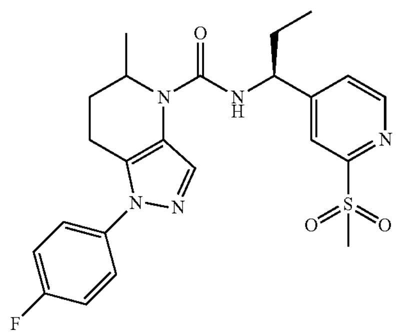 [SMILES: CC[C@H](NC(=O)N1c2cnn(-c3ccc(F)cc3)c2CCC1C)c1ccnc(S(C)(=O)=O)c1] | 472.7 | 1.53 |
| 56 | 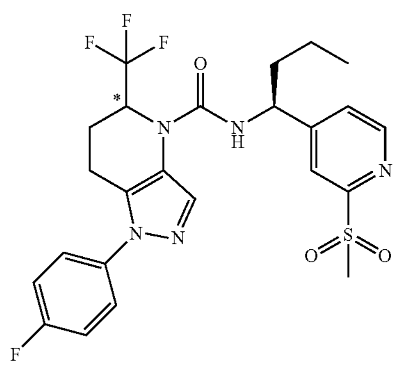 [SMILES: CCC[C@H](NC(=O)N1c2cnn(-c3ccc(F)cc3)c2CCC1C(F)(F)F)c1ccnc(S(C)(=O)=O)c1] | 540.1 | 1.63 |
| 57 | 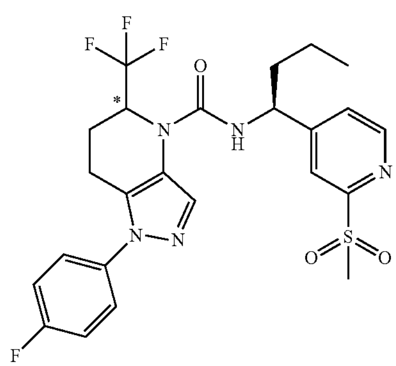 [SMILES: CCC[C@H](NC(=O)N1c2cnn(-c3ccc(F)cc3)c2CCC1C(F)(F)F)c1ccnc(S(C)(=O)=O)c1] | 540.2 | 1.62 |

TABLE I-continued

| Example # | Structure | m/z [M + H]+ [b] | Retention time (min) |
|---|---|---|---|
| 58 | 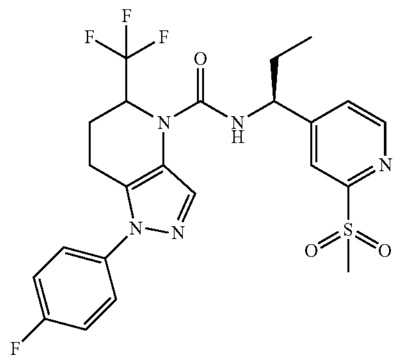 [SMILES: CC[C@H](NC(=O)N1c2cnn(-c3ccc(F)cc3)c2CCC1C(F)(F)F)c1ccnc(S(C)(=O)=O)c1] | 526.2 | 1.59 |
| 59 | 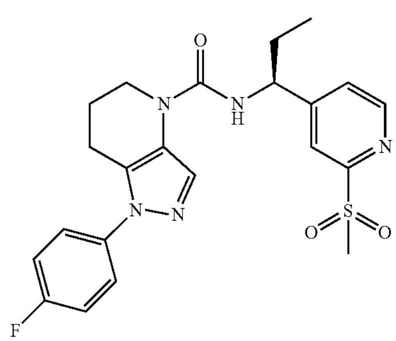 [SMILES: CC[C@H](NC(=O)N1CCCc2c1cnn2-c1ccc(F)cc1)c1ccnc(S(C)(=O)=O)c1] | 458.2 | 1.41 |
| 60 | 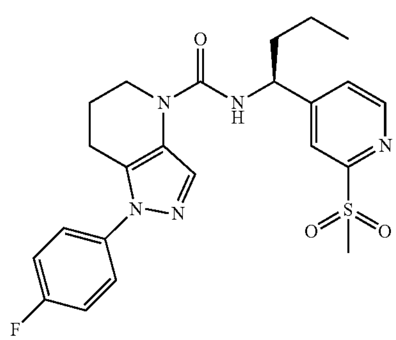 [SMILES: CCC[C@H](NC(=O)N1CCCc2c1cnn2-c1ccc(F)cc1)c1ccnc(S(C)(=O)=O)c1] | 472.2 | 1.48 |
| 61 | 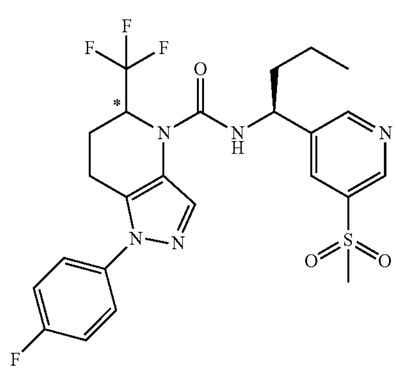 [SMILES: CCC[C@H](NC(=O)N1c2cnn(-c3ccc(F)cc3)c2CCC1C(F)(F)F)c1cncc(S(C)(=O)=O)c1] | 540.1 | 1.61 |

TABLE I-continued

| Example # | Structure | HPLC-MS Data [a] | |
|---|---|---|---|
| | | m/z [M + H]+ [b] | Retention time (min) |
| 62 | 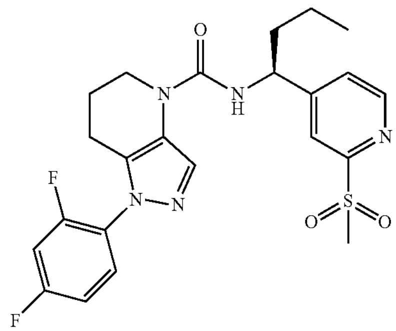 [SMILES: CCC[C@H](NC(=O)N1CCCc2c1cnn2-c1ccc(F)cc1F)c1ccnc(S(C)(=O)=O)c1] | 490.2 | 1.49 |
| 63 | 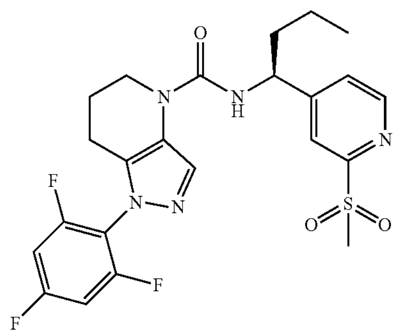 [SMILES: CCC[C@H](NC(=O)N1CCCc2c1cnn2-c1c(F)cc(F)cc1F)c1ccnc(S(C)(=O)=O)c1] | 508.2 | 1.52 |
| 64 | 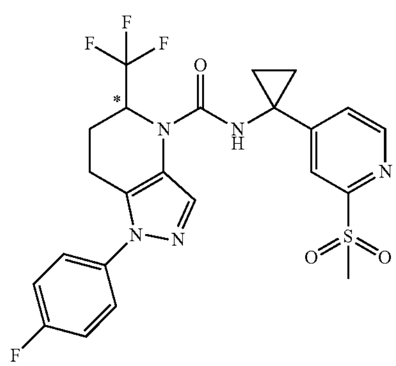 [SMILES: CS(=O)(=O)c1cc(C2(NC(=O)N3c4cnn(-c5ccc(F)cc5)c4CCC3C(F)(F)F)CC2)ccn1] | 524.1 | 1.75 |
| 65 | 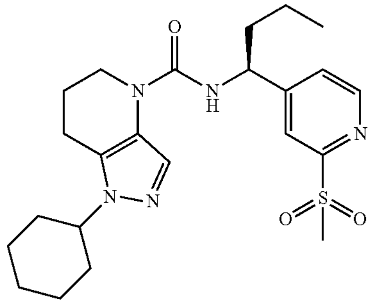 [SMILES: CCC[C@H](NC(=O)N1CCCc2c1cnn2C1CCCCC1)c1ccnc(S(C)(=O)=O)c1] | 460.2 | 1.51 |

TABLE I-continued

| Example # | Structure | m/z [M + H]+ (b) | Retention time (min) |
|---|---|---|---|
| 66 | 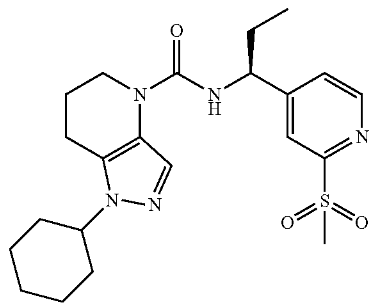 [SMILES: CC[C@H](NC(=O)N1CCCc2c1cnn2C1CCCCC1)c1ccnc(S(C)(=O)=O)c1] | 445.9 | 1.46 |
| 67 | 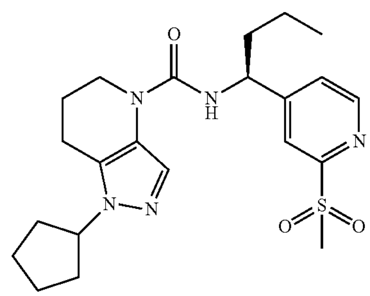 [SMILES: CCC[C@H](NC(=O)N1CCCc2c1cnn2C1CCCC1)c1ccnc(S(C)(=O)=O)c1] | 446.0 | 1.62 |
| 68 | 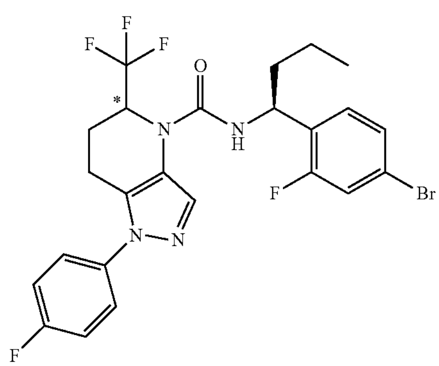 [SMILES: CCC[C@H](NC(=O)N1c2cnn(-c3ccc(F)cc3)c2CCC1C(F)(F)F)c1ccc(Br)cc1F] | 557.2 559.0 | 2.0 |
| 69 | 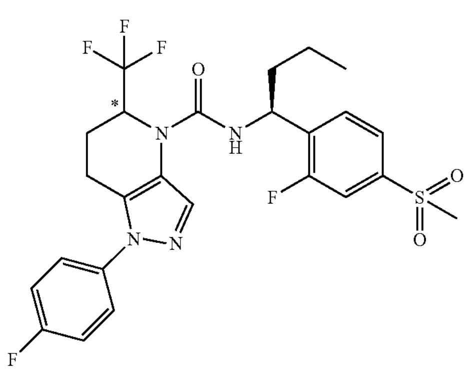 [SMILES: CCC[C@H](NC(=O)N1c2cnn(-c3ccc(F)cc3)c2CCC1C(F)(F)F)c1ccc(S(C)(=O)=O)cc1F] | 557.4 | 1.82 |

TABLE I-continued

| Example # | Structure | HPLC-MS Data [a] m/z [M + H]+ [b] | Retention time (min) |
|---|---|---|---|
| 70 | 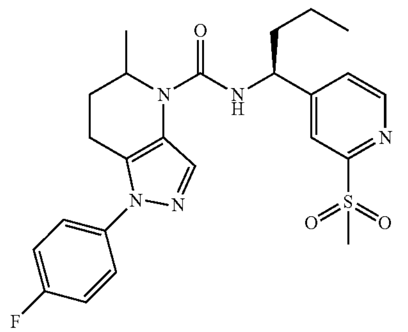 [SMILES: CCC[C@H](NC(=O)N1c2cnn(-c3ccc(F)cc3)c2CCC1C)c1ccnc(S(C)(=O)=O)c1] | 486.1 | 1.98 |
| 71 | 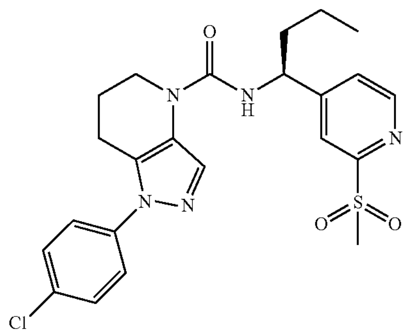 [SMILES: CCC[C@H](NC(=O)N1CCCc2c1cnn2-c1ccc(Cl)cc1)c1ccnc(S(C)(=O)=O)c1] | 490.2 | 2.08 |
| 72 | 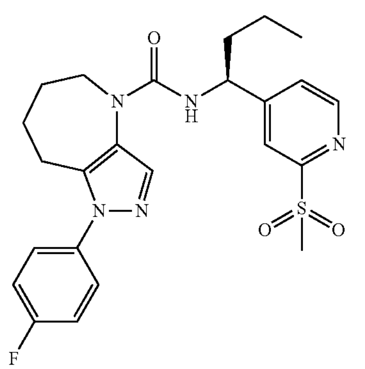 [SMILES: CCC[C@H](NC(=O)N1CCCCc2c1cnn2-c1ccc(F)cc1)c1ccnc(S(C)(=O)=O)c1] | 486.0 | 1.98 |
| 73 | 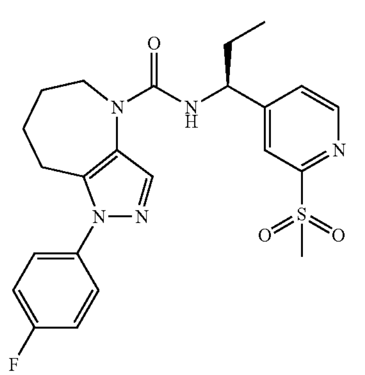 [SMILES: CC[C@H](NC(=O)N1CCCCc2c1cnn2-c1ccc(F)cc1)c1ccnc(S(C)(=O)=O)c1] | 472.2 | 0.83 |

TABLE I-continued

| Example # | Structure | HPLC-MS Data m/z [M + H]+ (b) | Retention time (min) |
|---|---|---|---|
| 74 | 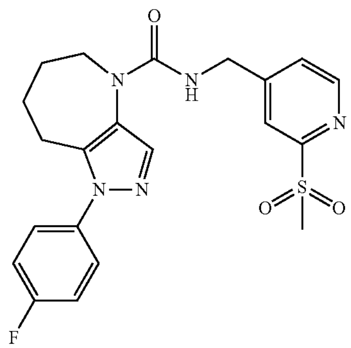 [SMILES: CS(=O)(=O)c1cc(CNC(=O)N2CCCCc3c2cnn3-c2ccc(F)cc2)ccn1] | 444.2 | 0.74 |
| 75 | 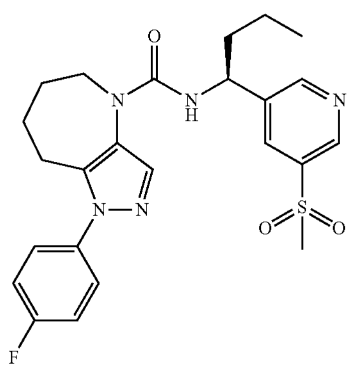 [SMILES: CCC[C@H](NC(=O)N1CCCCc2c1cnn2-c1ccc(F)cc1)c1cncc(S(C)(=O)=O)c1] | 486.2 | 0.87 |
| 76 | 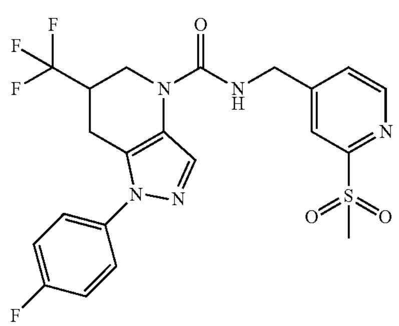 [SMILES: CS(=O)(=O)c1cc(CNC(=O)N2CC(C(F)(F)F)Cc3c2cnn3-c2ccc(F)cc2)ccn1] | 498.7 | 1.49 |
| 77 | 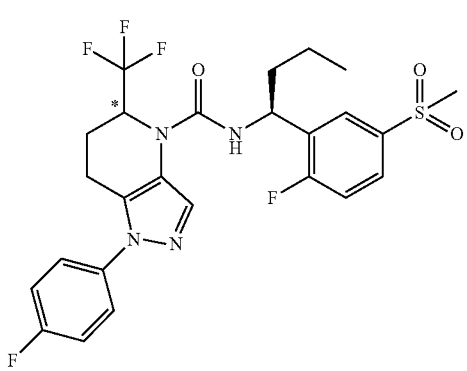 [SMILES: CCC[C@H](NC(=O)N1c2cnn(-c3ccc(F)cc3)c2CCC1C(F)(F)F)c1cc(S(C)(=O)=O)ccc1F] | 557.4 | 1.80 |

TABLE I-continued

| Example # | Structure | HPLC-MS Data [a] m/z [M + H]+ [b] | Retention time (min) |
|---|---|---|---|
| 78 | 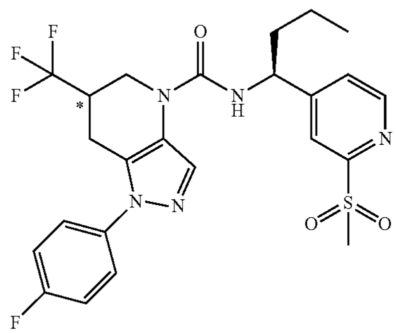 [SMILES: CCC[C@H](NC(=O)N1CC(C(F)(F)F)Cc2c1cnn2-c1ccc(F)cc1)c1ccnc(S(C)(=O)=O)c1] | 540.1 | 1.62 |
| 79 | 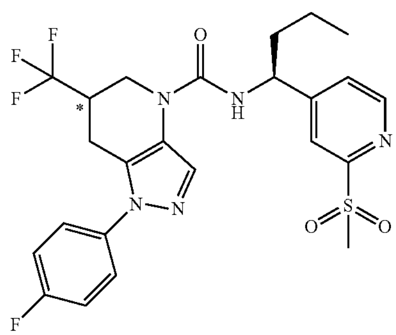 [SMILES: CCC[C@H](NC(=O)N1CC(C(F)(F)F)Cc2c1cnn2-c1ccc(F)cc1)c1ccnc(S(C)(=O)=O)c1] | 540.1 | 1.61 |
| 80 | 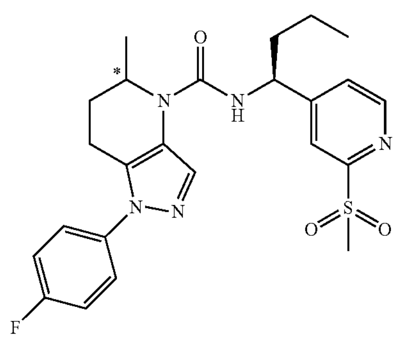 [SMILES: CCC[C@H](NC(=O)N1c2cnn(-c3ccc(F)cc3)c2CCC1C)c1ccnc(S(C)(=O)=O)c1] | 486.3 | 0.90 |
| 81 | 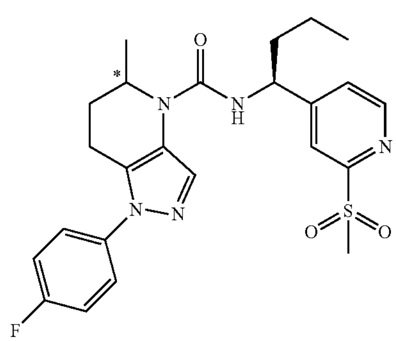 [SMILES: CCC[C@H](NC(=O)N1c2cnn(-c3ccc(F)cc3)c2CCC1C)c1ccnc(S(C)(=O)=O)c1] | 486.2 | 0.90 |

TABLE I-continued

| Example # | Structure | m/z [M + H]+ [b] | Retention time (min) |
|---|---|---|---|
| 82 | 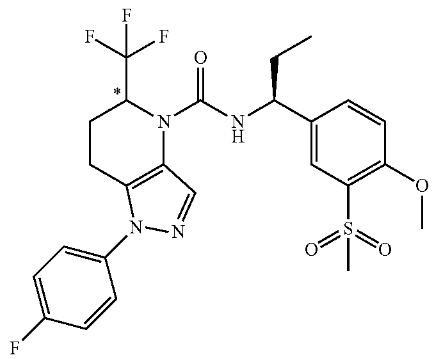 [SMILES: CC[C@H](NC(=O)N1c2cnn(-c3ccc(F)cc3)c2CCC1C(F)(F)F)c1ccc(OC)c(S(C)(=O)=O)c1] | 555.2 | 1.59 |
| 83 | 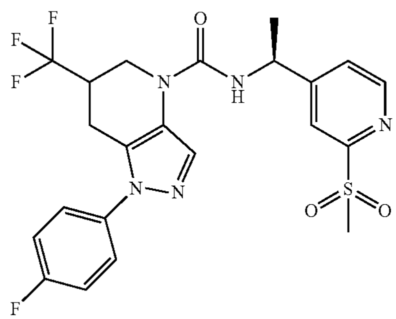 [SMILES: C[C@H](NC(=O)N1CC(C(F)(F)F)Cc2c1cnn2-c1ccc(F)cc1)c1ccnc(S(C)(=O)=O)c1] | 512.1 | 1.51 |
| 84 | 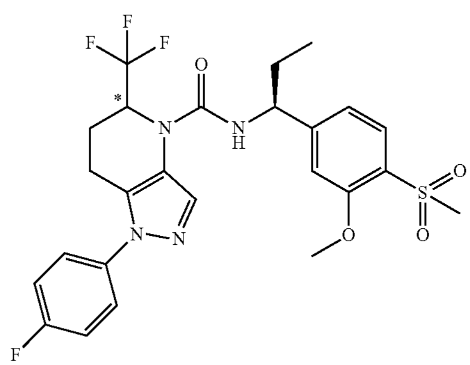 [SMILES: CC[C@H](NC(=O)N1c2cnn(-c3ccc(F)cc3)c2CCC1C(F)(F)F)c1ccc(S(C)(=O)=O)c(OC)c1] | 555.1 | 1.60 |
| 85 | 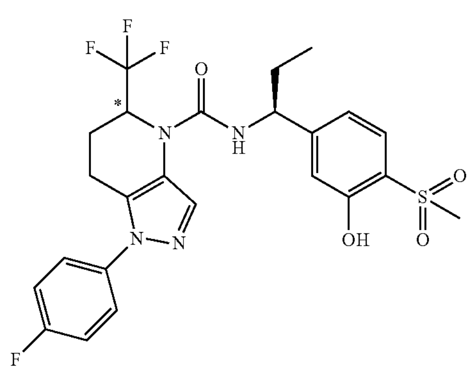 [SMILES: CC[C@H](NC(=O)N1c2cnn(-c3ccc(F)cc3)c2CCC1C(F)(F)F)c1ccc(S(C)(=O)=O)c(O)c1] | 541.2 | 1.52 |

TABLE I-continued

| Example # | Structure | m/z [M + H]+ [b] | Retention time (min) |
|---|---|---|---|
| 86 | 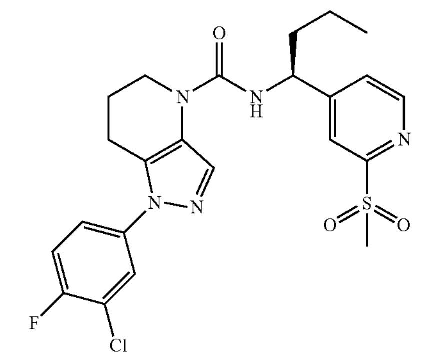 [SMILES: CCC[C@H](NC(=O)N1CCCc2c1cnn2-c1ccc(F)c(Cl)c1)c1ccnc(S(C)(=O)=O)c1] | 506.2 | 1.59 |
| 87 | 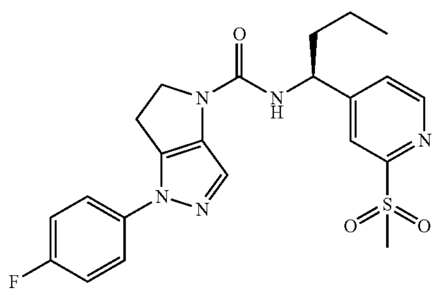 [SMILES: CCC[C@H](NC(=O)N1CCc2c1cnn2-c1ccc(F)cc1)c1ccnc(S(C)(=O)=O)c1] | 458.2 | 1.48 |
| 88 | 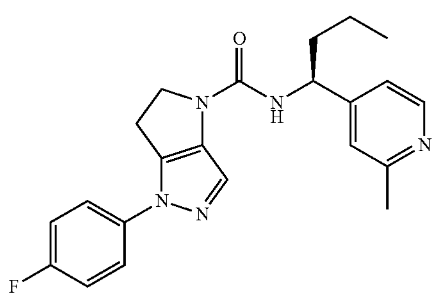 [SMILES: CCC[C@H](NC(=O)N1CCc2c1cnn2-c1ccc(F)cc1)c1ccnc(C)c1] | 395.6 | 1.24 |
| 89 | 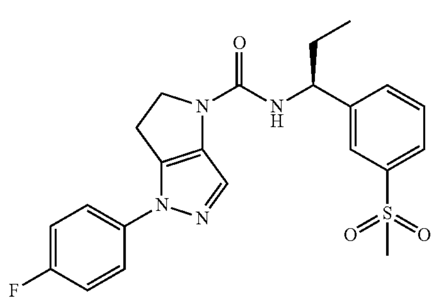 [SMILES: CC[C@H](NC(=O)N1CCc2c1cnn2-c1ccc(F)cc1)c1cccc(S(C)(=O)=O)c1] | 443.1 | 1.48 |

HPLC-MS Data [a]

TABLE I-continued

| Example # | Structure | HPLC-MS Data m/z [M + H]+ (b) | Retention time (min) |
|---|---|---|---|
| 90 | 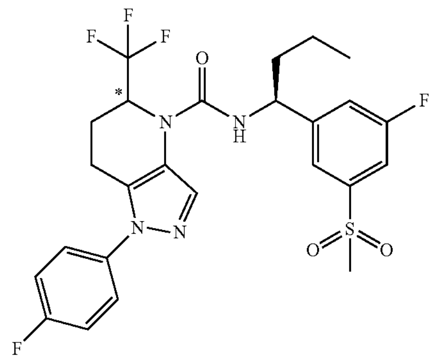 [SMILES: CCC[C@H](NC(=O)N1c2cnn(-c3ccc(F)cc3)c2CCC1C(F)(F)F)c1cc(F)cc(S(C)(=O)=O)c1] | 557.1 | 1.68 |
| 91 | 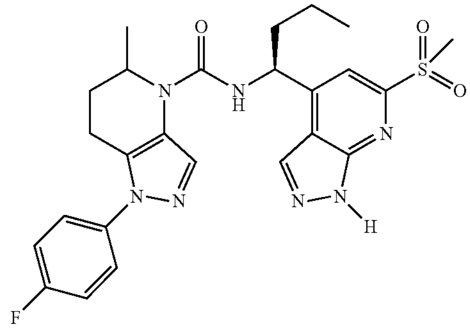 [SMILES: CCC[C@H](NC(=O)N1c2cnn(-c3ccc(F)cc3)c2CCC1C)c1cc(S(C)(=O)=O)nc2[nH]ncc12] | 483.8 | 1.43 |
| 92 | 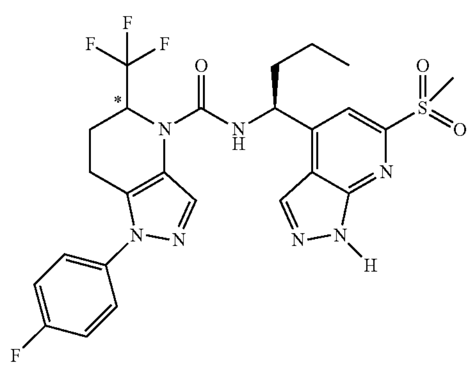 [SMILES: CCC[C@H](NC(=O)N1c2cnn(-c3ccc(F)cc3)c2CCC1C(F)(F)F)c1cc(S(C)(=O)=O)nc2[nH]ncc12] | 537.8 | 1.54 |
| 93 | 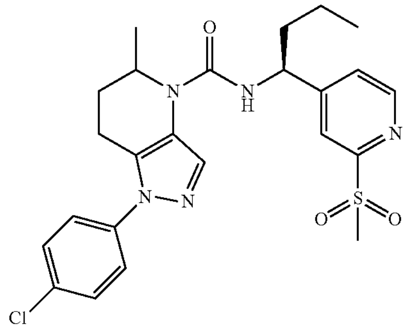 [SMILES: CCC[C@H](NC(=O)N1c2cnn(-c3ccc(Cl)cc3)c2CCC1C)c1ccnc(S(C)(=O)=O)c1] | 502.2 | 1.61 |

TABLE I-continued
| Example # | Structure | m/z [M + H]+ [b] | Retention time (min) |
|---|---|---|---|
| 94 | 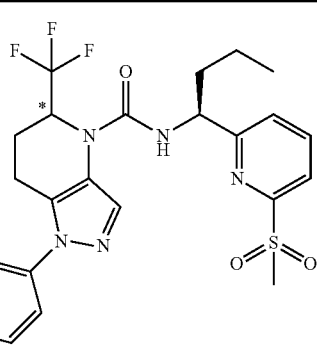 | 540.2 | 1.65 |
| 95 | 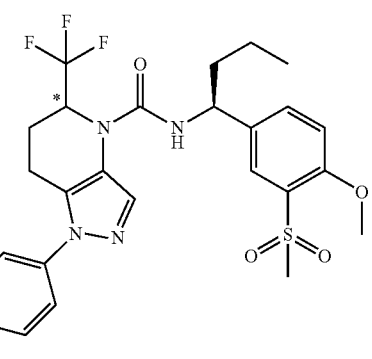 | 569.2 | 1.67 |
| 96 | 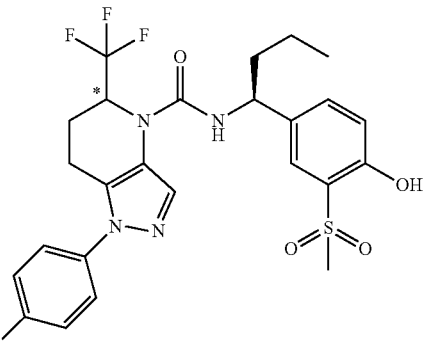 | 555.2 | 1.59 |
| 97 | 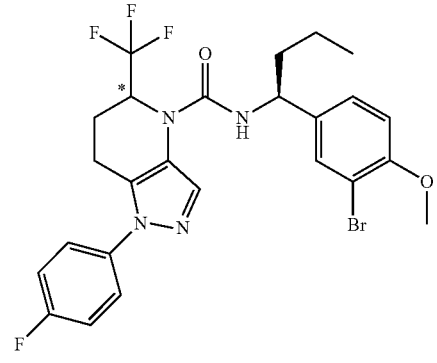 [SMILES: CCC[C@H](NC(=O)N1c2cnn(-c3ccc(F)cc3)c2CCC1C(F)(F)F)c1ccc(OC)c(Br)c1] | 569.2<br>571.1 | 1.83 |

TABLE I-continued

| Example # | Structure | m/z [M + H]+ (b) | Retention time (min) |
|---|---|---|---|
| 98 | 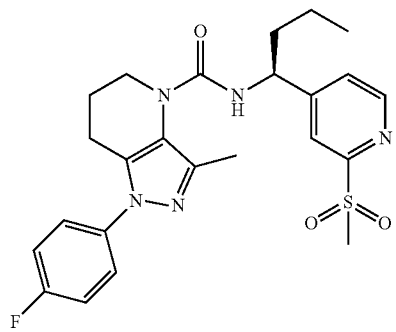 [SMILES: CCC[C@H](NC(=O)N1CCCc2c1c(C)nn2-c1ccc(F)cc1)c1ccnc(S(C)(=O)=O)c1] | 486.2 | 0.89 |
| 99 | 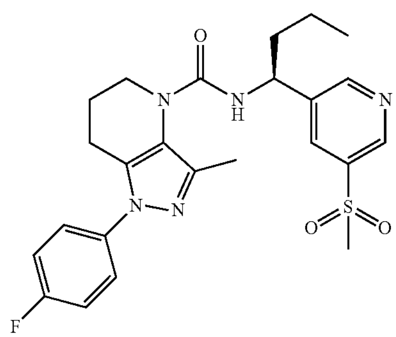 [SMILES: CCC[C@H](NC(=O)N1CCCc2c1c(C)nn2-c1ccc(F)cc1)c1cncc(S(C)(=O)=O)c1] | 486.2 | 0.86 |
| 100 | 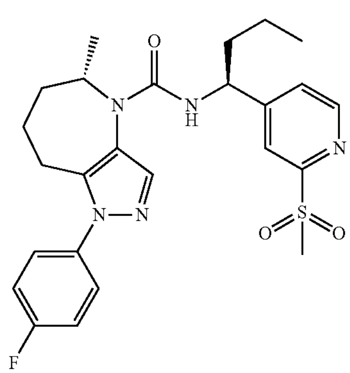 [SMILES: CCC[C@H](NC(=O)N1c2cnn(-c3ccc(F)cc3)c2CCC[C@@H]1C)c1ccnc(S(C)(=O)=O)c1] | 500.3 | 1.61 |
| 101 | 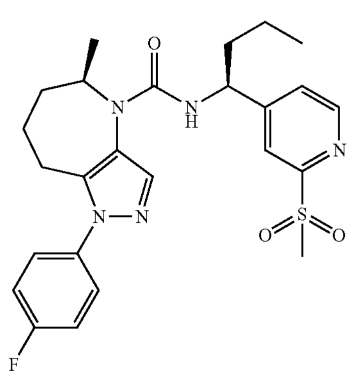 [SMILES: CCC[C@H](NC(=O)N1c2cnn(-c3ccc(F)cc3)c2CCC[C@H]1C)c1ccnc(S(C)(=O)=O)c1] | 500.2 | 0.94 |

TABLE I-continued

| Example # | Structure | m/z [M + H]+ (b) | Retention time (min) |
|---|---|---|---|
| 102 | 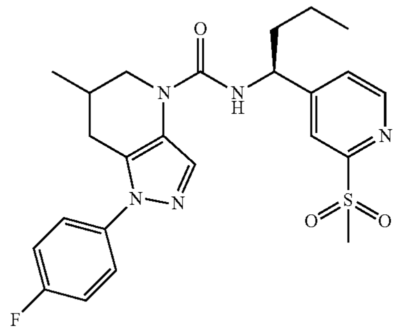 [SMILES: CCC[C@H](NC(=O)N1CC(C)Cc2c1cnn2-c1ccc(F)cc1)c1ccnc(S(C)(=O)=O)c1] | 486.2 | 1.58 |
| 103 | 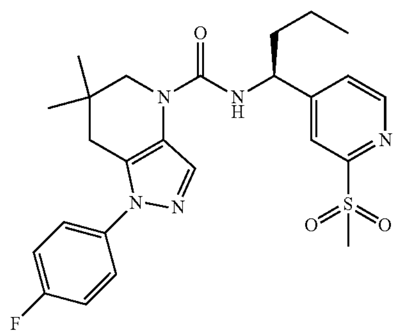 [SMILES: CCC[C@H](NC(=O)N1CC(C)(C)Cc2c1cnn2-c1ccc(F)cc1)c1ccnc(S(C)(=O)=O)c1] | 500.3 | 1.60 |
| 104 | 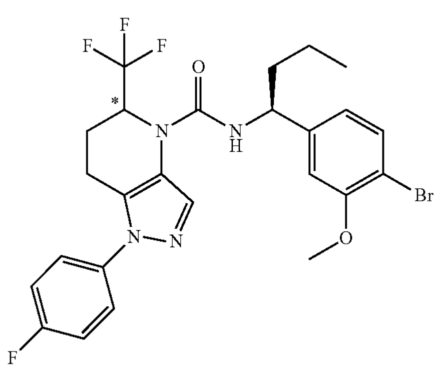 [SMILES: CCC[C@H](NC(=O)N1c2cnn(-c3ccc(F)cc3)c2CCC1C(F)(F)F)c1ccc(Br)c(OC)c1] | 569.2 571.1 | 1.85 |
| 105 | 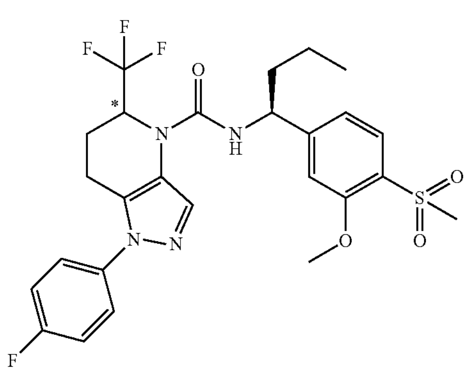 [SMILES: CCC[C@H](NC(=O)N1c2cnn(-c3ccc(F)cc3)c2CCC1C(F)(F)F)c1ccc(S(C)(=O)=O)c(OC)c1] | 569.1 | 1.63 |

TABLE I-continued

| Example # | Structure | m/z [M + H]+ (b) | Retention time (min) |
|---|---|---|---|
| 106 | 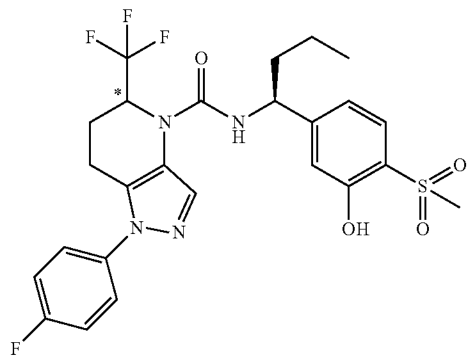 [SMILES: CCC[C@H](NC(=O)N1c2cnn(-c3ccc(F)cc3)c2CCC1C(F)(F)F)c1ccc(S(C)(=O)=O)c(O)c1] | 555.2 | 1.58 |
| 107 | 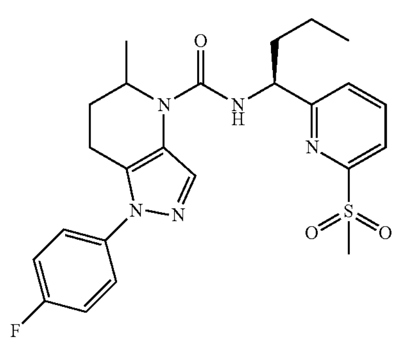 | 486.1 | 1.56 |
| 108 | 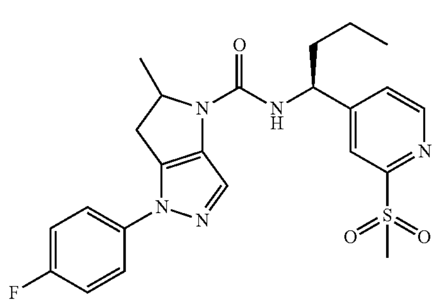 [SMILES: CCC[C@H](NC(=O)N1c2cnn(-c3ccc(F)cc3)c2CC1C)c1ccnc(S(C)(=O)=O)c1] | 472.1 | 1.51 |
| 109 | 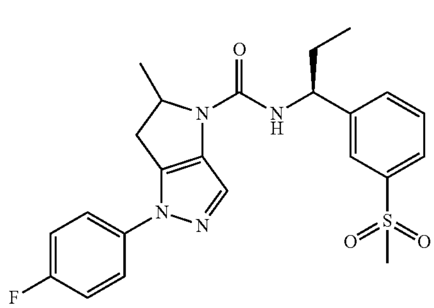 [SMILES: CC[C@H](NC(=O)N1c2cnn(-c3ccc(F)cc3)c2CC1C)c1cccc(S(C)(=O)=O)c1] | 458.4 | 1.52 |

TABLE I-continued

| Example # | Structure | m/z [M + H]+ (b) | Retention time (min) |
|---|---|---|---|
| 110 | 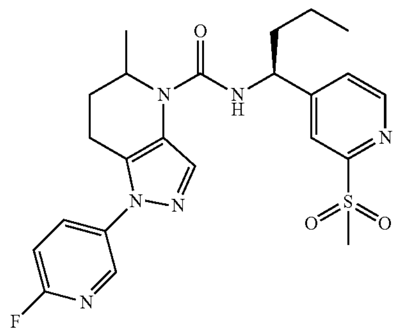 [SMILES: CCC[C@H](NC(=O)N1c2cnn(-c3ccc(F)nc3)c2CCC1C)c1ccnc(S(C)(=O)=O)c1] | 487.3 | 1.53 |
| 111 | 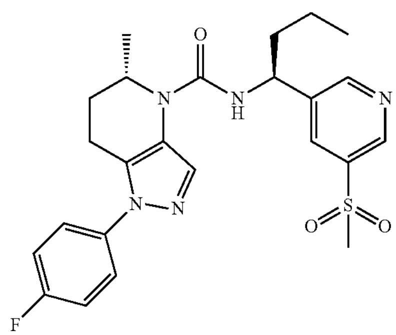 [SMILES: CCC[C@H](NC(=O)N1c2cnn(-c3ccc(F)cc3)c2CC[C@@H]1C)c1cncc(S(C)(=O)=O)c1] | 486.1 | 1.49 |
| 112 | 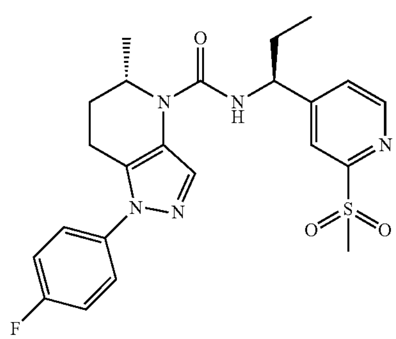 [SMILES: CC[C@H](NC(=O)N1c2cnn(-c3ccc(F)cc3)c2CC[C@@H]1C)c1ccnc(S(C)(=O)=O)c1] | 474.2 | 1.46 |
| 113 | 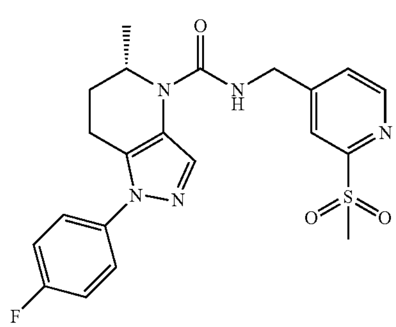 [SMILES: C[C@H]1CCc2c(cnn2-c2ccc(F)cc2)N1C(=O)NCc1ccnc(S(C)(=O)=O)c1] | 444.2 | 1.38 |

TABLE I-continued

| Example # | Structure | HPLC-MS Data [a] m/z [M + H]+ [b] | Retention time (min) |
|---|---|---|---|
| 114 | 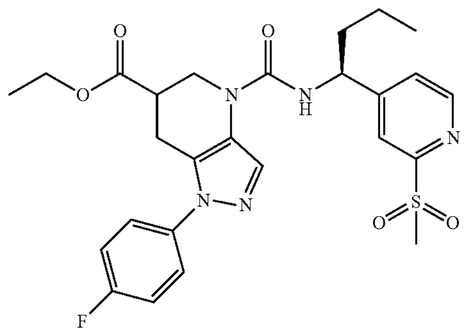 [SMILES: CCC[C@H](NC(=O)N1CC(C(=O)OCC)Cc2c1cnn2-c1ccc(F)cc1)c1ccnc(S(C)(=O)=O)c1] | 544.2 | 1.55 |
| 115 | 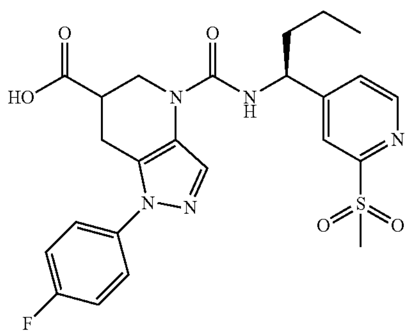 [SMILES: CCC[C@H](NC(=O)N1CC(C(=O)O)Cc2c1cnn2-c1ccc(F)cc1)c1ccnc(S(C)(=O)=O)c1] | 516.3 | 1.39 |
| 116 | 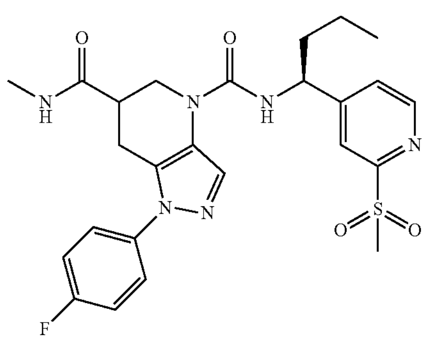 [SMILES: CCC[C@H](NC(=O)N1CC(C(=O)NC)Cc2c1cnn2-c1ccc(F)cc1)c1ccnc(S(C)(=O)=O)c1] | 529.2 | 1.38 |
| 117 | 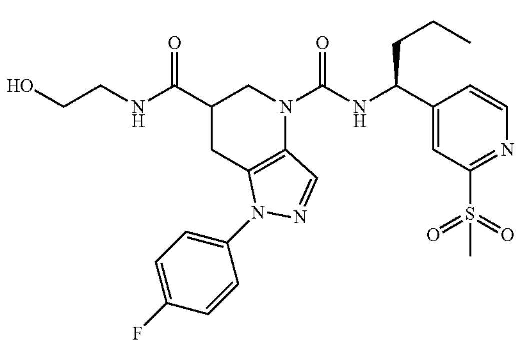 [SMILES: CCC[C@H](NC(=O)N1CC(C(=O)NCCO)Cc2c1cnn2-c1ccc(F)cc1)c1ccnc(S(C)(=O)=O)c1] | 559.3 | 1.31 |

TABLE I-continued

| Example # | Structure | HPLC-MS Data [a] m/z [M + H]+ [b] | Retention time (min) |
|---|---|---|---|
| 118 | 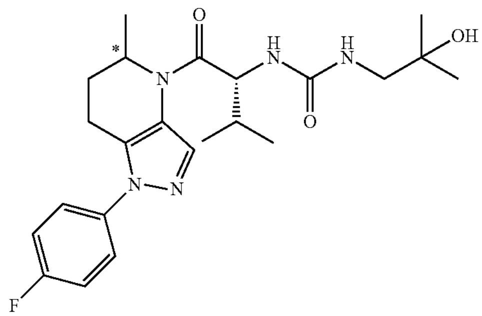 [SMILES: CC(C)[C@@H](NC(=O)NCC(C)(C)O)C(=O)N1c2cnn(-c3ccc(F)cc3)c2CCC1C] | 446.3 | 1.41 |
| 119 | 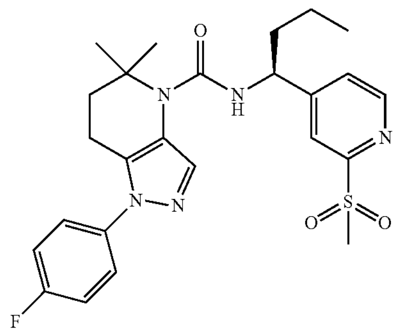 [SMILES: CCC[C@H](NC(=O)N1c2cnn(-c3ccc(F)cc3)c2CCC1(C)C)c1ccnc(S(C)(=O)=O)c1] | 500.1 | 1.65 |
| 120 | 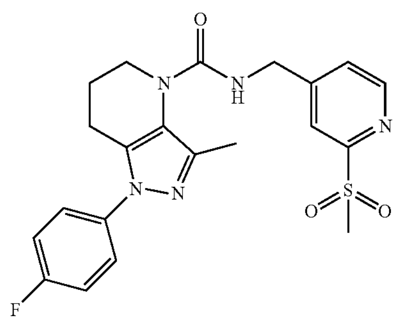 [SMILES: Cc1nn(-c2ccc(F)cc2)c2c1N(C(=O)NCc1ccnc(S(C)(=O)=O)c1)CCC2] | 444.2 | 0.73 |
| 121 | 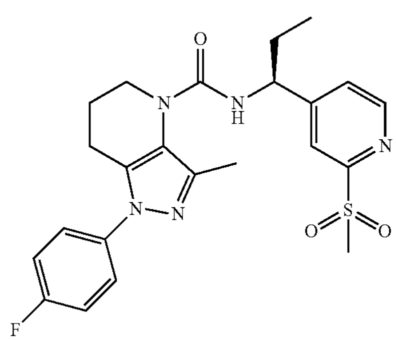 [SMILES: CC[C@H](NC(=O)N1CCCc2c1c(C)nn2-c1ccc(F)cc1)c1ccnc(S(C)(=O)=O)c1] | 472.2 | 0.83 |

[a] See Synthetic Example Section of HPLC-MS methods.
[b] [M + H]+ is reported for both $^{79}$Br and $^{81}$Br for bromine containing compounds.
The symbol (*) in Table I represents a chiral center with unassigned absolute stereochemical configuration (for example this center is either R or S stereochemistry).

or the pharmaceutically acceptable salts thereof.

In another aspect the invention relates to compounds—or the pharmaceutically acceptable salts—of the formula (I) as medicaments.

In another aspect the invention relates to pharmaceutical preparations, containing as active ingredient one or more compounds of the formula (I) or the pharmacologically acceptable salts thereof, optionally in combination with conventional excipients and/or carriers.

In another aspect the invention relates to the use of compounds of the formula (I) for preparing a pharmaceutical composition for the treatment of autoimmune diseases.

In another aspect the invention relates to a method of treating autoimmune diseases by administering a therapeutically effective amount of a compound of the formula (I).

In another aspect the invention relates to a pharmaceutical preparation comprising a compound of the formula (I), while the formula (I) compounds are optionally also in the form of the tautomers, the racemates, the enantiomers, the diastereomers, the mixtures thereof, or as pharmaceutically acceptable salts of all the above-mentioned forms.

In another aspect the invention relates to compounds of the invention which also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In another aspect the invention relates to the compounds of the formula (I) which may be used in combination with other active substances which are used in the treatments of autoimmune diseases. Such combinations can be administered either separately or in combination in a pharmaceutical composition.

DEFINITIONS

All terms as used herein in this specification, unless otherwise stated, shall be understood in their ordinary meaning as known in the art. Other more specific definitions are as follows:

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenyl acetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether ($Et_2O$), ethyl acetate (EtOAc), ethanol (EtOH), isopropanol, or acetonitrile, or a mixture thereof.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Alkenyl shall be understood to be an unsaturated $C_{2-n}$-alkyl with one or more degrees of unsaturation.

Alkoxy shall be understood to be a $C_{1-n}$-alkyl with an oxygen atom wherein the point of attachment is via the oxygen, for example methoxy: $H_3CO$—. Alkylthio shall be understood to mean the thio (S) analog of alkoxy. Alkylsulfonyl shall be understood to mean the sulfur oxidized analog of Alkylthio $C_{1-n}$-alkyl-$S(O)_2$—. Alkoxycarbonyl shall be understood to be a $C_{1-n}$-alkoxy with an addition of a C=O carbonyl group at the point of attachment: $C_{1-n}$-alkyl-O—C(O)—.

Acyl shall be understood to be a $C_{1-n}$-alkyl with an carbonyl group wherein the point of attachment is via the carbonyl, for example acetyl: $H_3CC(O)$—.

Amino shall be understood to be $NH_2$—, aminocarbonyl shall be understood to be $NH_2$—C(O)— wherein one or both hydrogens may be replaced by any substituent defined herein to form for example, mono- or di-$C_{1-n}$-alkylamino or $C_{1-n}$-alkylaminocarbonyl.

Carbocycles include hydrocarbon rings containing from three to twelve carbon atoms. These carbocycles may be either aromatic (aryl) or non-aromatic ring systems. The non-aromatic ring systems may be mono- or polyunsaturated. Preferred carbocycles include but are not limited to $C_{3-n}$-cycloalkyl and $C_{3-n}$-cycloalkenyl, phenyl, phenethyl, benzyl, indanyl, indenyl, naphthyl. Certain terms for cycloalkyl such as cyclobutanyl and cyclobutyl shall be used interchangeably.

The term "$C_{3-n}$-cycloalkyl", wherein n is an integer 4 to n (preferably n is 4-10), either alone or in combination with another radical denotes a cyclic, saturated hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, benzyl, phenethyl, indanyl, indenyl, naphthyl, anthracenyl, phenanthrenyl, tetrahydronaphthyl and dihydronaphthyl. The term "aryl" is intended to include all the possible hydrogenated forms.

The term "heterocyclyl" means a saturated or unsaturated mono- or polycyclic-ring systems including aromatic ring system containing one or more heteroatoms selected from N, O or $S(O)_r$ with r=0, 1 or 2 wherein none of the heteroatoms are part of the aromatic ring. The term "heterocycle" is intended to include all the possible isomeric forms. Unless otherwise stated, heterocycles include but are not limited to, for example oxiranyl, tetrahydrofuranyl, azepanyl, diazepanyl, azetidinyl, pyrrolidinyl, pyrrolinyl, piperidinyl, thiomorpholinyl, dioxalanyl, dioxanyl, piperazinyl, 1,3-dioxolanone, 1,3-dioxanone, 1,4-dioxanyl, piperidinonyl, tetrahydropyrimidonyl. The structures of the above will be apparent to one skilled in the art, other specific examples include morpholinyl

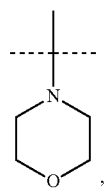

tetrahydropyranyl

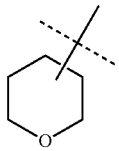

.

The term "heteroaryl" means a mono- or polycyclic-ring systems containing one or more heteroatoms selected from N, O or S(O)r with r=0, 1 or 2 wherein the heteroatom(s) is part of aromatic ring. The term "heteroaryl" is intended to include all the possible isomeric and hydrogenated forms. Unless otherwise stated, such heteroaryls include but are not limited to, for example: furanyl, pyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, quinolinyl, isoquinolinyl, quinazolinyl, indazolyl, indolyl, isoindolyl, benzofuranyl, benzopyranyl, pyrrolopiperidinyl and benzodioxolyl. The structures of the above will be apparent to one skilled in the art, other specific examples include: pyrrolopyridinyl

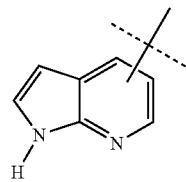

and pyridinyl

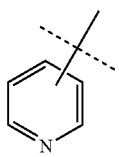

, and all the possible hydrogenated forms thereof.

Halogen encompasses fluorine, chlorine, bromine and/or iodine atoms.

Each of the above alkyl, cycloalkyl, aryl, heteroalkyl, heterocyclyl or heteroaryl, or any other substituent recited in this application, shall be understood to be optionally fully or partially halogenated where possible, preferably by Cl, F or Br.

Any ring structure which has shown this bond

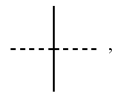

such bond shall be understood to be covalently attached to another moiety at the dashed line and covalently attached at any point in the ring (floating) that will replace a hydrogen atom and result in a stable bond, for example

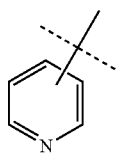

represent pyridinyl attached at the 2, 3 or 4 position.

Features and advantages of the present invention will become apparent from the following detailed Examples, which illustrate the fundamentals of the invention by way of example, without restricting its scope.

General Synthetic Methods

The invention additionally provides for methods for making compounds of formula I.

The compounds of the invention may be prepared by the general methods and examples presented below, and methods known to those of ordinary skill in the art and reported in the chemical literature. Unless otherwise specified, solvents, temperatures, pressures, and other reaction conditions may be readily selected by one of ordinary skill in the art.

Specific procedures are provided in the Synthetic Examples section. Intermediate benzyl amines are commercially available, or may be synthesized via catalytic reduction of the corresponding aryl nitriles with Pd/C (Van Rompaey, K. et al. *Tetrahedron* 2003, 59 (24), 4421) or Raney Ni (Gould, F. et al. *J. Org. Chem.* 1960, 25, 1658) or through displacement of a benzyl bromide with sodium azide and reduction. Intermediate aminomethylpyridines may also be commercially available or prepared by methods known to those skilled in the art. For example, methods of preparing 1-substituted-1-(pyridyl)methylamines from aldehydes or ketones are known (see, Kuduk, S. D. et al. *Tetrahedron Lett.* 2004, 45, 6641 and Chelucci, G. *Tetrahedron: Asymmetry* 2006, 17, 3163). Aryl- or heteroaryl-cyclopropylamine may be synthesized via titanium alkoxide-mediated reductive cyclopropanation of the corresponding aryl or heteroaryl nitriles with Grignard reagents (Szymoniak, J. et al. *J. Org. Chem.* 2002, 67, 3965, and Bertus, P. et al. *J. Org. Chem.* 2003, 68, 7133) or with zinc reagents (de Meijere, A. et al. *Org. Lett.* 2003, 5, 753). Alternatively, aryl-cyclopropylamines may be synthesized from aryl nitriles or aryl esters via cycloalkylation (e.g., Jonczyk, A. et al. *Org. Prep. Proc.* 1995, 27, 355), followed by conversion of the nitrile or ester group to a carboxylic acid, Curtius rearrangement of the resulting carboxylic acid to a carbamic ester (e.g., Hanano, T. et al. *Bioorg. Med. Chem. Lett.* 2000, 10, 881), and deprotection of the resulting carbamic ester. Intermediated above may be synthesized according to the procedure described in patent application WO 2010036632 and WO 2009134666. Intermediate isocyanates are commercially available, or may be synthesized by methods known in the art. Intermediates and products may be purified by methods known in the art, including column chromatography, HPLC or crystallization. Intermediate aryl and alkyl hydrazine are commercially available, or may be synthesized by methods known in the art.

The methods described below and in the Synthetic Examples section may be used to prepare the compounds of formula I. In the schemes below, $Ar_1$, $Ar_2$, Y and $R_1$-$R_7$, shall have the meanings defined in the detailed description of formula I.

Compounds of formula I where t=1 may be prepared as shown in Scheme I.

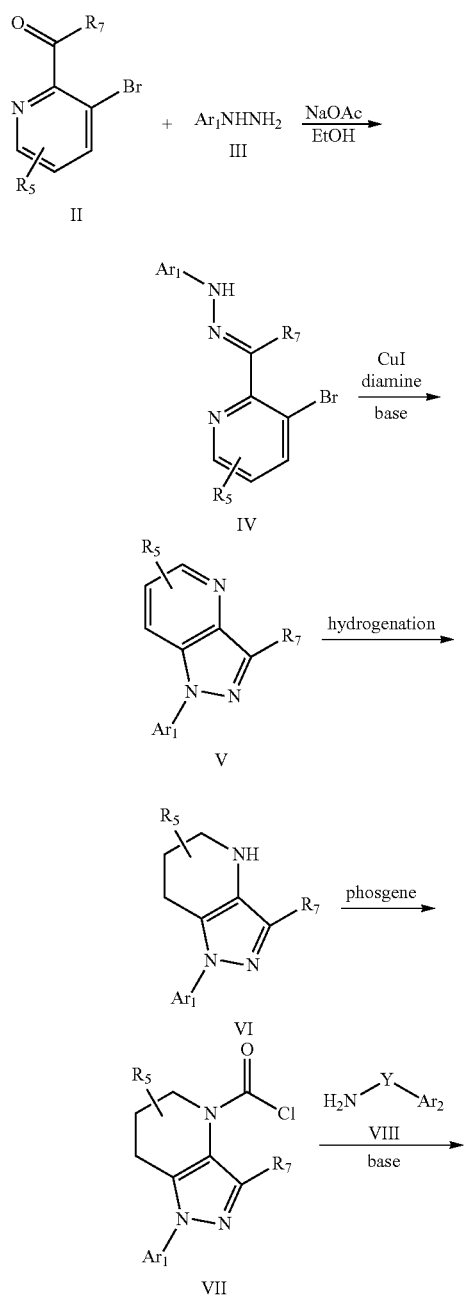

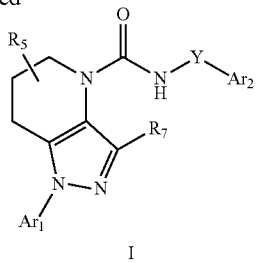

As illustrated above, a hydrazine of the formula III (free base or a suitable salt form such as a hydrochloride salt) bearing $Ar_1$ is reacted with a pyridine II in the presence of sodium acetate in a suitable solvent such as EtOH to provide the hydrazone IV. Reaction of IV with a suitable diamine such as trans-N,N'-dimethylcyclohexane-1,2-diamine in the presence of a copper salt such as CuI and a suitable base such as $K_2CO_3$ and in a suitable solvent such as N-methyl-2-pyrrolidinone (NMP) provides 4-azaindazole V. Hydrogenation of V at a suitable pressure in the presence of a suitable catalyst such as platinum oxide in a suitable solvent such as methanol or EtOH in the presence of a suitable acid such as hydrochloric or sulfuric acid provides a compound of structure VI. Reacting a compound of formula VI with phosgene (in a solution of toluene or a phosgene equivalent such as triphosgene) in a suitable solvent such as dichloromethane (DCM) in the presence of a suitable base such as aqueous $NaHCO_3$ or aqueous $K_2CO_3$ provides a compound of formula VII. Treatment of VII with an amine of formula VIII in the presence of a base such as diisopropylethyl amine (DIPEA) in a suitable solvent such as dimethylformamide (DMF) or DCM provides the desired compound of formula I. Alternatively, compound of formula VI may be reacted with an isocyanate of formula $Ar_1$—Y=N=O in a suitable solvent such as DCM to provide a compound of formula I.

An alternate approach that may be used to obtain compounds of formula I where t=1 is illustrated in Scheme II.

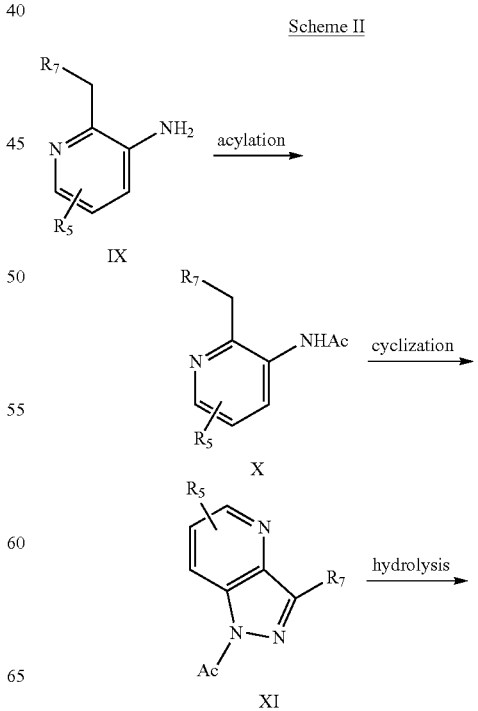

-continued

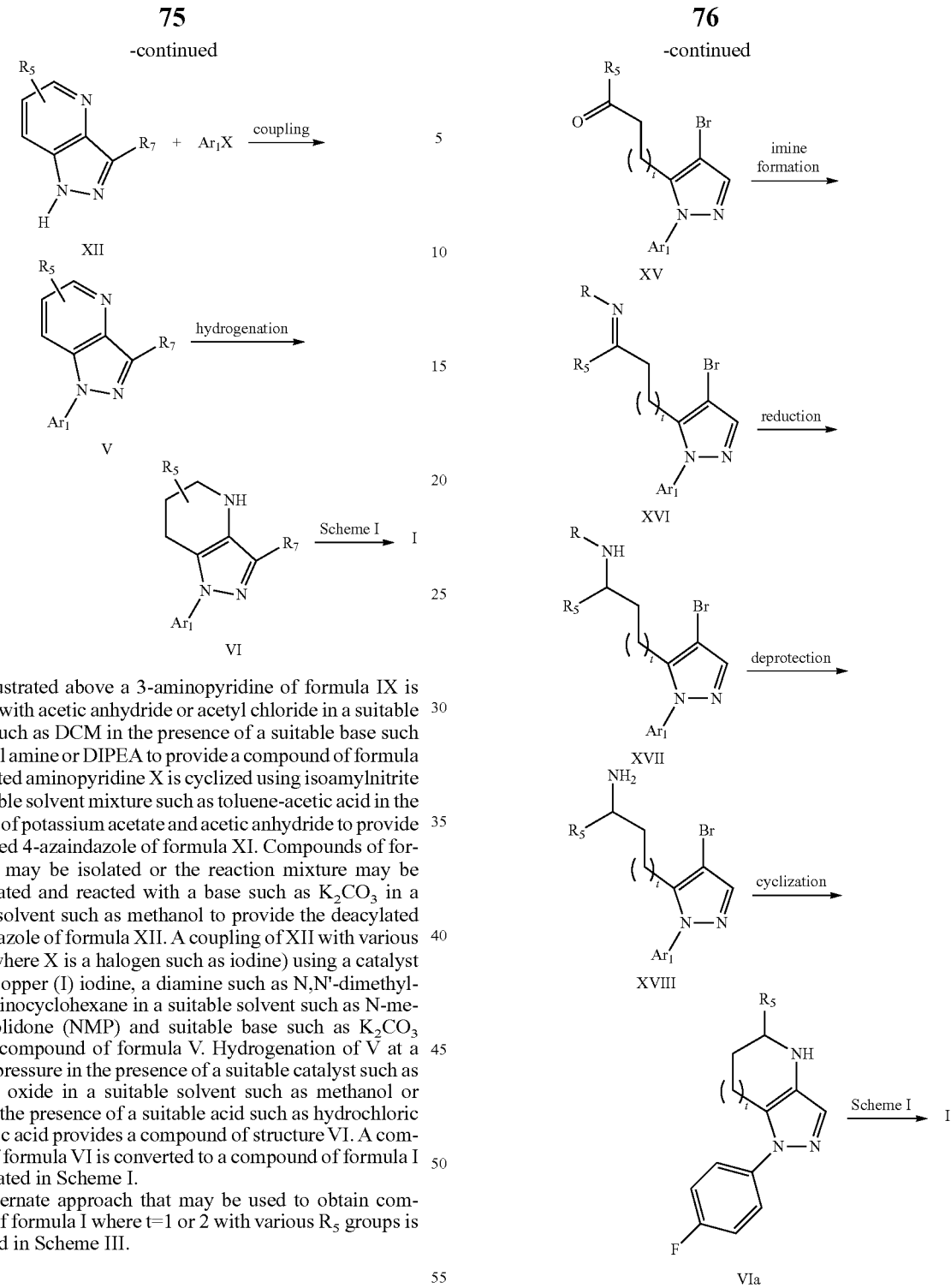

As illustrated above a 3-aminopyridine of formula IX is acylated with acetic anhydride or acetyl chloride in a suitable solvent such as DCM in the presence of a suitable base such as triethyl amine or DIPEA to provide a compound of formula X. Acylated aminopyridine X is cyclized using isoamylnitrite in a suitable solvent mixture such as toluene-acetic acid in the presence of potassium acetate and acetic anhydride to provide an acylated 4-azaindazole of formula XI. Compounds of formula XI may be isolated or the reaction mixture may be concentrated and reacted with a base such as $K_2CO_3$ in a suitable solvent such as methanol to provide the deacylated 4-azaindazole of formula XII. A coupling of XII with various $Ar_1$-X (where X is a halogen such as iodine) using a catalyst such as copper (I) iodine, a diamine such as N,N'-dimethyl-1,2-diaminocyclohexane in a suitable solvent such as N-methylpyrrolidone (NMP) and suitable base such as $K_2CO_3$ afford a compound of formula V. Hydrogenation of V at a suitable pressure in the presence of a suitable catalyst such as platinum oxide in a suitable solvent such as methanol or EtOH in the presence of a suitable acid such as hydrochloric or sulfuric acid provides a compound of structure VI. A compound of formula VI is converted to a compound of formula I as illustrated in Scheme I.

An alternate approach that may be used to obtain compounds of formula I where t=1 or 2 with various $R_5$ groups is illustrated in Scheme III.

Scheme III

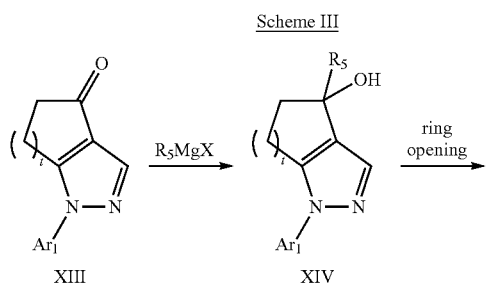

As illustrated above a ketone of formula XIII is reacted with a Grignard reagent where X is a halogen (X=bromine or chlorine) with various $R_5$'s in a suitable solvent such as THF to afford a carbinol of formula XIV. Alternatively, a ketone of formula XIII is reacted with a reducing agent such as sodium borohydride and a suitable acid such as acetic acid in a suitable solvent or solvent mixture such as THF or THF-methanol to afford an aldehyde of formula XIV ($R_5$ is hydrogen). The carbinol of formula XIV is reacted with N-bromoacetamide in the presence of aqueous perchloric acid in a suitable solvent such as THF and water to afford a ketone ($R_5$ is alkyl) or aldehyde ($R_5$ is H) of formula XV. Reacting a compound of the formula XV with an amine such as 2-methyl-2-propane-sulfinamide (R=t-BuS(O)—), a dehydrating agent such as titanium tetraisopropoxide in a suitable solvent such as THF provides an imine of formula XVI. Reacting imine of formula XVI with a suitable reducing agent such as L-Selectride in a suitable solvent such as THF provides a protected amine of formula XVII. Hydrolysis of the protecting group under acidic conditions such as HCl in dioxane in a suitable solvent such as methanol provides an amine of formula XVIII. Cyclization of an amine of formula XVIII using a palladium catalyst such as $Pd(dba)_2$, a ligand such as 2-di-tert-butylphosphino-2',4',6',-triisopropylbiphenyl, and a base such as sodium tert-butoxide in a suitable solvent such as toluene provides an intermediate of formula VIa. A compound of formula VIa is converted to a compound of formula I as illustrated in Scheme I.

Another approach to obtain compounds of formula I with various $R_5$ and $R_6$ groups where t=1 or 2 is illustrated in Scheme IV.

As illustrated above an imine of formula XVI is reacted with a Grignard reagent where X is a halogen (X=bromine or chlorine) with various $R_6$'s in a suitable solvent such as toluene to provide a protected amine of formula XVIIa. Hydrolysis of the protecting group under acidic conditions such as HCl in dioxane in a suitable solvent such as methanol provides an amine of formula XVIIIa. Cyclization of an amine of formula XVIIIa using a palladium catalyst such as $Pd(dba)_2$, a ligand such as 2-di-tert-butylphosphino-2',4',6',-triisopropylbiphenyl, and a base such as sodium tert-butoxide in a suitable solvent such as toluene provides an intermediate of formula VIb. A compound of formula VIb is converted to a compound of formula I as illustrated in Scheme I.

Another approach to obtain compounds of formula I where t=0 with various $R_5$, $R_6$, and $Ar_1$ groups is illustrated in Scheme V.

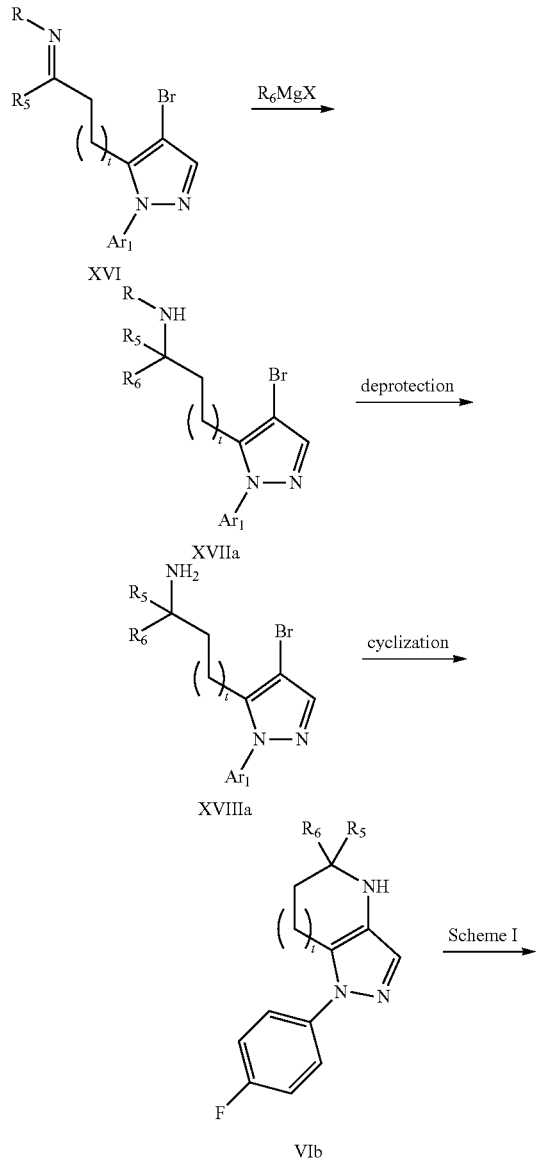

Scheme IV

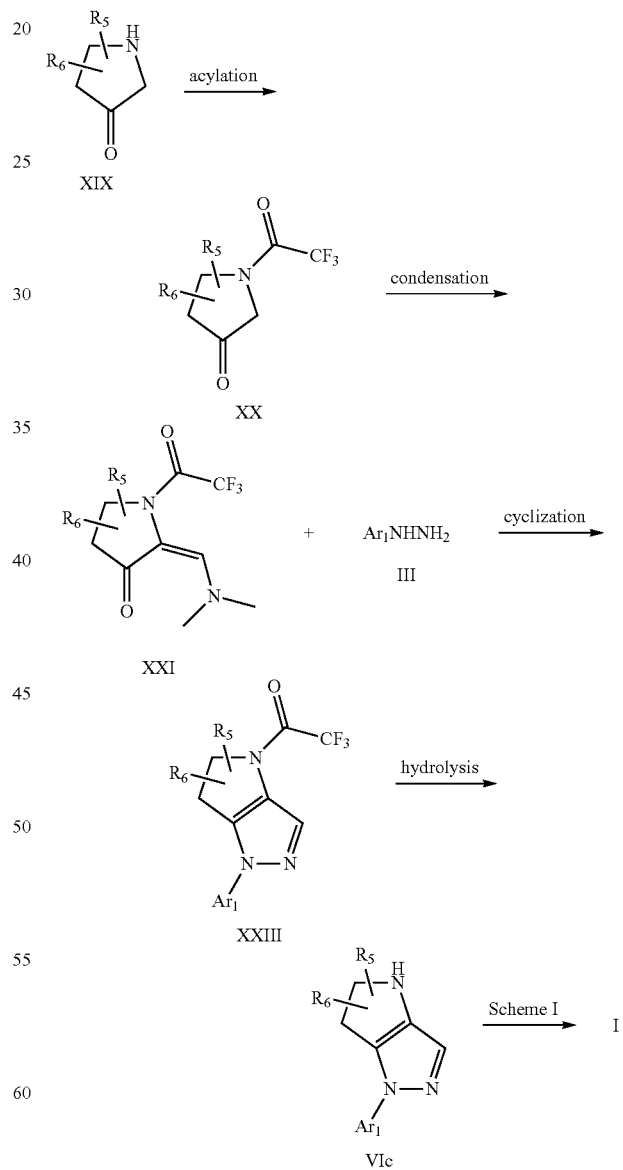

Scheme V

As illustrated above a pyrrolidinone of formula XIX is reacted with trifluoroacetic anhydride to provide an acylated amine of formula XX. Condensation of ketone XX with dimethylformamide dimethyl acetal in a suitable solvent such as dioxane provides the enamine of formula XXI. Reacting enamine XXI with a hydrazine of formula III in a suitable solvent mixture of an alcohol such as methanol or EtOH and water provide a compound of formula XXIII Hydrolysis of XXIII with a suitable base such as $K_2CO_3$ in a suitable solvent such as methanol provides intermediate VIc. A compound of formula VIc is converted to a compound of formula I as illustrated in Scheme I.

The approach in Scheme V may also be used to obtain compounds of formula I where t=1 with various $R_5$, $R_6$, and $Ar_1$ groups, starting from the corresponding piperidinone.

Synthetic Examples

General Methods

All reactions are run at room temperature unless noted otherwise. All reactions are brought to room temperature prior to work up unless noted otherwise. All compounds are characterized by at least one of the following methods: $^1$H NMR, HPLC, HPLC-MS, or melting point.

Retention times (RT) are reported in Table I using one of the following methods:

| HPLC Method | Time (min) | Mobile Phase | | Flow (mL/min) | Column |
|---|---|---|---|---|---|
| | | $H_2O$ (0.1% FA) | $CH_3CN$ (0.1% FA) | | |
| 1 | 0 | 95 | 5 | 2.5 | Agilent Zorbax C18 SB 3.5 um |
| | 1.7 | 5 | 95 | 2.5 | 4.6 × 30 mm cartridge |
| | 2 | 5 | 95 | 2.5 | |
| | 2.1 | 95 | 5 | 2.5 | |
| | 2.3 | 95 | 5 | 2.5 | |
| 2 | 0 | 70 | 30 | 2.5 | Agilent Zorbax C18 SB 3.5 um |
| | 1.7 | 5 | 95 | 2.5 | 4.6 × 30 mm cartridge |
| | 2 | 5 | 95 | 2.5 | |
| | 2.1 | 70 | 30 | 2.5 | |
| | 2.3 | 70 | 30 | 2.5 | |
| 3 | 0 | 99 | 1 | 2.5 | Agilent Zorbax C18 SB 3.5 um |
| | 1.7 | 50 | 50 | 2.5 | 4.6 × 30 mm cartridge |
| | 2 | 5 | 95 | 2.5 | |
| | 2.1 | 5 | 95 | 2.5 | |
| | 2.3 | 99 | 1 | 2.5 | |
| 4 | 0 | 95 | 5 | 1.5 | Agilent Zorbax Eclipse XDB-C8 5 um 4.6 × 150 mm |
| | 7 | 5 | 95 | 1.5 | |
| | 9 | 5 | 95 | 1.5 | |
| | 9.3 | 95 | 5 | 1.5 | |
| | 10 | 95 | 5 | 1.5 | |
| 5 | 0 | 99 | 1 | 2.5 | Agilent Zorbax C18 SB 3.5 um |
| | 1.6 | 80 | 20 | 2.5 | 4.6 × 30 mm cartridge |
| | 1.7 | 5 | 95 | 2.5 | |
| | 2 | 5 | 95 | 2.5 | |
| | 2.1 | 99 | 1 | 2.5 | |
| | 2.3 | 99 | 1 | 2.5 | |
| 6 | 0 | 99 | 1 | 1.5 | Agilent Zorbax Eclipse XDB-C8 5 um 4.6 × 150 mm column |
| | 2 | 80 | 20 | 1.5 | |
| | 7 | 5 | 95 | 1.5 | |
| | 9 | 5 | 95 | 1.5 | |
| | 9.3 | 99 | 1 | 1.5 | |
| | 10 | 99 | 1 | 1.5 | |
| 7 | 0 | 88 | 12 | 1.5 | Agilent SB-C18 1.8 um 3 × 50 mm column |
| | 0.25 | 70 | 30 | 1.5 | |
| | 0.3 | 60 | 40 | 1.5 | |
| | 1.19 | 5 | 95 | 1.5 | |
| | 1.75 | 0 | 100 | 1.5 | |
| 8 | 0 | 60 | 40 | 1.5 | Agilent Eclipse C8 1.8 um 3 × 50 mm column |
| | 1.19 | 15 | 85 | 1.5 | |
| | 1.75 | 0 | 100 | 1.5 | |
| 9 | 0 | 95 | 5 | 1.5 | Agilent SB-AQ 1.8 um 3 × 50 mm column |
| | 0.25 | 50 | 50 | 1.5 | |
| | 0.3 | 70 | 30 | 1.5 | |
| | 1.3 | 10 | 90 | 1.5 | |
| | 1.7 | 0 | 100 | 1.5 | |
| 10 | 0 | 95 | 5 | 1.5 | Agilent SB-C18 1.8 um 3 × 50 mm column |
| | 3.8 | 10 | 90 | 1.5 | |
| | 4.5 | 0 | 100 | 1.5 | |

| HPLC Method | Time (min) | Mobile Phase | | Flow (mL/min) | Column |
|---|---|---|---|---|---|
| | | 95% $H_2O$ + 5% $CH_3CN$ (0.05% Formic Acid) | $CH_3CN$ (0.05% Formic Acid) | | |
| 11 | 0 | 90 | 10 | 0.8 | BEH 2.1 × 50 mm C18, 1.7 um particle diameter |
| | 1.19 | 5 | 95 | 0.8 | |
| | 1.7 | 5 | 95 | 0.8 | |

| | | | | | |
|---|---|---|---|---|---|
| 12 | 0 | 90 | 10 | 0.8 | BEH 2.1 × 50 mm C18, 1.7 um particle diameter |
| | 1.19 | 0 | 100 | 0.8 | |
| | 1.7 | 0 | 100 | 0.8 | |
| 13 | 0 | 95 | 5 | 0.6 | Waters HSS T3 2.1 × 100 mm 18 um column |
| | 4.45 | 0 | 100 | 0.6 | |
| | 5 | 0 | 100 | 0.6 | |
| 14 | 0 | 100 | 0 | 0.6 | Waters HSS T3 2.1 × 100 mm 18 um column |
| | 1 | 100 | 0 | 0.6 | |
| | 4.45 | 0 | 100 | 0.6 | |
| | 5 | 0 | 100 | | |
| 15 | 0 | 90 | 10 | 0.6 | BEH 2.1 × 50 mm C18, 1.7 um particle diameter |
| | 4.45 | 0 | 100 | 0.6 | |
| | 4.58 | 0 | 100 | 0.6 | |

Intermediates

Synthesis of Intermediate A: 1-(4-Fluorophenyl)-4,5,6,7-tetrahydro-1H-pyrazolo[4,3-b]pyridine

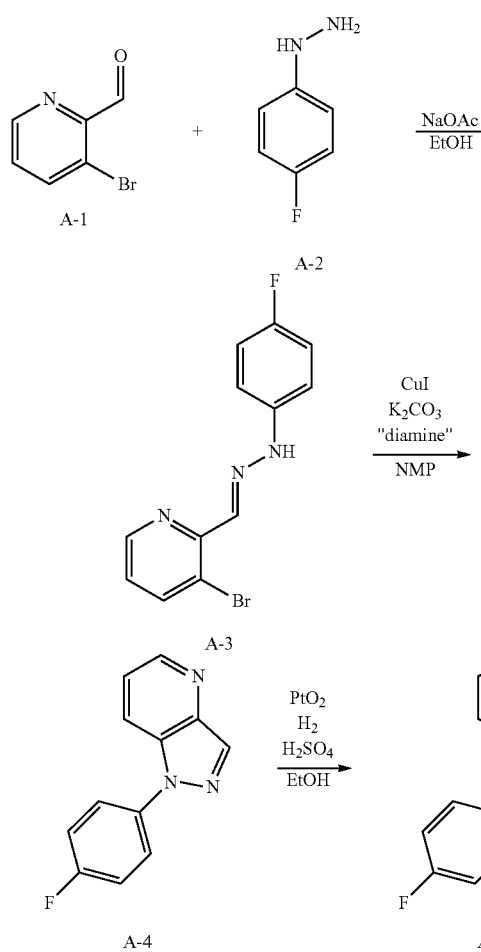

To a solution of A-1 (2.50 g, 13.4 mmol) in EtOH (20 mL) and water (5 mL) is added A-2 HCl salt (2.38 g, 14.7 mmol) and sodium acetate (3.71 g, 27.3 mmol) in water (5 mL). The mixture is warmed to 50° C. After 18 hours, the mixture is diluted with water (50 mL) and the solid is collected by filtration, washing with water and dried to provide A-3.

A mixture of A-3 (3.00 g, 10.2 mmol), CuI (97 mg, 0.51 mmol), N,N'-dimethyl-1,2-diaminocyclohexane (0.6 mL, 0.4 mmol; referred to as "diamine" in schemes throughout), and $K_2CO_3$ (2.82 g, 20.4 mmol) in NMP (100 mL) is warmed at 120° C. for 18 hours. The mixture is diluted with aqueous $NH_4Cl$ (400 mL) and a solid is collected by filtration. The solid is dissolved in EtOAc (100 mL) and water (100 mL). The layers are separated and the aqueous layer is extracted with EtOAc (100 mL). The combined organics are washed with brine (3×100 mL), dried over $Na_2SO_4$, filtered and concentrated. The crude product is purified by silica gel chromatography eluting with a gradient of 0-100% MeOH in DCM to provide A-4.

A solution of A-4 (1.0 g, 4.7 mmol) in 50 mL absolute EtOH is degassed and filled with argon. Platinum oxide (200 mg, 0.88 mmol) is added under a stream of argon followed by sulfuric acid (0.25 mL). The vessel is evacuated and filled $H_2$ via a balloon. The mixture is stirred for 18 hours. The reaction vessel is evacuated and purged with argon and the mixture is filtered through filter agent. The filtrate is diluted with 2M NaOH until basic and concentrated. The aqueous solution is extracted with EtOAc (4×15 mL), washed with $NaHCO_3$ and brine, dried over $Na_2SO_4$ and concentrated. The crude material is dissolved in EtOAc (20 mL) and passed through a pad of silica using 70% EtOAc/hexanes (150 mL). The filtrate is concentrated to provide the title compound.

The following intermediates are synthesized in similar fashion using the appropriate hydrazine component:

| Intermediate | Structure |
|---|---|
| B | 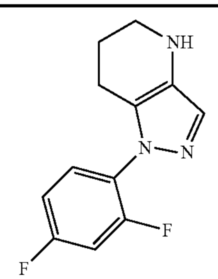 |
| C | 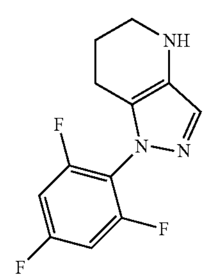 [SMILES: Fc1cc(F)c(-n2ncc3c2CCCN3)c(F)c1] |

Synthesis of Intermediate D: 1-(4-Fluorophenyl)-3-methyl-4,5,6,7-tetrahydro-1H-pyrazolo[4,3-b]pyridine

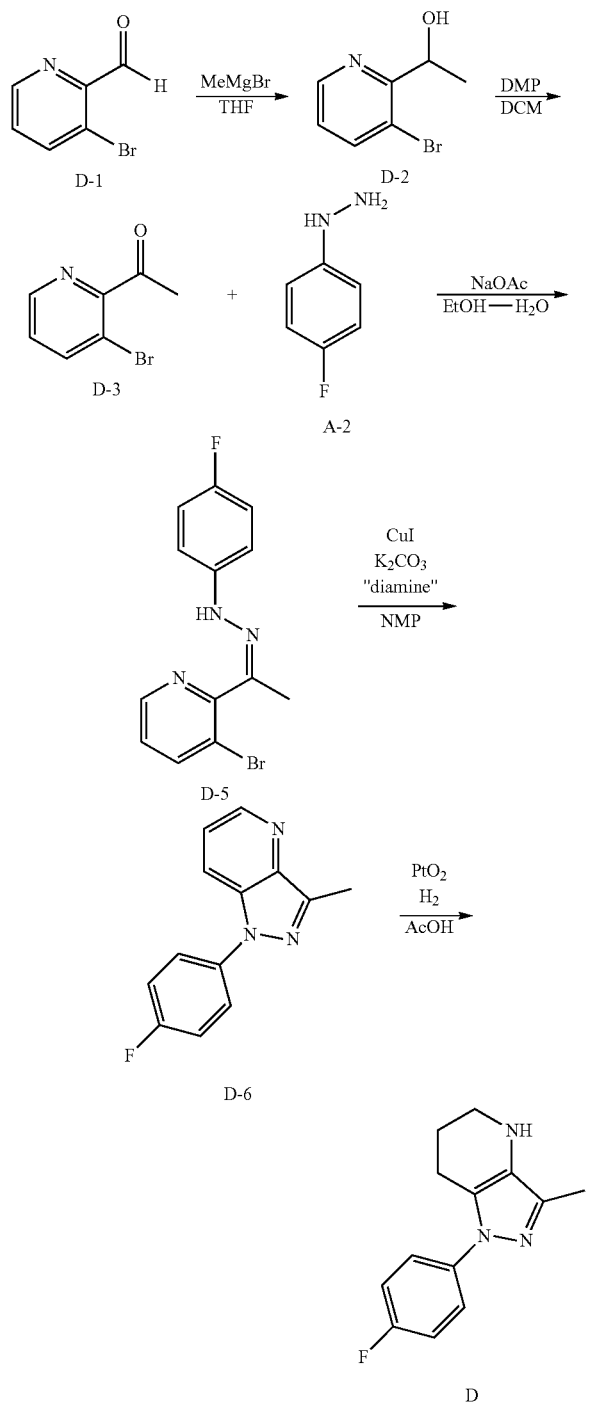

To a chilled (−78° C.) solution of D-1 (10 g, 54 mmol) in THF (150 mL) is added a solution of 3M MeMgBr in diethyl ether (35.8 mL, 108 mmol). The solution is stirred for 30 minutes at −78° C. and is allowed to warm to room temperature over 30 minutes. The reaction mixture is quenched with saturated NH$_4$Cl and is extracted with EtOAc (3×100 mL). The combined organic layers are washed with brine (100 mL), dried over Na$_2$SO$_4$, filtered and concentrated to provide D-2.

To a chilled (0° C.) solution of D-2 (12 g, 59 mmol) in DCM (300 mL) is added Dess-Martin Periodinane (DMP) (50.3 g, 118.8 mmol). The mixture is warmed to room temperature. After 14 hours, the mixture is concentrated and purified using silica column chromatography (5% EtOAc/Petroleum ether) to provide D-3.

To a stirred solution of D-3 (10 g, 50 mmol) in EtOH (80 mL) and water (20 mL) is added A-2 HCl salt (8.9 g, 55 mmol) and NaOAc (12.6 g, 150 mmol) in water (30 mL). The reaction mixture is warmed at 60° C. After 2 hours, the reaction mixture is diluted with water (500 mL) and extracted with EtOAc (3×200 mL). Combined organic layers are washed with brine (500 mL), dried over Na$_2$SO$_4$, filtered and concentrated. The crude material is purified by silica gel chromatography eluting with 15% EtOAc in petroleum ether to provide D-5.

To a solution of D-5 (13 g, 42.2 mmol) in NMP (500 mL) is added CuI (800 mg, 4.21 mmol), K$_2$CO$_3$ (11.66 g, 84.37 mmol) and N,N'-dimethyl-1,2-diaminocyclohexane (0.6 g, 4.2 mmol) and the mixture is warmed at 120° C. After 3 hours, mixture is quenched with saturated aqueous NH$_4$Cl and extracted with EtOAc (3×300 mL). The combined organic layers are washed with brine (400 mL), dried over Na$_2$SO$_4$, filtered and concentrated. The crude material is purified by silica gel chromatography eluting with 20% EtOAc/petroleum ether to provide D-6.

To a stirred solution of D-6 (2.0 g, 8.8 mmol) in AcOH (40 mL) is added platinum oxide (0.78 g, 2.6 mmol) and the mixture is placed under 1 atmosphere of hydrogen. After 3 hours, the PtO$_2$ is filtered through filter agent washing with methanol (2×30 mL). The filtrate is concentrated under reduced pressure and co-distilled with hexane (2×20 mL) to remove the traces of AcOH. The crude product is purified by silica gel chromatography eluting with 60% EtOAc-petroleum ether to provide the title compound.

Synthesis of Intermediate E: 1-(4-Fluorophenyl)-1,4,5,6-tetrahydro-pyrrolo[3,2-c]pyrazole

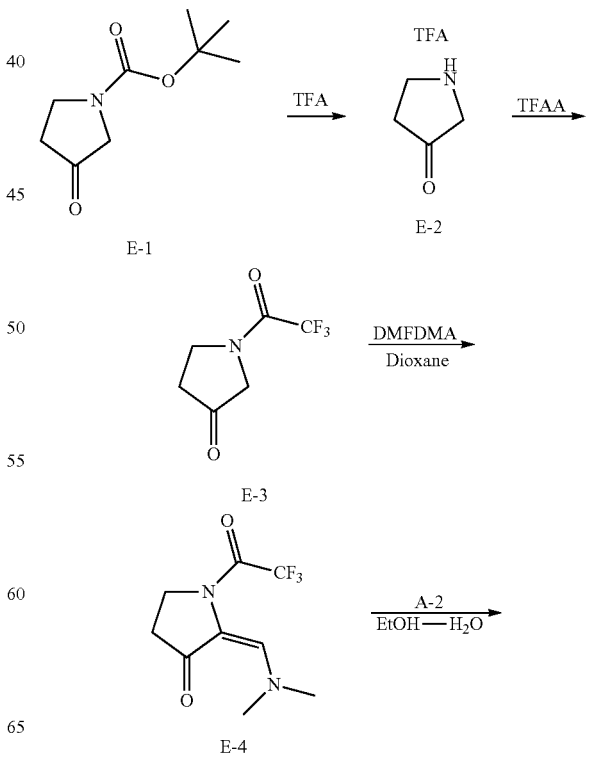

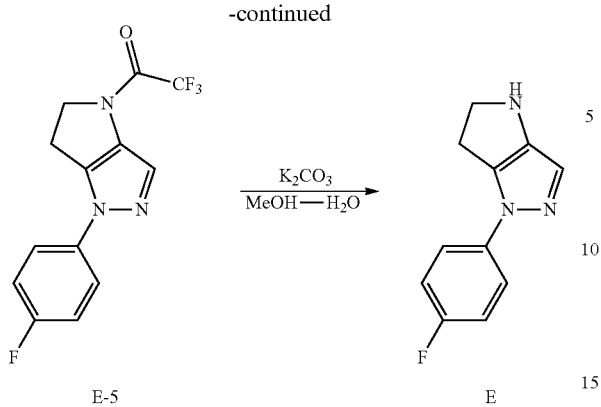

A solution of E-1 (3.6 g, 19 mmol) in trifluoroacetic acid (TFA) (10 mL) is stirred at room temperature for 1 hour. TFA is removed under reduced pressure. DCM (50 mL) is added and removed under reduced pressure two times to provide E-2.

To E-2 (3.9 g, 20 mmol) is added trifluoroacetic anhydride (TFAA) (20 mL). After 17 hours, the mixture is concentrated and twice diluted with DCM (50 mL) and concentrated to provide E-3.

To a solution of E-3 (3.6 g, 20 mmol) in dioxane (20 mL) is added N,N-dimethylormamide dimethyl acetal (DMFDMA) (5.6 mL, 39.4 mmol) and the mixture is warmed at 100° C. After 1 hour, the solvent is concentrated and the residue is purified by silica gel chromatography using a gradient of 20-100% EtAOc in heptane to provide E-4.

A-2 (690 mg, 4.2 mmol) is added to E-4 (950 mg, 4.0 mmol) in EtOH (10 mL) and H₂O (1 mL) and warmed to 100° C. After 1.5 hours, the mixture is quenched with saturated NH₄Cl, extracted with EtOAc, washed with brine, dried over Na₂SO₄, filtered and concentrated. The residue is purified by silica gel chromatography using a gradient of 0-40% EtOAc in heptane to provide impure E-5 which is further purified by reversed phase-HPLC using a gradient of 20-95% MeCN in H₂O to provide E-5.

To a solution of E-5 (200 mg, 0.7 mmol) in MeOH (10 mL) is added a solution of K₂CO₃ (370 mg, 2.7 mmol) in H₂O (3 mL). After 2 hours, the mixture is concentrated and extracted with EtOAc. The organic layer is dried over Na₂SO₄, filtered, and concentrated to provide the title compound.

Synthesis of Intermediate F: 1-(4-Fluorophenyl)-5-methyl-1,4,5,6-tetrahydro-pyrrolo[3,2-c]pyrazole

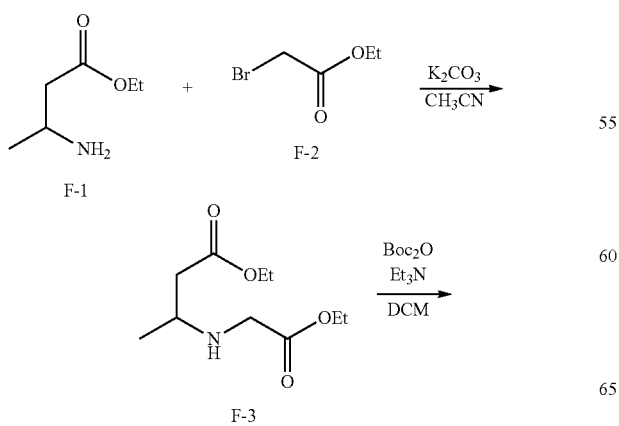

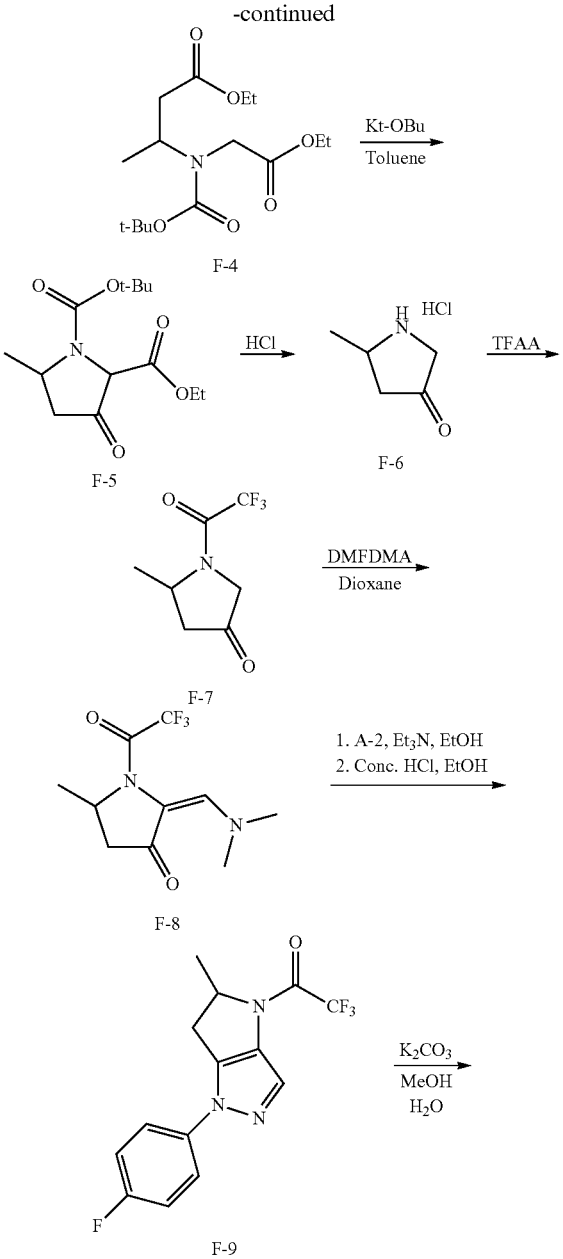

To a solution of F-1 (10 g, 76 mmol) and F-2 (8.5 mL, 76 mmol) in acetonitrile (300 mL) is added K₂CO₃ (30 g, 217 mmol). After 5 hours, EtOAc (200 mL) is added and the organic layer is washed with water (2×100 mL), brine (2×50 mL), dried over Na₂SO₄, filtered, and concentrated. The residue is purified by silica gel chromatography using a solvent gradient of 0-4% MeOH in DCM to provide F-3.

To a chilled (0° C.) solution of F-3 (11.0 g, 50.6 mmol) in DCM is added triethylamine (15.0 mL, 104 mmol) and Boc₂O (18.5 mL, 76.4 mmol). The mixture is warmed to room temperature. After 12 hours, the reaction is diluted with DCM (200 mL) and washed with water (2×100 mL). The organic layer is dried over Na₂SO₄, filtered, and concentrated. The residue is purified by silica gel chromatography using a solvent gradient of 0-20% EtOAc in hexanes to provide F-4.

To a chilled (0° C.) solution of F-4 (13 g, 41 mmol) in dry toluene (175 mL) is added KtOBu (11.5 g, 103 mmol) and the reaction is warmed to room temperature. After 30 minutes, acetic acid (5 mL) is added followed by aqueous sodium monohydrophospate (27 g in 100 mL). The mixture is extracted with chloroform (2×400 mL), washed with phosphate buffer (pH ~7, 2×200 mL), dried over Na₂SO₄, filtered and concentrated. The mixture is dissolved in toluene (200 mL), washed with carbonate (pH ~9.5) buffer (10×200 mL) and dried over Na₂SO₄ filtered and concentrated. The residue is purified by silica gel chromatography using a gradient of 0-15% EtOAc in hexanes) to provide F-5.

To F-5 (2.0 g, 7.4 mmol) is added an aqueous solution of 4N HCl (22 mL, 88 mmol). After 4 hours, the mixture is concentrated provide F-6.

To F-6 (1 g, 7.4 mmol) is added TFAA (9.3 g, 44.2 mmol). After 1 hour, the mixture is concentrated to provide F-7.

To a solution of F-7 (1.4 g, 7.4 mmol) in dioxane (10 mL) is added DMFDMA (2.1 mL, 15 mmol) and the mixture is warmed at 100° C. After 1.5 hours, the mixture is concentrated and purified by silica gel chromatography using a gradient of 20-70% EtAOc in heptane to provide F-8.

To a solution of A-2 (310 mg, 1.9 mmol) in EtOH (16 mL) is added Et₃N (0.3 mL, 1.9 mmol) and F-8 (460 mg, 1.8 mmol). After 20 minutes, 12N HCl (0.2 mL, 2.6 mmol) is added and the mixture is warmed at 100° C. After 1 hour, the mixture is concentrated and purified by silica gel chromatography using a gradient of 0-15% EtOAc in heptane to provide F-9.

To a solution of F-9 (200 mg, 0.6 mmol) in MeOH (10 mL) is added a solution of K₂CO₃ (340 mg, 2.5 mmol) in H₂O (3 mL). After 1 hour, the MeOH is concentrated and the aqueous layer is extracted with EtOAc, dried over Na₂SO₄, filtered, and concentrated to provide the title compound.

Synthesis of Intermediate G: 1-Cyclohexyl-4,5,6,7-tetrahydro-1H-pyrazolo[4,3-b]pyridine

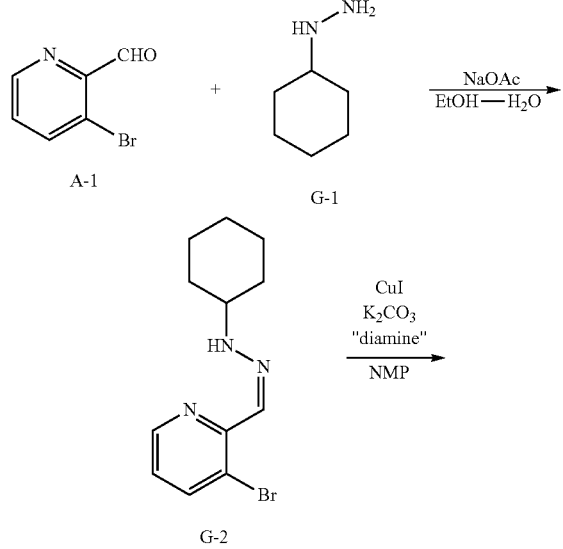

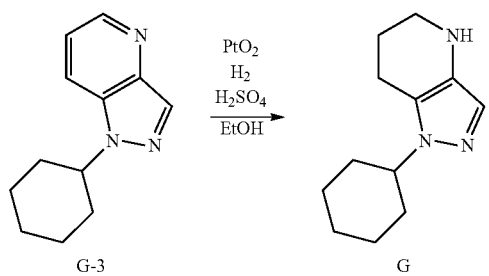

To a solution of A-1 (1.0 g, 5.4 mmol) in EtOH (10 mL) and water (2.5 mL) is added a solution of G-1 HCl salt (0.89 g, 5.9 mmol) and sodium acetate (1.46 g, 5.91 mmol) in 5 mL of water and the mixture is warmed at 50° C. After 18 hours, the mixture is diluted with water (50 mL) and extracted with EtOAc (2×100 mL). The combined organic layers are washed with brine (2×100 mL), dried over Na₂SO₄, filtered and concentrated to provide G-2.

A mixture of G-2 (1.56 g, 4.73 mmol), CuI (90 mg, 0.5 mmol), N,N-dimethyl-1,2-diaminocyclohexane (0.01 mL, 0.1 mmol), and K₂CO₃ (1.3 g, 9.5 mmol) in NMP (10 mL) is warmed at 120° C. After 3 hours, the mixture is diluted with aqueous NH₄Cl (400 mL) and extracted with EtOAc (2×100 mL). The combined organic layers are washed with brine (2×100 mL), dried over Na₂SO₄, filtered and concentrated. The crude product is purified by silica gel chromatography using a gradient of 0-50% EtOAc in heptane to provide G-3.

A solution of G-3 (450 mg, 2.2 mmol) in absolute EtOH (10 mL) is degassed and filled with argon. Platinum oxide (100 mg, 0.5 mmol) is added under a stream of argon followed by sulfuric acid (0.25 mL). The vessel is evacuated and filled with H₂ via a balloon. After 18 hours, the mixture is filtered through filter agent and concentrated. The crude material is dissolved in EtOAc (100 mL) and washed with saturated NaHCO₃. The layers are separated and the organic layer is dried over Na₂SO₄ and concentrated to provide the title compound.

The following intermediate is synthesized in similar fashion as described for intermediate G using the appropriate hydrazine component:

| Intermediate | Structure |
|---|---|
| H | 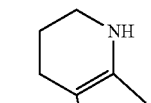 |

The following intermediate is synthesized in similar fashion using the appropriate hydrazine component and the final hydrogenation step is performed on a continuous flow hydrogenation apparatus using a 10% Pt on carbon cartridge at 50 bars and 60° C. at a flow rate of 3 mL/minute:

| Intermediate | Structure |
|---|---|
| I | 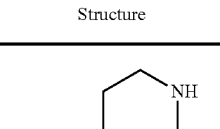 |

Synthesis of Intermediate J: 1-(4-Fluorophenyl)-5-methyl-4,5,6,7-tetrahydro-1H-pyrazolo[4,3-b]pyridine

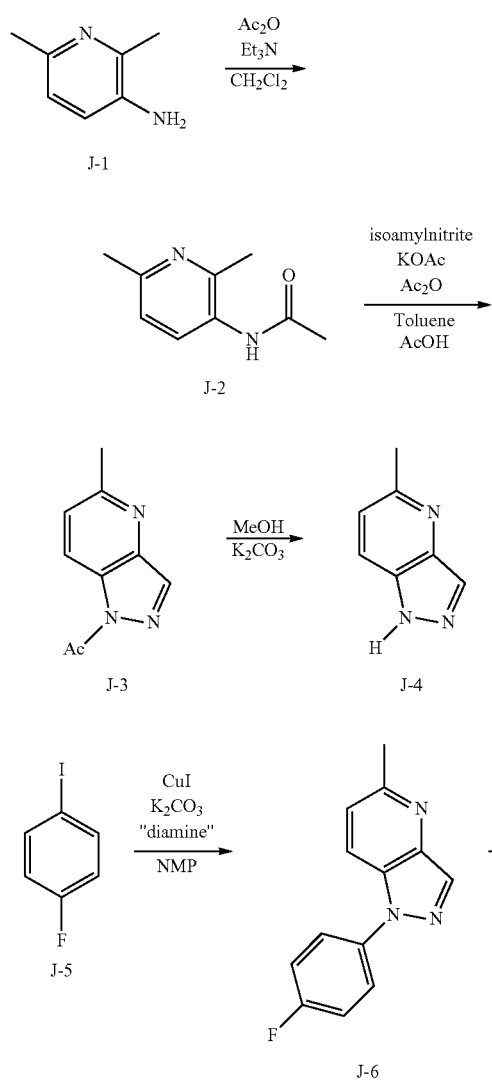

To a solution of J-1 (5.00 g, 40.9 mmol) in DCM (25 mL) is added acetic anhydride (5.00 mL, 51.8 mmol) followed by triethylamine (6.50 mL, 46.7 mmol). After 2 hours, the mixture is concentrated and diluted with water, made basic with sodium carbonate, and extracted with EtOAc (8×30 mL). The combined organic layers are dried over magnesium sulfate, filtered and concentrated to provide J-2.

To a solution of J-2 (5.25 g, 31.9 mmol) in toluene (80 mL) is added acetic anhydride (10.0 mL, 105.7 mmol), acetic acid (10.0 mL, 174.7 mmol) and potassium acetate (5.50 g, 601.7 mmol). The mixture is warmed to reflux and amyl nitrite (5.20 mL, 37.9 mmol) in toluene (16 mL) is added. After 2 hours, the reaction is poured into water, made basic with $NaHCO_3$ and extracted with EtOAc (3×50 mL). The combined organic layers are washed with brine, dried over magnesium sulfate, filtered and concentrated. The crude material is purified on silica gel eluting with EtOAc-hexanes (25:75) followed by crystallized from ether-hexanes to provide J-3.

J-3 (1.50 g, 8.56 mmol) and $K_2CO_3$ (1.50 g, 10.9 mmol) in methanol (20 mL) is warmed at reflux for 5 minutes. The mixture is filtered and concentrated to provide J-4.

J-4 (1.10 g, 8.26 mmol), CuI (980.0 mg, 5.15 mmol), $K_2CO_3$ (2.75 g, 19.9 mmol), N,N-dimethyl-1,2-diaminocyclohexane (150.0 µL, 0.95 mmol) and 4-fluoroiodobenzene (2.40 g, 10.8 mmol) in DMF (13 mL) is warmed at 130° C. in a microwave reactor. After 1 hour, the reaction is diluted with saturated aqueous $NH_4Cl$ (50 mL) and then $NaHCO_3$ is added and the mixture is extracted with EtOAc (3×50 mL). The combined organic layers are washed with saturated aqueous $NH_4Cl$ (3×40 mL), dried over magnesium sulfate, filtered and concentrated. The residue is purified by silica gel chromatography eluting with a gradient of 0-50% EtOAc in hexanes and crystallized from ether-hexanes to provide J-6.

A solution of J-6 in methanol and 1N aqueous HCl is hydrogenated on a continuous flow hydrogenation apparatus using a 5% Pt on carbon catalyst cartridge at 50 bars, 50° C. and at a flow rated of 1 mL/minute. The mixture is diluted with water and EtOAc and made basic with $NaHCO_3$. The mixture is extracted with DCM (3×30 mL). The combined organic layers are washed with brine (3×15 mL), dried over $Na_2SO_4$, filtered and concentrated to provide the title compound.

1st Eluting Enantiomer J-A
2nd Eluting Enantiomer J-B

Racemic material is resolved using an AD column (50×500 mm) under the condition: 2-propanol (i-PA) in heptane, 75 mL/minute to provide first J-A and then J-B.

Synthesis of Intermediate K: 1-(4-Fluorophenyl)-5-trifluoromethyl-4,5,6,7-tetrahydro-1H-pyrazolo[4,3-b]pyridine

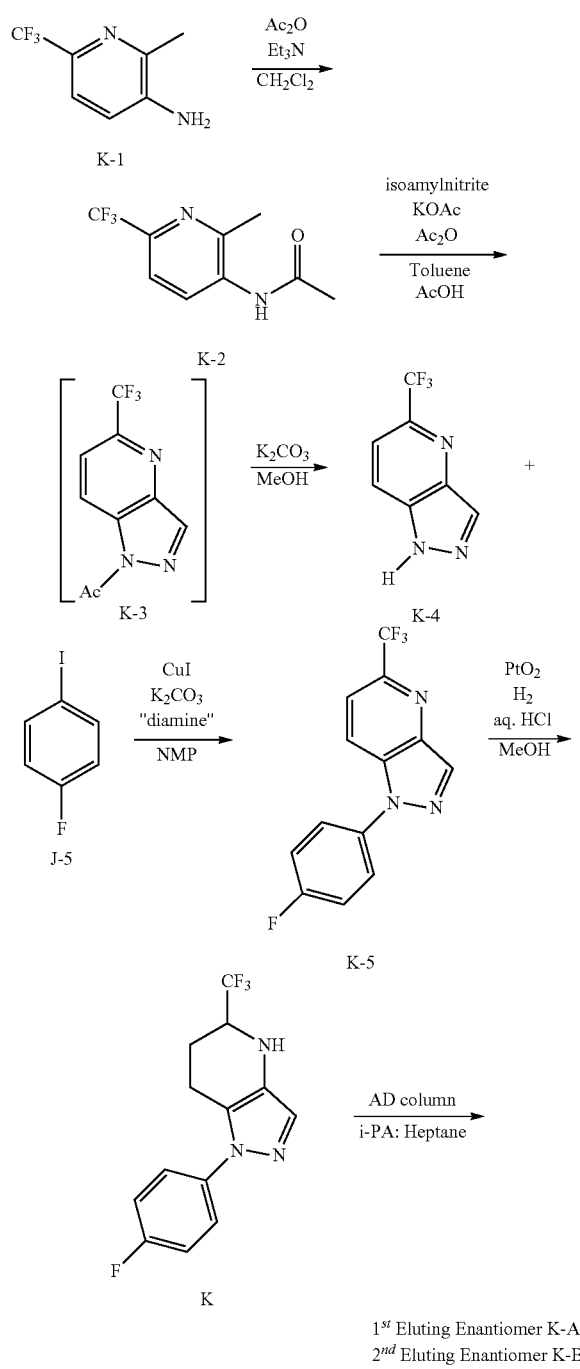

1st Eluting Enantiomer K-A
2nd Eluting Enantiomer K-B

To a solution of K-1 (5.00 g, 28.4 mmol) in DCM (25 mL) is added acetic anhydride (3.30 mL, 34.2 mmol) followed by DIPEA (5.6 mL, 32.2 mmol) and DMAP (25.0 mg, 0.20 mmol). After 6 days, the reaction is concentrated and diluted with water, made basic with NaHCO$_3$, and extracted with EtOAc (3×50 mL). The combined organic layers are washed with brine (2×40 mL), dried over magnesium sulfate, filtered and concentrated. The crude material is purified by silica gel chromatography eluting with DCM-heptane (1:1) and then ethyl acetate. Mixed fractions are purified by silica gel chromatography eluting with EtOAc-heptane (1:9, then 2:8, then 100:0) to provide K-2.

To a solution of K-2 (3.2 g, 14.7 mmol) in toluene (60 mL) is added acetic anhydride (4.20 mL, 44.4 mmol), acetic acid (4.20 mL, 73.4 mmol) and potassium acetate (2880 mg, 29.34 mmol). The mixture is warmed at reflux and isoamyl nitrite (2520.0 μL, 18.38 mmol) is added. After 1 hour, the reaction is concentrated and diluted with methanol (60 mL) and K$_2$CO$_3$ (15.0 g, 108 mmol) is added and the mixture is warmed at reflux. After 1 hour, the reaction is poured into water and concentrated and the solid is collected by filtration. The filter cake is dissolved in 10% EtOAc-DCM dried over magnesium sulfate, and passed through a pad of silica gel eluting with first DCM and then a gradient of 10-50% EtOAc in DCM to provide K-4.

A solution of K-4 (2.60 g, 13.9 mmol), CuI (1.40 g, 7.35 mmol), K$_2$CO$_3$ (4.00 g, 28.9 mmol), N,N-dimethyl-1,2-diaminocyclohexane (188.0 μL, 1.19 mmol) and J-5 (2.20 mL, 19.1 mmol) in DMF (28 mL) is warmed at 140° C. in the microwave reactor. After 1.5 hours, the reaction is diluted with saturated aqueous NH$_4$Cl (50 mL) and then NaHCO$_3$ is added and the mixture is diluted with EtOAc (100 mL) and stirred for 1 hour. The aqueous layer is separated and extracted with EtOAc (2×50 mL). The combined organic layers are washed with saturated aqueous NH$_4$Cl (2×30 mL), brine (3×30 mL), dried over magnesium sulfate, filtered and concentrated. The residue is purified on silica gel eluting with DCM-heptane (4:6, then 1:1, then 100:0) and is then crystallized from ether-heptane to provide K-5.

A mixture of K-5 (13.2 g, 46.9 mmol) in methanol (120 mL) and 4N HCl in dioxane (15.0 mL, 60 mmol) is hydrogenated with 10% Pt on carbon (6 g) at 50° C. and between 300-350 psi. After 3 hours, the reaction is filtered and concentrated. The residue is made basic with saturated aqueous NaHCO$_3$ (pH ~7) and extracted with EtOAc (2×). The combined organic layers are washed with brine, dried over Na$_2$SO$_4$ and concentrated. The residue is purified on silica gel eluting with a gradient of 10-40% EtOAc in heptane to provide the title compound.

Racemic material is resolved using an AD column (50×500 mm) under the condition: 35% 2-propanol in heptane, 75 mL/minute to provide first K-A and then K-B.

Synthesis of Intermediate L: 1-Cyclohexyl-4,5,6,7-tetrahydro-1H-pyrazolo[4,3-b]pyridine

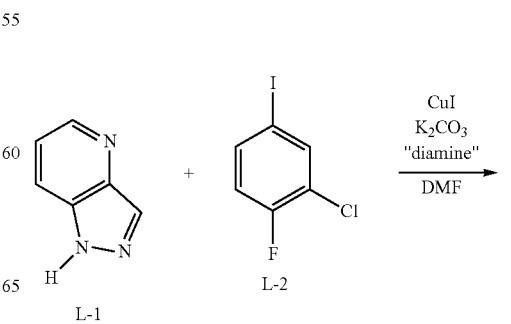

93

-continued

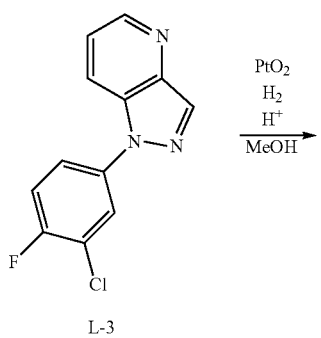

94

Synthesis of Intermediate N: 1-(6-Fluoropyridin-3-yl)-5-methyl-4,5,6,7-tetrahydro-1H-pyrazolo[4,3-b]pyridine

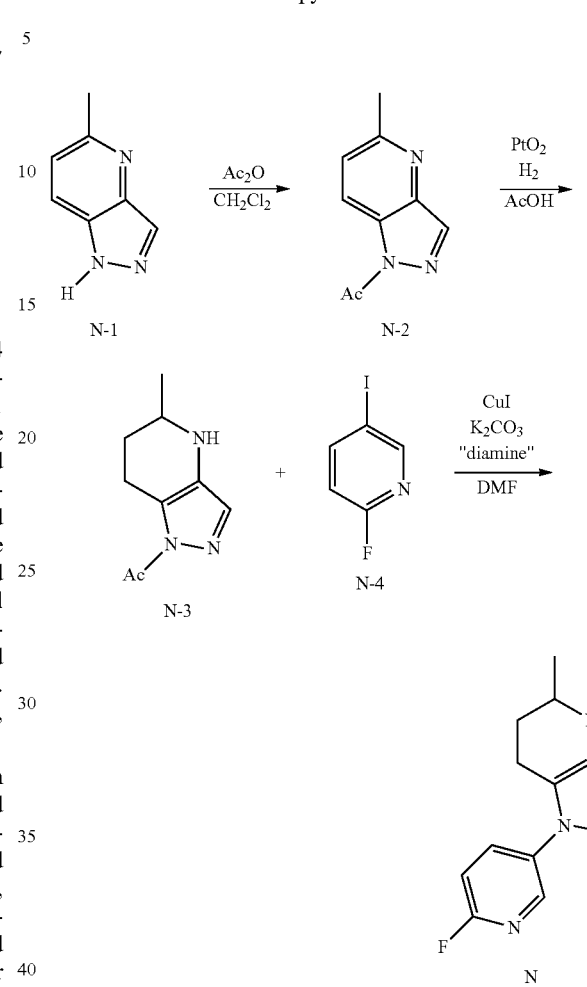

A solution of L-1 (1.0 g, 8.4 mmol), CuI (960 mg, 5.4 mmol), $K_2CO_3$ (2.78 g, 20.2 mmol), N,N'-dimethyl-1,2-diaminocyclohexane (0.130 mL, 0.84 mmol), and L-2 (2.8 g, 11 mmol) in 13 mL of DMF is warmed at 130° C. in a microwave reactor. After 1 hour, the reaction is diluted with saturated aqueous $NH_4Cl$ (50 mL) and $NaHCO_3$ is added and the mixture is stirred for 30 minutes. EtOAc (200 mL) is added and the mixture is stirred overnight at room temperature. The mixture is extracted with EtOAc (3×50 mL). The combined organic layers are washed with saturated aqueous $NH_4Cl$ (3×40 mL), dried over magnesium sulfate, filtered and concentrated. The residue is dissolved in 15 mL methanol and stirred at 80° C. for 30 minutes and allowed to cool for 1 hour. The material is collected by filtration, washed with hexanes, and dried to provide L-3.

A mixture of L-3 (1.2 g, 5.1 mmol) and $PtO_2$ (250 mg) in methanol (50 mL) and 4N HCl (1.45 mL) in dioxane is placed under one atmosphere of hydrogen. After 64 hours, the mixture is filtered through filter agent washing with EtOAc and concentrated. The residue is dissolved in DCM (200 mL), diluted with water and $NaHCO_3$, and concentrated. The aqueous layer is extracted with DCM (3×40 mL). The combined organic layers are washed with brine (3×15 mL), dried over magnesium sulfate, filtered and concentrated. The crude material is purified by silica gel chromatography eluting using a gradient of 0-5% methanol in DCM to provide the title compound.

The following intermediate is synthesized in similar fashion starting with 5-methyl-1H-pyrazolo[4,3-b]pyridine and coupling with 1-chloro-4-iodo-benzene:

| Intermediate | Structure |
|---|---|
| M | (structure shown) |

To a solution of N-1 (1 g, 7 mmol) in DCM (5 mL) is added acetic anhydride (1.2 g, 0.01 mol). After 16 hours, the mixture is concentrated and purified by silica gel chromatography eluting with a gradient of 0-70% EtOAc in heptane to provide N-2.

A solution of N-2 (1.4 g, 8.0 mmol) and platinum oxide (150 mg) in acetic acid (10 mL) is placed under an atmosphere of $H_2$. After 2 days, the mixture is filtered through filter agent washing with EtOAc and concentrated. The crude material is purified by silica gel chromatography eluting with a gradient of 0-10% methanol in DCM to provide N-3.

A solution of N-3 (50 mg, 0.36 mmol), CuI (69 mg, 0.36 mmol), $K_2CO_3$ (0.12 g, 0.87 mmol), N,N-dimethyl-1,2-diaminocyclohexane (2.0 µL, 0.01 mmol) and N-4 (0.08 g, 0.36 mmol) in DMF (2 mL) is warmed at 130° C. in the microwave for 60 minutes. The reaction mixture is treated with 20 mL of saturated aqueous $NH_4Cl$ and extracted with EtOAc (3×20 mL) and the combined organics are washed with $NH_4Cl$ (2×20 mL), dried over $Na_2SO_4$, filtered and concentrated. The crude material is purified by silica gel chromatography eluting with a gradient of 40-100% EtOAc in heptane to provide the title compound.

Synthesis of Intermediate O:1-(4-Fluorophenyl)-1,4,5,6,7,8-hexahydro-1,2,4-triaza-azulene

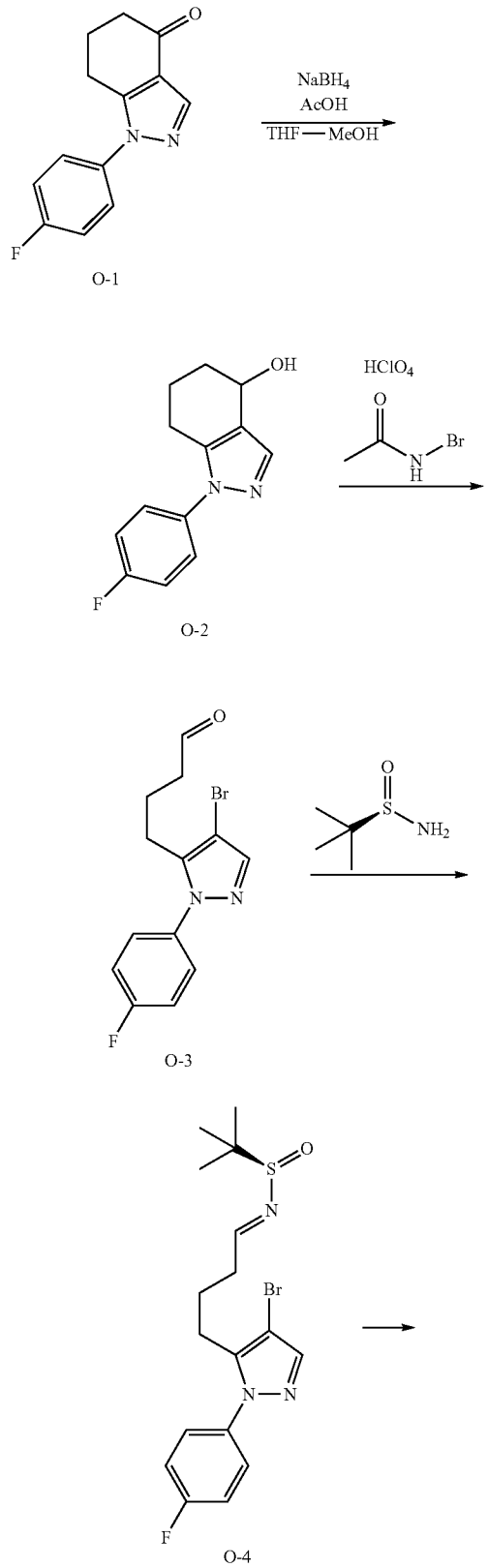

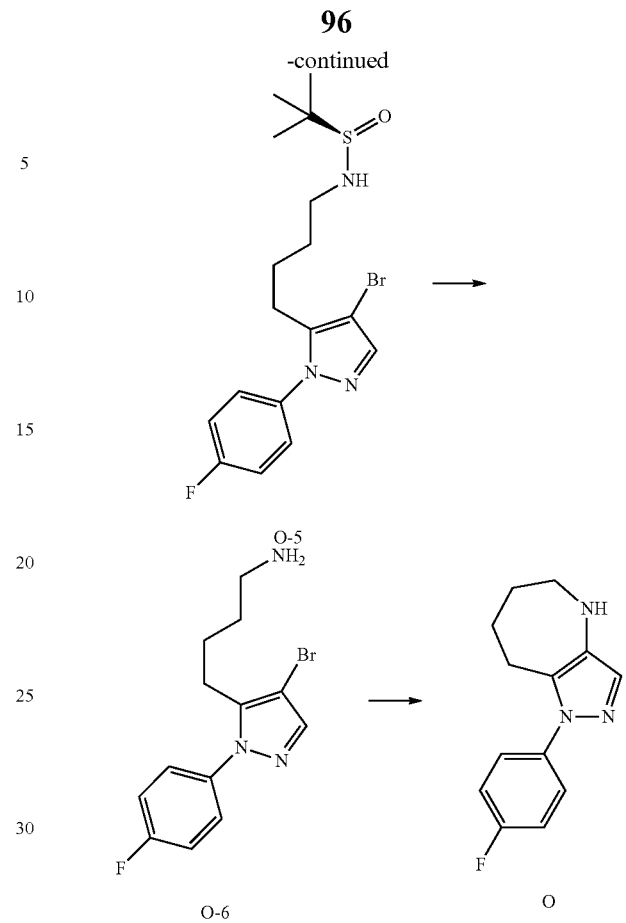

The starting material ketone O-1 is synthesized as described in *J. Org. Chem.*, 1987, 52, 4384 using 4-fluorophenylhydrazine.

O-1 (6 g, 30 mmol) is dissolved in THF (5.5 mL) and methanol (16 mL). Sodium borohydride (4.9 g, 130 mmol) is added followed by glacial acetic acid (1.32 mL). After 18 hours, the mixture is concentrated, diluted with brine (250 mL) and extracted with EtOAc (3×100 mL). The combined organics layers are washed with water, dried over $Na_2SO_4$ and concentrated to provide O-2.

To a chilled (0° C.) solution of O-2 (5.0 g, 22 mmol) in THF (150 mL) and water (50 mL) is slowly added a solution of 1M aqueous $HClO_4$ (21.5 mL, 21.5 mmol) followed by N-bromoacetamide (2.97 g, 21.5 mmol). After 2 hours, the mixture is concentrated and diluted with DCM (150 mL) and $H_2O$ (100 mL). The organic layer is separated and washed with brine (150 mL), dried over $Na_2SO_4$, filtered, and concentrated. The crude material is purified by silica gel chromatography using a gradient of 0-100% EtOAc in heptane to provide O-3.

Ti(OiPr)$_4$ (16.8 mL, 56.6 mmol) is added to a solution of O-3 (5.88 g, 18.9 mmol) and (R)-(+)-2-methyl-2-propanesulfinamide (3.43 g, 28.3 mmol) in THF (120 mL). After 18 hours, $H_2O$ (120 mL) is added. After 5 minutes, the mixture is diluted with EtOAc (100 mL) and filtered. The organic layer is separated and washed with $H_2O$ (200 mL), dried over $Na_2SO_4$ and concentrated. The crude material is purified by silica gel chromatography eluting with a gradient of 0-100% EtOAc in heptane to provide O-4.

To a chilled (−78° C.) solution of O-4 (6.88 g, 16.6 mmol) in THF (300 mL) is added a 1M solution of L-Selectride in THF (19.9 mL, 19.9 mmol). After 1 hour, the reaction mixture is quenched with saturated aqueous NH₄Cl (100 mL) and the layers are separated. The aqueous layer is extracted with EtOAc (2×50 mL). The combined organic layers are washed with brine (50 mL), dried over Na₂SO₄, filtered and concentrated. The crude material is purified by silica gel chromatography eluting with a gradient of 0-100% EtOAc in heptane to provide O-5.

To a solution of O-5 (6.86 g, 16.47 mmol) in MeOH (55 mL) is added a 4N solution of HCl in dioxane (4.94 mL, 19.8 mmol). After 2 hours, the mixture is concentrated to provide O-6.

O-6 (0.50 g, 1.6 mmol), Pd(dba)₂ (46 mg, 0.08 mmol), 2-di-tert-butylphosphino-2',4',6',-triisopropylbiphenyl (68 mg, 0.16 mmol) and sodium tert-butoxide (319 mg, 3.32 mmol) are added to a reaction vial. Freshly degassed toluene (25 mL) is added and the mixture is warmed to 100° C. After 18 hours, the mixture is diluted with EtOAc (35 mL) and water (35 mL). The layers are separated and the organic layer is dried over Na₂SO₄, filtered, and concentrated. The crude material is purified by silica gel chromatography (eluting with a gradient of 0-100% EtOAc in heptane) to provide the title compound.

Synthesis of Intermediate Pb: (S)-1-(4-Fluorophenyl)-5-methyl-1,4,5,6,7,8-hexahydro-1,2,4-triazaazulene

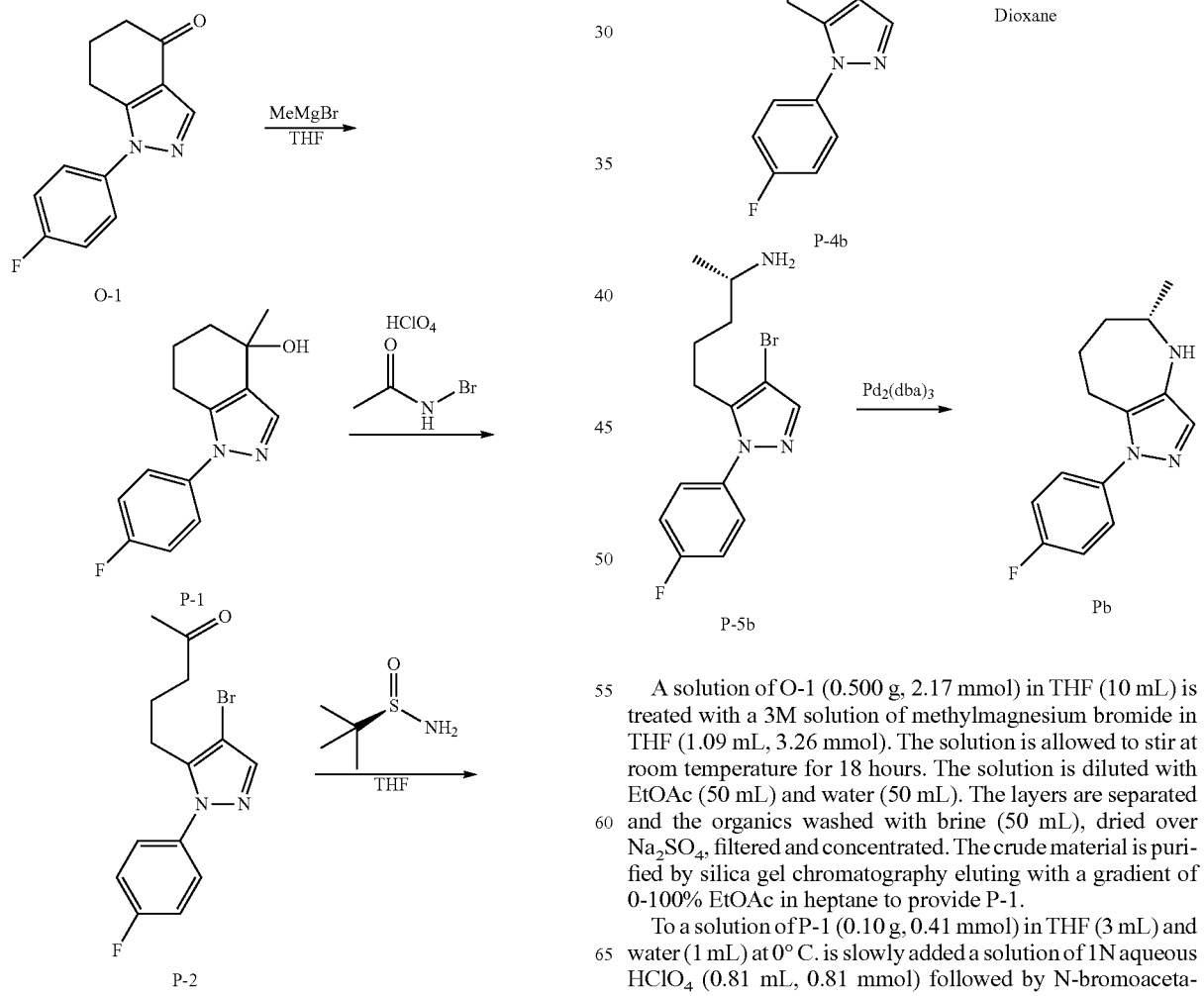

A solution of O-1 (0.500 g, 2.17 mmol) in THF (10 mL) is treated with a 3M solution of methylmagnesium bromide in THF (1.09 mL, 3.26 mmol). The solution is allowed to stir at room temperature for 18 hours. The solution is diluted with EtOAc (50 mL) and water (50 mL). The layers are separated and the organics washed with brine (50 mL), dried over Na₂SO₄, filtered and concentrated. The crude material is purified by silica gel chromatography eluting with a gradient of 0-100% EtOAc in heptane to provide P-1.

To a solution of P-1 (0.10 g, 0.41 mmol) in THF (3 mL) and water (1 mL) at 0° C. is slowly added a solution of 1N aqueous HClO₄ (0.81 mL, 0.81 mmol) followed by N-bromoacetamide (110 mg, 0.81 mmol). After 18 hours, the mixture is concentrated and diluted with DCM (15 mL) and water (10 mL) and the organic layer is separated. The organic layer is washed with brine (15 mL) and dried over Na₂SO₄, filtered and concentrated. The crude material is purified by silica gel chromatography eluting with a gradient of 0-100% EtOAc in heptane to provide P-2.

A mixture of P-2 (620 mg, 1.91 mmol), (R)-(+)-2-methyl-2-propanesulfinamide (0.71 g, 5.7 mmol) and Ti(OiPr)₄ (1.68 mL, 5.72 mmol) in THF (10 mL) is warmed at reflux. After 18 hours, the mixture is diluted with EtOAc (200 mL) and water (6 mL). After 10 minutes, the mixture is filtered, concentrated and purified by silica gel chromatography eluting with a gradient of 0-70% EtOAc in hexanes to provide P-3.

To a chilled (−78° C.) solution of P-3 (710 mg, 1.7 mmol) in THF (5 mL) is added a 1N solution of L-Selectride in THF (1.82 mL, 1.82 mmol). After 1 hour, is mixture is quenched with saturated aqueous NH₄Cl (50 mL). The layers are separated and the aqueous layer is extracted with EtOAc (2×50 mL). The combined organic layers are washed with brine (50 mL), dried over Na₂SO₄, filtered and concentrated. The crude material is purified by silica gel chromatography eluting with a gradient of 0-100% EtOAc in heptane to provide two diastereomers, first P-4-a (60 mg, 8.4%) and second P-4-b (302 mg, 42.3%). Stereochemistry is assigned based on known stereochemical preference (see: Chelucci, G. *Tetrahedron: Asymmetry* 2006, 17, 3163) of the reaction favoring formation of the S-diastereomer when using the R-sulfinamide chiral auxillary. Both intermediate are taken on separately. Conversion of P-4-b to Pb is described below.

To a solution of P-4-b (302 mg, 0.14 mmol) in MeOH (5 mL) is added a solution of 4N HCl in dioxane (0.21 mL, 0.84 mmol). After 1 hour, the mixture is concentrated to provide P-5b.

P-5b (250 mg, 0.77 mmol), Pd(dba)₂ (35 mg, 0.06 mmol), 2-di-tert-butylphosphino-2',4',6',-triisopropylbiphenyl (48 mg, 0.11 mmol) and sodium tert-butoxide (229 mg, 2.38 mmol) is added to a reaction vial. Freshly degassed toluene (1 mL) is added and the mixture is warmed at 100° C. After 18 hours, the mixture is diluted with EtOAc (15 mL) and water (15 mL). The layers are separated and the organic layer is dried over Na₂SO₄, filtered and concentrated. The crude material is purified by silica gel chromatography eluting with a gradient of 0-100% EtOAc in heptane to provide the title compound.

Synthesis of Intermediate Q: (S)-1-(4-Fluorophenyl)-5-methyl-4,5,6,7-tetrahydro-1H-pyrazolo[4,3-b]pyridine

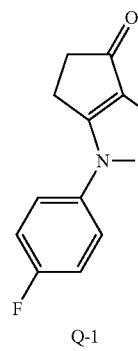

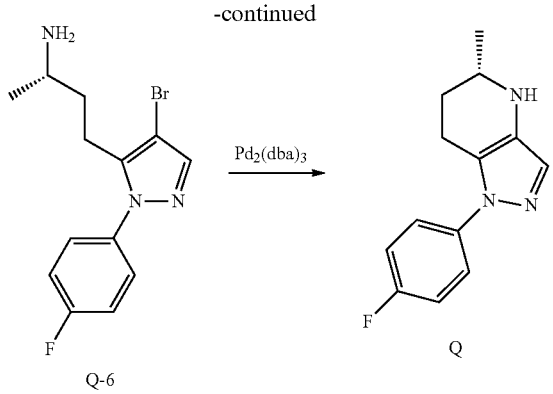

Q-6 → Q (Pd2(dba)3)

To a solution of Q-1 (0.500 g, 2.31 mmol) in THF (10 mL) is added a solution of 3M methylmagnesium chloride in THF (1.16 mL, 3.47 mmol). After 18 hours, the mixture is diluted with EtOAc (50 mL) and water (50 mL). The organic layer is separated and washed with brine (50 mL), dried over $Na_2SO_4$, filtered and concentrated. The crude material is purified by silica gel chromatography eluting with a gradient of 0-100% EtOAc in heptane to provide Q-2.

To a solution of Q-2 (230 mg, 0.99 mmol) in THF (15 mL) and water (5 mL) at 0° C. is slowly added a aqueous solution of 1N $HClO_4$ (1.96 mL, 1.96 mmol) followed by N-bromoacetamide (271 mg, 1.96 mmol). After 18 hours, the mixture is concentrated, diluted with DCM (15 mL) and water (10 mL). The organic layer is separated and washed with brine (15 mL), dried over $Na_2SO_4$, filtered and concentrated. The crude material is purified by silica gel chromatography eluting with a gradient of 0-60% EtOAc in heptane to provide Q-3.

A mixture of Q-3 (100 mg, 0.3 mmol), (R)-(+)-2-methyl-2-propanesulfinamide (0.08 g, 0.64 mmol) and $Ti(OiPr)_4$ (0.28 mL, 0.96 mmol) in THF (5 mL) is warmed at 60° C. After 18 hours, the mixture is diluted with EtOAc (100 mL) and water (6 mL). After 10 minutes, the mixture is filtered and concentrated and purified by silica gel chromatography eluting with a gradient of 0-50% EtOAc in hexanes to provide Q-4.

To a chilled (−78° C.) solution of Q-4 (90 mg, 0.22 mmol) in THF (5 mL) is added a 1N solution of L-Selectride in THF (0.26 mL, 0.26 mmol). After 1 hour, the reaction mixture is quenched with of saturated aqueous $NH_4Cl$ (50 mL). The layers are separated and the aqueous layer extracted with EtOAc (2×50 mL). The combined organic layers are washed with brine (50 mL), dried over $Na_2SO_4$, filtered and concentrated. The crude material is purified by silica gel chromatography eluting with a gradient of 0-100% EtOAc in heptane to provide Q-5. Stereochemistry is assigned based on known stereochemical preference of the reaction (see: Chelucci, G. Tetrahedron: Asymmetry 2006, 17, 3163) favoring formation of the S-diastereomer when using the R-sulfinamide chiral auxiliary. Intermediate Q is consistent with intermediate J-B by analysis of both intermediates and final compounds. Use of the S-sulfinamide chiral auxiliary is expected to provide J-A.

To a solution of Q-5 (38 mg, 0.09 mmol) in MeOH (5 mL) is added a solution of 4N HCl in dioxane (0.03 mL, 0.11 mmol). After 1 hour, the mixture is concentrated to provide Q-6.

Q-6 (30 mg, 0.09 mmol), Pd(dba)2 (4.6 mg, 0.01 mmol), 2-di-tert-butylphosphino-2',4',6',-triisopropylbiphenyl (6.4 mg, 0.02 mmol) and sodium tert-butoxide (30 mg, 0.31 mmol) is added to a reaction vial. Freshly degassed toluene (1 mL) is added and the mixture is warmed at 100° C. After 18 hours, the solution is diluted with EtOAc (5 mL) and water (5 mL). The layers are separated and the organic layer is dried over $Na_2SO_4$, filtered and concentrated. The crude material is purified by silica gel chromatography eluting with a gradient of 0-100% EtOAc in heptane to provide Q.

Synthesis of Intermediate R: 1-(4-Fluorophenyl)-5,5-dimethyl-4,5,6,7-tetrahydro-1H-pyrazolo[4,3-b]pyridine

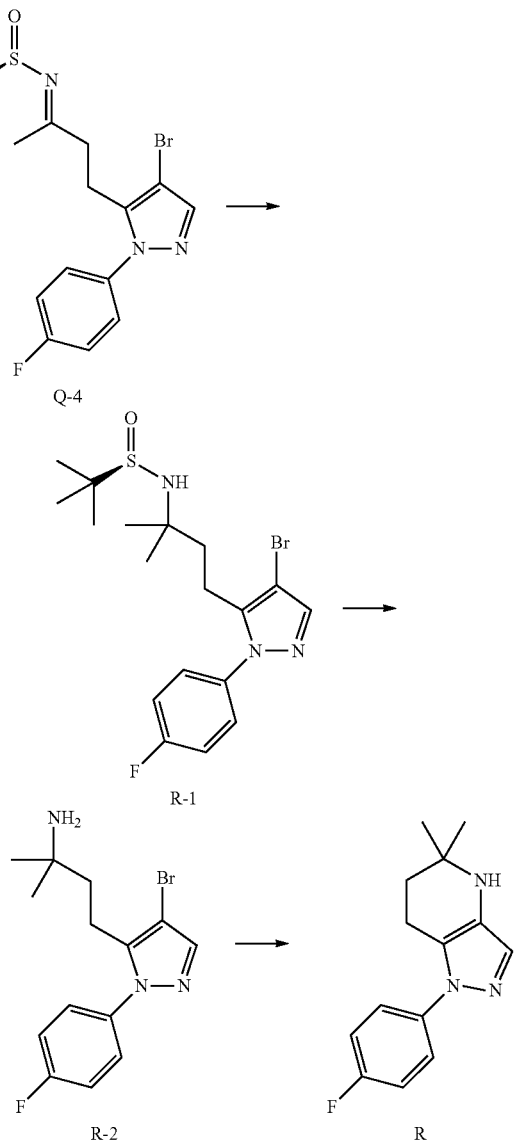

To a solution of Q-4 (0.34 g, 0.82 mmol) in toluene (15 mL) at −78° C. is added a solution of 3M methylmagnesium chloride in THF (0.3 mL, 0.9 mmol). The mixture is slowly warmed to ambient temperature over 2 hours and then diluted with a saturated aqueous $NH_4Cl$ (30 mL). The layers are separated and the aqueous layer is extracted with EtOAc (3×10 mL). The combined organic layers are dried over $Na_2SO_4$ and concentrated. The material is purified by silica gel chromatography using a 0-70% EtOAc in heptane gradient to provide R-1.

To a solution of R-1 (0.23 g, 0.53 mmol) in methanol (5 mL) is added a solution of 4N HCl in dioxane (0.2 mL, 0.8 mmol). After 2 hours, the mixture is concentrated to provide R-2.

R-2 (0.15 g, 0.40 mmol), Pd(dba)$_2$ (0.03 g, 0.05 mmol), 2-di-tert-butylphosphino-2',4',6',-triisopropylbiphenyl (0.04 g, 0.1 mmol) and sodium tert-butoxide (0.12 g, 1.2 mmol) are added to a reaction vial and the vial is filled and evacuated with argon three times. Freshly degassed toluene (3 mL) is added and the mixture is warmed to 100° C. After 10 hours, the mixture is diluted with saturated aqueous NH$_4$Cl (10 mL) and extracted with EtOAc (3×10 mL). The combined organics are washed with brine (20 mL) dried over Na$_2$SO$_4$ and concentrated. The crude material is purified by silica gel chromatography using a gradient of 0-100% EtOAc in heptane to provide the title compound.

Synthesis of Intermediate S: 1-(4-Fluorophenyl)-6,6-dimethyl-4,5,6,7-tetrahydro-1H-pyrazolo[4,3-b]pyridine

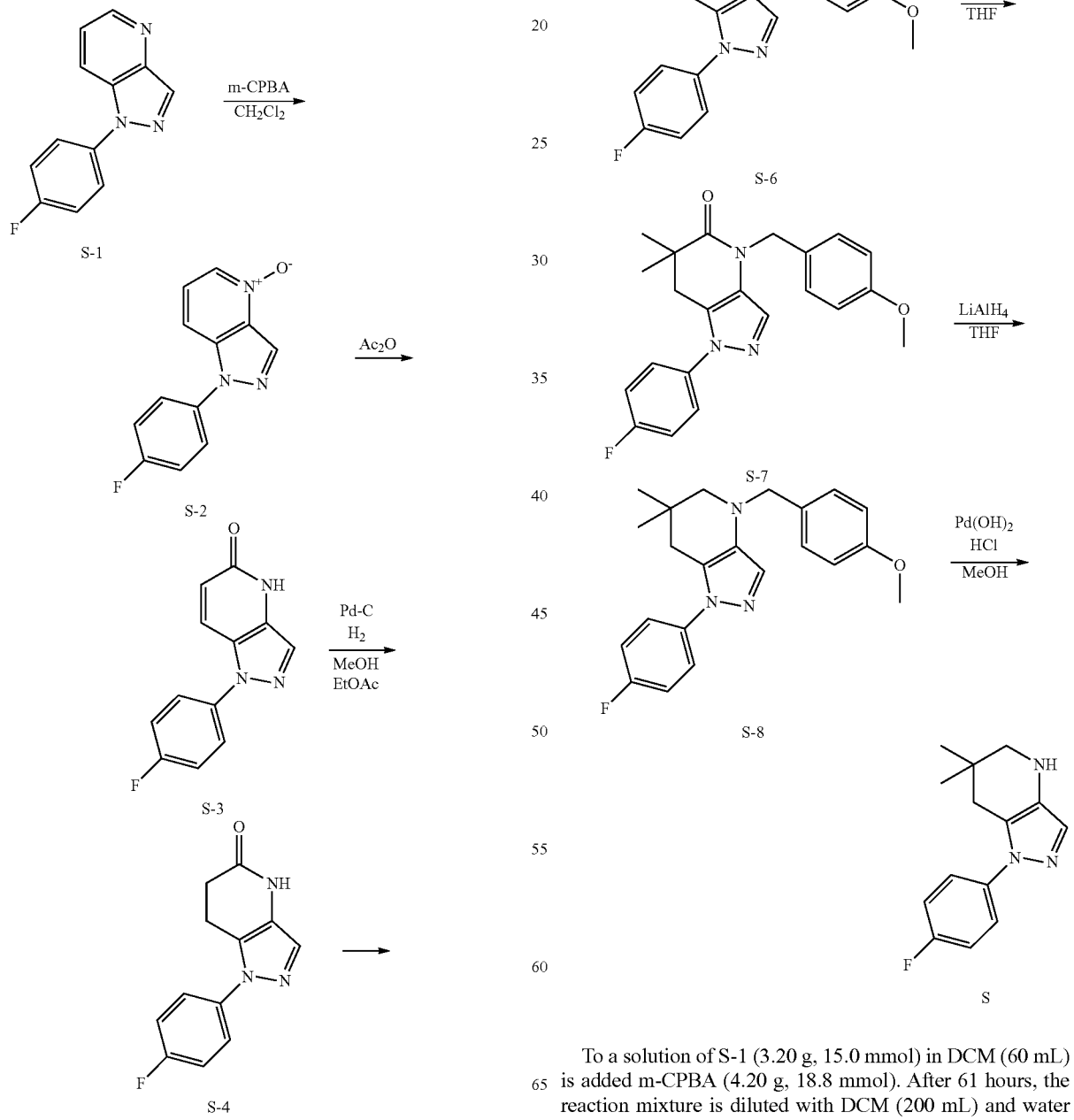

To a solution of S-1 (3.20 g, 15.0 mmol) in DCM (60 mL) is added m-CPBA (4.20 g, 18.8 mmol). After 61 hours, the reaction mixture is diluted with DCM (200 mL) and water (100 mL). The layers are separated, and the aqueous layer is extracted with DCM (100 mL). The combined organic layers are washed with saturated aqueous NaHCO$_3$ (200 mL), brine (200 mL), dried over MgSO$_4$, filtered and concentrated. The crude is purified on silica gel using a gradient of 0-10% MeOH in CH$_2$Cl$_2$ to provide S-2.

A solution of S-2 (2.70 g, 11.8 mmol) in acetic anhydride (55 mL) is warmed in a sealed pressure tube at 140° C. After 28 hours, the reaction quenched with water (100 mL) and warmed to 90° C. After 6 hours, the mixture is cooled to room temperature, neutralized with 2N aqueous NaOH, and extracted with EtOAc (3×500 mL). The combined organic layers are washed with brine (100 mL), dried over MgSO$_4$, filtered and concentrated.

The residue is purified by silica gel chromatography using a gradient of 0-8% MeOH in CH$_2$Cl$_2$ to provide S-3.

A solution of S-3 (1.30 g, 5.67 mmol) and 10% Pd on carbon (1.80 g, 50% water by WT) in a mixture of MeOH (400 mL) and EtOAc (400 mL) is stirred under an atmosphere of H$_2$. Upon completion (as determined by $^1$H NMR), the mixture filtered through filter agent and concentrated to provide S-4.

To a chilled (5° C.) solution of S-4 (720 mg, 3.11 mmol) in DMF (10 mL) is added NaH (60% dispersion in oil, 162 mg, 4.05 mmol). After H$_2$ evolution ceased, p-methoxybenzyl chloride (0.550 mL, 4.05 mmol) is added and the mixture is warmed to room temperature. After 16 hours, the reaction is diluted with water (50 mL) and extracted with EtOAc (3×50 mL). The combined organic layers are washed with brine (100 mL) dried over MgSO$_4$, filtered and concentrated. The crude mixture is purified on SiO$_2$ using a gradient of 0-100% MTBE in heptane. The solid is triturated with Et$_2$O (2×2 mL) to provide S-5.

To a chilled (−78° C.) solution of 1M LHMDS (2.85 mL, 2.85 mmol) in hexane in THF (5 mL) is added a solution of S-5 (910 mg, 2.59 mmol) in THF (10 mL). After 30 minutes, MeI (177 μL, 2.85 mmol) is added. After 2 hours, the mixture is quenched with water (50 mL) and extracted with EtOAc (3×50 mL). The combined organic layers are washed with brine (100 mL), dried over MgSO$_4$, filtered and concentrated. The crude mixture is purified on SiO$_2$ using a gradient of 0-90% EtOAc in heptane to provide S-6.

To a chilled (−78° C.) solution of S-6 (768 mg, 2.10 mmol) in THF (15 mL) is added a 2M solution LDA (2M, 1.16 mL) in THF. After 30 minutes, MeI (144 μL, 2.31 mmol) is added. After 2 hours, the mixture is quenched with water (50 mL) and extracted with EtOAc (3×50 mL). The combined organic layers are washed with brine (100 mL), dried over MgSO$_4$, filtered and concentrated. The residue is purified on SiO$_2$ using a gradient of 0-40% EtOAc in heptane and is triturated with Et$_2$O (3 mL) to provide S-7.

To a solution of S-7 (772 mg, 2.03 mmol) in THF (100 mL) is added a solution of 1M LAH in THF (8.20 mL, 8.20 mmol) and the mixture is warmed at reflux. After 8 hours, the mixture is cooled to room temperature. After 39 hours, the mixture is cooled to 0° C., quenched first with a mixture of THF (2 mL) and water (600 μL) and then water (1.2 mL). After 30 minutes, the mixture is diluted with brine (30 mL) and extracted with EtOAc (5×30 mL). The combined organic layers are washed with saturated aqueous NH$_4$Cl (100 mL), saturated aqueous NaHCO$_3$ (100 mL), brine (100 mL), dried over MgSO$_4$, filtered and concentrated. The residue is purified on SiO$_2$ using a gradient of 0-40% EtOAc in heptane to provide S-8.

A solution of S-8 (600 mg) and 20% Pd(OH)$_2$ on carbon (300 mg) in MeOH (50 mL) and 12M aqueous HCl (50 μL) is placed under an atmosphere of H$_2$. After 3 hours, the mixture is filtered through filter agent and concentrated. The residue is purified by RP-HPLC on a C18 semi-preparative column using an isocratic mixture of 20% MeCN (+0.1% TFA) in H$_2$O (+0.1% TFA) over 20 minutes. The combined desired fractions are neutralized with saturated aqueous NaHCO$_3$ concentrated extracted with EtOAc (3×50 mL). The combined organic layers are washed with brine (50 mL), dried over MgSO$_4$, filtered and concentrated to provide the title compound.

Synthesis of Intermediate T: 1-(4-Fluorophenyl)-4,5,6,7-tetrahydro-1H-pyrazolo[4,3-b]pyridine-6-carboxylic acid ethyl ester

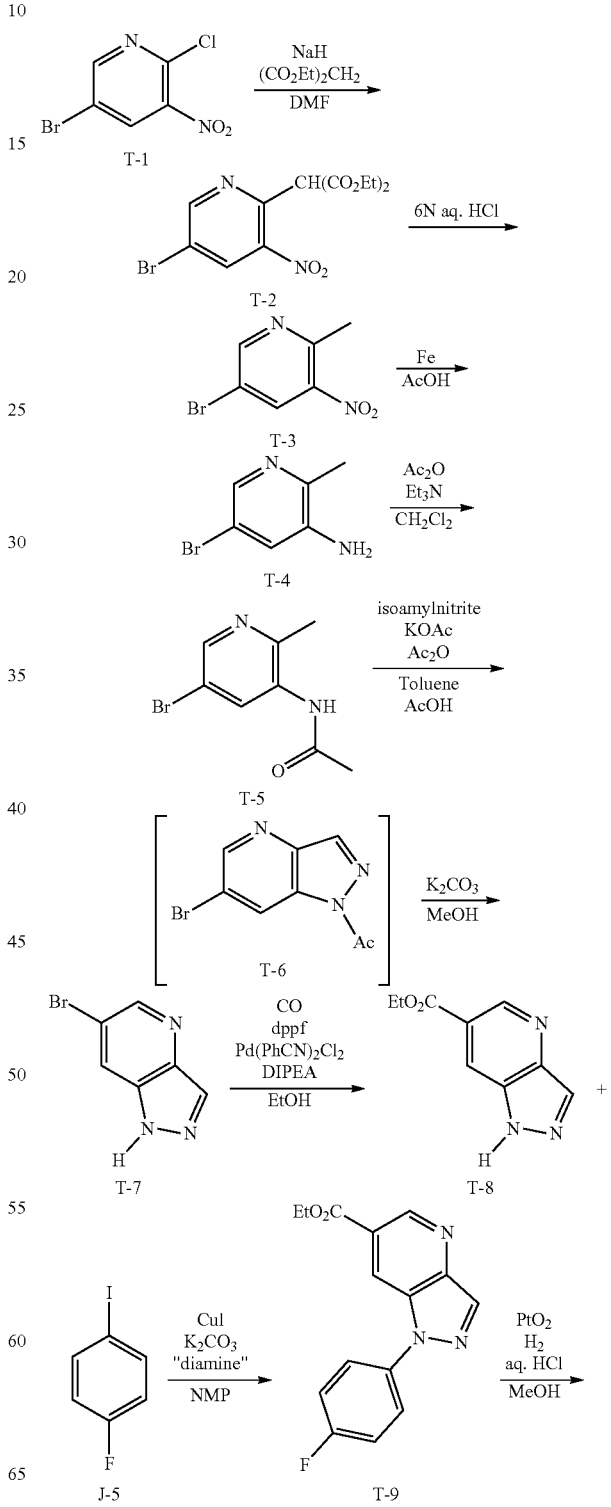

-continued

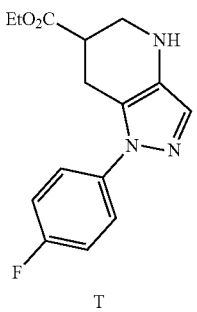

T

To a chilled (−10° C.) suspension of 60% sodium hydride in mineral oil (5.564 g, 139.1 mmol) in DMF (100 mL) is added a solution of diethyl malonate (21.50 mL, 141.6 mmol) in DMF (50 mL). After hydrogen evolution ceased, T-1 (20.62 g, 86.84 mmol) is added. After 4 hours, the mixture is poured into saturated aqueous NH₄Cl (200 mL) and extracted with Et₂O (3×200 mL). The combined organic layers are washed with water (5×100 mL), brine (2×100 mL), dried over magnesium sulfate, filtered and concentrated to provide T-2.

A mixture of T-2 (31.4 g, 361 mmol) in 6N HCl (320 mL) is warmed at reflux. After 4 hours, the mixture is diluted with water (500 mL), made basic with NaHCO₃ and extracted with Et₂O (3×150 mL) and EtOAc (50 mL). The combined organic layers are washed with saturated aqueous K₂CO₃ (3×50 mL), brine (40 mL), dried over magnesium sulfate, filtered and concentrated. The residue is diluted with heptane to provide T-3.

A mixture of T-3 (13.2 g, 60.8 mmol) and iron powder (11.50 g, 205.9 mmol) in acetic acid (150 mL) is warmed at reflux. After 2 hours, the reaction is diluted with Et₂O (100 mL) and EtOAc (250 mL) and filtered through filter agent washing with ethyl acetate. The filtrate is diluted with water (200 mL) made basic with first K₂CO₃ and then NaHCO₃ and extracted with EtOAc (3×150 mL). The combined organic layers are washed with saturated aqueous NaHCO₃ (100 mL), brine (2×100 mL), dried over magnesium sulfate, filtered and concentrated to provide T-4.

To a solution of T-4 (12.1 g, 64.6 mmol) in DCM (50 mL) is added acetic anhydride (9.50 mL, 98.5 mmol) followed by Et₃N (20.0 mL, 143.7 mmol). After 18 hours, the reaction is concentrated and the residue is diluted with methanol (200 mL) and K₂CO₃ (35 g) is added. After 1 hour, the mixture is concentrated and diluted with water and the solid is collected by filtration to provide T-5.

To a solution of T-5 (13.14 g, 57.36 mmol) in toluene (200 mL) is added acetic anhydride (16.50 mL, 174.5 mmol), acetic acid (16.50 mL, 288.2 mmol) and potassium acetate (12.30 g, 125.3 mmol). The mixture is warmed at reflux and isoamyl nitrite (10.0 mL, 71.5 mmol) is added. After 3 hours, the reaction is concentrated to provide without isolation T-6. The residue is diluted with methanol (250 mL) and K₂CO₃ (32.0 g, 188 mmol) is added and the mixture is warmed at reflux. After 1 hour, the reaction is poured into water and extracted with EtOAc (3×150 mL). The combined organic layers are washed with brine (2×50 mL), dried over magnesium sulfate, filtered through a pad of silica gel and filter agent and concentrated. The solid is triturated with Et₂O to provide T-7. The filtrate is purified on silica gel using a gradient of 25-100% EtOAc in hexanes and then 5% methanol in ethyl acetate. The material from the column is triturated with ether-heptane to provide T-7.

A mixture of T-7 (1.60 g, 8.08 mmol), DIPEA (2.00 mL, 11.5 mmol), dichlorobis(benzonitrile)palladium (II) (100.0 mg, 0.26 mmol), and 1,1-bis(diphenylphosphino)ferrocene (dppf) (200.0 mg, 0.36 mmol) in absolute EtOH (35 mL) in a pressure reactor is placed under 15 bars of carbon monoxide and warmed at 135° C. After 4 hours, the mixture is cooled to room temperature, returned to atmospheric pressure and opened. The reaction is concentrated and then diluted with brine (100 mL) and extracted with EtOAc (3×75 mL). The combined organic layers are washed with brine (3×50 mL), dried over magnesium sulfate, treated with decolorizing carbon, filtered through filter agent and silica gel and concentrated. The residue is dissolved in DCM and passed through silica gel eluting with Et₂O to provide T-8.

A solution of T-8 (1.20 g, 6.28 mmol), CuI (487.0 mg, 2.56 mmol), K₂CO₃ (1.60 g, 11.6 mmol), N,N-dimethyl-1,2-diaminocyclohexane (80.0 µL, 0.51 mmol) and J-5 (935.0 µL, 8.11 mmol) in DMF (15 mL) is warmed at 130° C. in a microwave reactor. After 1.5 hours, additional CuI (250 mg), 4-fluoroiodobenzene (0.46 mL) and diamine (40 µL) is added. After 1.5 hours, the reaction is diluted with saturated aqueous NH₄Cl (150 mL) and then NaHCO₃ is added followed by EtOAc (150 mL). The mixture is warmed on a hot plate and the organic layer is separated. The aqueous layer extracted with EtOAc (2×50 mL). The combined organic layers are washed with saturated aqueous NH₄Cl (30 mL), brine (2×30 mL), dried over magnesium sulfate, treated with decolorizing carbon, diluted with an equal volume of heptane and filtered through silica gel and filter agent and concentrated. The residue is purified by silica gel chromatography using a gradient of 0-100% EtOAc in heptane and crystallized from ether-heptane to provide T-9.

To a solution of T-9 (310.0 mg, 1.09 mmol) in EtOH (12 mL) and 4N HCl in dioxane (1 mL) under argon is added Pt (IV) oxide hydrate (200 mg) and the mixture is placed under one atmosphere of hydrogen. After 18 hours, the mixture is diluted with filter agent and filtered through filter agent. The mixture is made basic with saturated aqueous NaHCO₃ and concentrated. The residue is diluted with water (30 mL) and extracted with EtOAc (2×30 mL). The combined organic layers are washed with brine (2×20 mL), dried over Na₂SO₄, filtered and concentrated to provide the title compound.

The following intermediate is synthesized in similar fashion starting with 2-hydroxy-3-nitro-5-(trifluoromethyl)pyridine which is converted to 2-chloro-3-nitro-5-(trifluoromethyl)pyridine using POCl₃.

| Intermediate | Structure |
|---|---|
| U | ![structure with CF₃, NH, pyrazole, and 4-fluorophenyl groups] |

109

Synthesis of Intermediate V: 1-(4-Fluorophenyl)-6-methyl-4,5,6,7-tetrahydro-1H-pyrazolo[4,3-b]pyridine

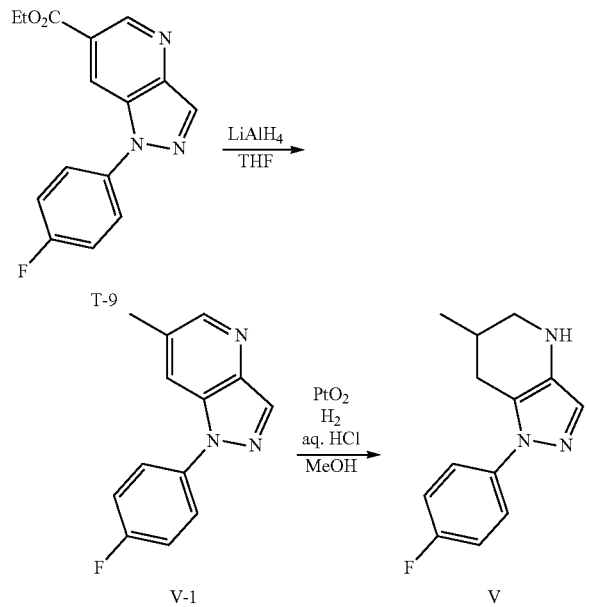

To a solution of T-9 (570 mg, 2.00 mmol) in THF (20 mL) is added lithium aluminum hydride (375 mg, 9.62 mmol). After 18 hours, the mixture is quenched with water, dried with magnesium sulfate, filtered through filter agent and concentrated. The crude material is purified by silica gel chromatography eluting with a 5-40% gradient of ethyl acetate in heptane to afford V-1.

V-1 is converted to V according to methods described above, for example see: Synthesis of intermediate T (T-9 to T).

SYNTHETIC EXAMPLES

All Compound Numbers Correspond to the Numbers Found in Table I and II

Example 1

Synthesis of 1-(4-fluorophenyl)-N-phenyl-1,5,6,7-tetrahydro-4H-pyrazolo[4,3-b]pyridine-4-carboxamide (Compound 1)

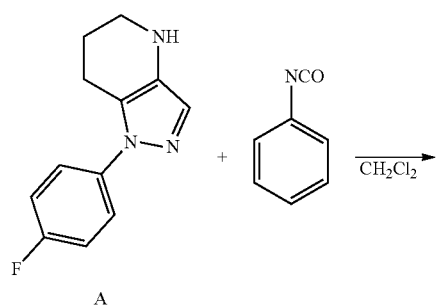

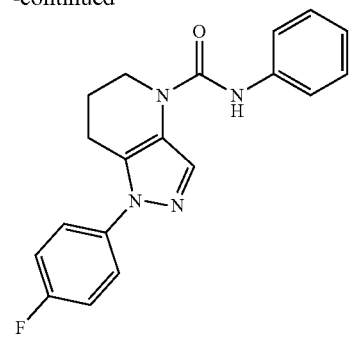

Phenyl isocyanate (32.9 mg, 0.276 mmol) is dissolved in CH$_2$Cl$_2$ (0.5 mL) and a solution of A (50 mg, 0.23 mmol) in CH$_2$Cl$_2$ (2 mL) is added. After 2 days, the reaction is evaporated to dryness and the residue is purified by reverse phase LCMS to provide the title compound.

The following compounds are synthesized in a similar fashion using the appropriate isocyanates:

Compounds 2-20, and 37.

Example 2

1-(4-Fluorophenyl)-N-[3-(trifluoromethyl)benzyl]-1,5,6,7-tetrahydro-4H-pyrazolo[4,3-b]pyridine-4-carboxamide (Compound 21)

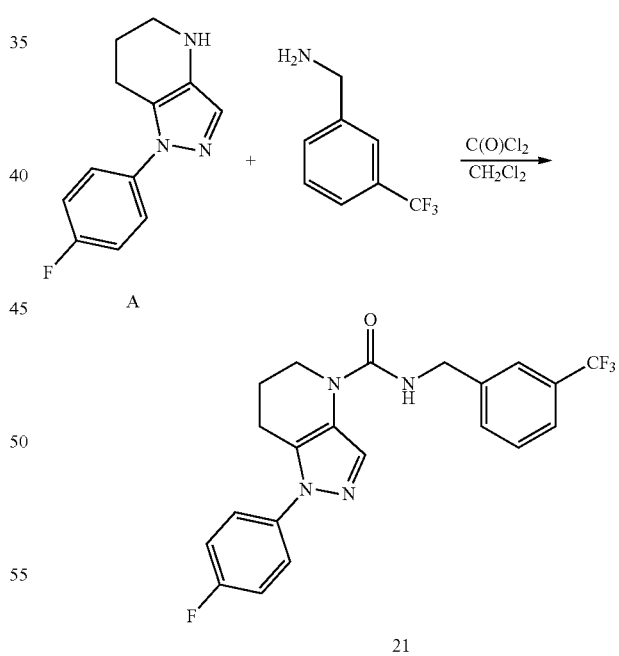

To a chilled (0° C.) solution of intermediate A (54 mg, 0.24 mmol) in DCM (5 mL) and saturated NaHCO$_3$ (5 mL) is added a 20% solution of phosgene (0.4 mL, 0.75 mmol) in toluene directly to lower (DCM) phase. The mixture is then vigorously stirred. After 1 hour, the organic phase is separated and the aqueous layer extracted with DCM (15 mL). The combined organic layers are dried over MgSO$_4$ and concentrated. The residue is diluted with DCM (5 mL) and 3-trifluoromethylbenzyl amine (0.04 mL, 0.27 mmol) is added. After 3 hours, the mixture is concentrated and purified by silica gel chromatography eluting with a gradient of EtOAc in hexanes to provide the title compound.

The following compounds and intermediates are synthesized from intermediate A as above using the appropriate intermediates:

Compound 22, 24-25, 31, 38-40; and intermediates 1-(4-fluorophenyl)-1,5,6,7-tetrahydro-pyrazolo[4,3-b]pyridine-4-carboxylic acid (2-bromo-pyridin-4-ylmethyl)-amide and (1-(4-fluorophenyl)-1,5,6,7-tetrahydro-pyrazolo[4,3-b]pyridine-4-carboxylic acid [(S)-1-(6-bromo-pyridin3-yl)-ethyl]-amide).

The following compounds are synthesized in similar fashion from intermediate A, only with the addition of 2 equivalents of diisopropylethylamine (DIPEA) following the addition of the appropriate benzyl amine.

Compounds 41, 42, 46, 59, 60.

The following compound is synthesized in similar fashion, only with the addition of 1.2 equivalents of triisopropylamine (TEA).

Compound 23.

The following compounds are synthesized as above using intermediate B or C, as appropriate:

Compounds 62, 63.

The following compounds are synthesized as above with phosgene using intermediate G or H as described above:

Compounds 65-67.

The following compound is synthesized as above with phosgene using intermediate I as described above.

Compound 71.

The following compounds are synthesized as above with phosgene using intermediate L or N as described above.

Compound 86 and 110.

The following compound is synthesized as above with phosgene using intermediate M as described above:

Compound 93.

Example 3

Synthesis of 1-(4-Fluorophenyl)-1,5,6,7-tetrahydro-pyrazolo[4,3-b]pyridine-4-carboxylic acid [(S)-1-(6-bromo-pyridin-3-yl)-propyl]-amide, (Compound 48)

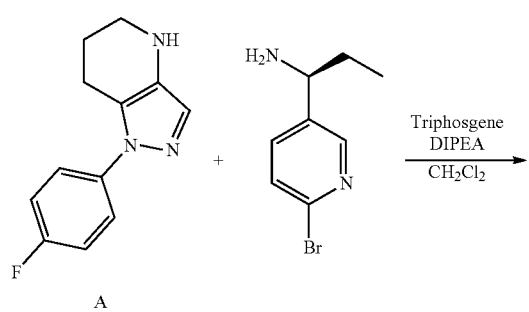

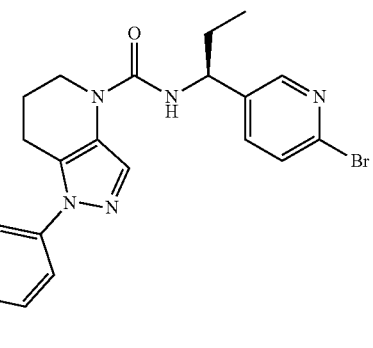

48

To a stirred solution of triphosgene (41 mg, 0.14 mmol) at 0° C. in of DCM (2 mL) is added a solution of the amine (100 mg, 0.46 mmol) in DCM (1 mL) over 20 minutes. A solution of DIPEA (0.32 mmol, 1.86 mmol) is added in DCM (1 mL) dropwise over 5 minutes and the solution is stirred for 30 minutes. A solution of A (101 mg, 0.46 mmol) in 1 mL of DCM is added. After 18 hours, the mixture is diluted with DCM (50 mL). The organic layer is washed with saturated NaHCO$_3$ (40 mL), brine (40 mL), dried over Na$_2$SO$_4$, filtered and concentrated. The crude material is purified by silica gel chromatography eluting with a gradient of 0-10% MeOH in DCM to provide the title compound.

The following compound is synthesized in similar fashion from intermediate A: Compound 49.

Example 4

Synthesis of 1-(4-Fluorophenyl)-1,5,6,7-tetrahydro-pyrazolo[4,3-b]pyridine-4-carboxylic acid 4-(tetrahydro-pyran-4-ylsulfamoyl)-benzylamide (Compound 28)

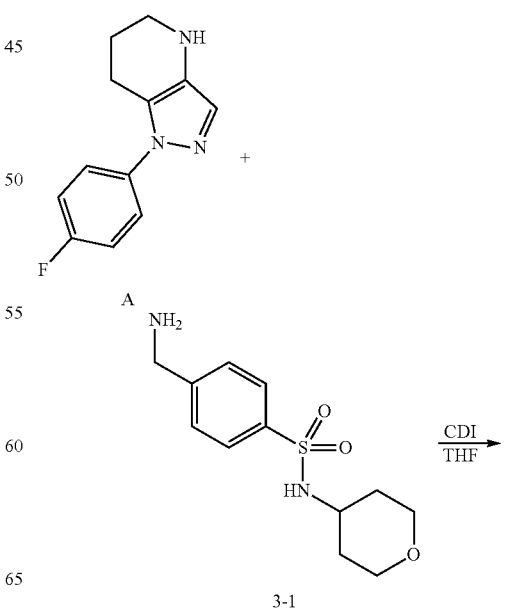

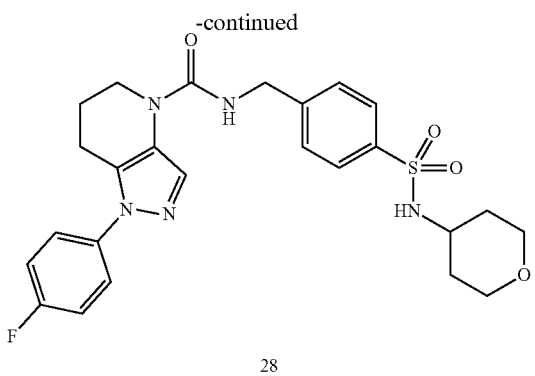

28

To CDI (0.06 g, 0.37 mmol) in THF (3 mL) is added a solution of 3-1 (0.1 g, 0.37 mmol) in THF (3 mL). After 3 hours, A (0.08 g, 0.37 mmol) is added and the reaction is warmed at reflux. After 18 hours, the mixture is concentrated, purified by silica gel chromatography eluting with a gradient of 0-100% EtOAc in hexanes and crystallized from EtOAc-ether to provide the title compound.

The following compounds and intermediates are synthesized in similar fashion from intermediate A:

Compounds 26, 27, 29, 30, 33-36; and intermediates 1-(4-fluorophenyl)-1,5,6,7-tetrahydro-pyrazolo[4,3-b]pyridine-4-carboxylic acid 4-methanesulfonyl-3-methoxy-benzylamide (Example 8, 8-1) and 1-(4-fluorophenyl)-1,5,6,7-tetrahydro-pyrazolo[4,3-b]pyridine-4-carboxylic acid (2-bromo-pyridin-4-ylmethyl)-amide.

Example 5

Synthesis of 1-(4-Fluorophenyl)-1,5,6,7-tetrahydro-pyrazolo[4,3-b]pyridine-4-carboxylic acid [(S)-1-(5-methanesulfonyl-pyridin-3-yl)-ethyl]-amide (Compound 44)

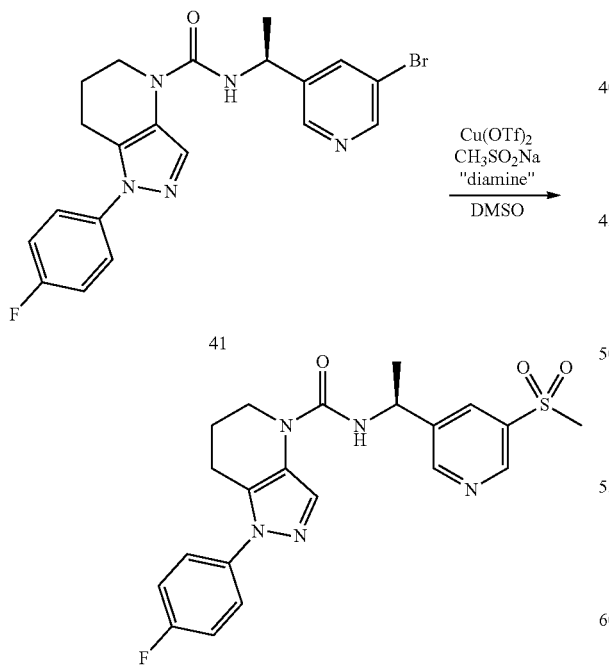

To a solution of 41 (75 mg, 0.17 mmol) in DMSO (1 mL) in a microwave tube is added sodium methane sulfinate (26 mg, 0.25 mmol), Cu(OTf)$_2$ (61 mg, 0.17 mmol) and N,N'-dimethylethylenediamine (0.05 mL, 0.51 mmol). The mixture is warmed in a microwave at 110° C. After 30 minutes, the mixture is warmed at 120° C. After 1 hour, the solution is diluted with EtOAc (20 mL) and washed with saturated NaHCO$_3$ (120 mL) and brine (10 mL). The aqueous layer is extracted with EtOAc (2×10 mL). The organic layers are dried over MgSO$_4$, filtered and concentrated. The crude material is purified by silica gel chromatography eluting with a gradient of 0-10% methanol in DCM to provide the title compound.

The following compounds are synthesized in similar fashion from the appropriate starting materials:
Compounds 45, 47, 50, 51, 52, 69,
The following compounds are synthesized in similar fashion from the appropriate starting materials except Cu(OTf)$_2$ is replaced by CuI.
Compounds 77, 82, 84, 90, 95 and 105.

Example 6

1-(4-Fluorophenyl)-5,6-dihydro-1H-pyrrolo[3,2-c]pyrazole-4-carboxylic acid [(S)-1-(2-methanesulfonyl-pyridin-4-yl)-butyl]-amide (Compound 87)

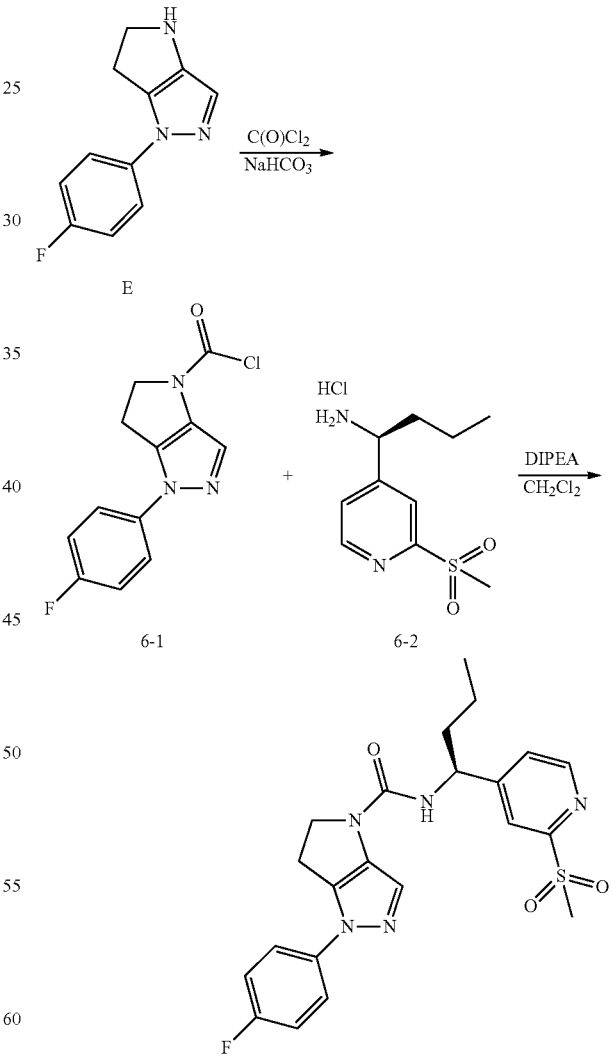

To a chilled (ice bath) solution of E (108 mg, 0.50 mmol) in DCM (9 mL) and saturated aqueous NaHCO$_3$ solution (6 mL) is added a solution of 20% phosgene in toluene (0.4 mL, 0.8 mmol). After 1 hour, the mixture is diluted with H$_2$O (10 mL)

and extracted with DCM (3×15 mL). The combined organic layers are washed with brine (10 mL), dried over MgSO$_4$, filtered and concentrated to provide 6-1.

To 6-1 (47 mg, 0.2 mmol) in DMF (2 mL) is added 6-2 (61 mg, 0.2 mmol) and DIPEA (0.2 mL, 1.1 mmol). After 16 hours, the mixture is partitioned between DCM (5 mL) and saturated aqueous NH$_4$Cl (10 mL). The organic layer is separated, dried over Na$_2$SO$_4$ and concentrated. The residue is purified by reversed phase C18 semi-preparative HPLC column using a solvent gradient from 20-95% H$_2$O in MeCN to provide the title compound.

The following compounds are synthesized in similar fashion from the appropriate intermediates:
Compounds 88 and 89.

Example 7

1-(4-Fluorophenyl)-5-methyl-5,6-dihydro-1H-pyrrolo[3,2-c]pyrazole-4-carboxylic acid [(S)-1-(2-methanesulfonyl-pyridin-4-yl)-butyl]-amide (Compound 108)

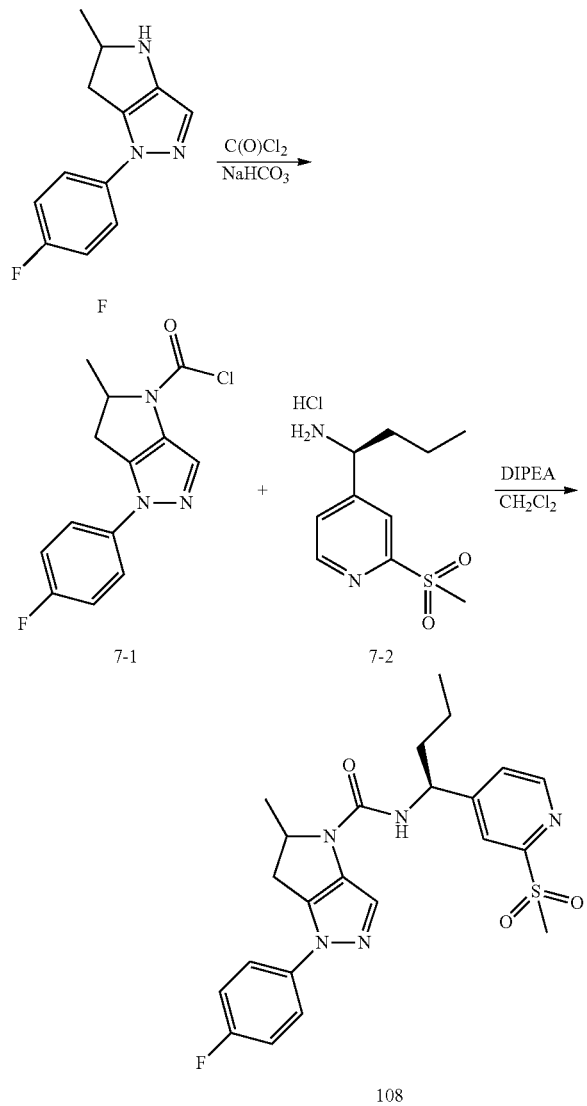

A chilled (0° C.) solution of F (135 mg, 0.6 mmol) in DCM (10.5 mL) and saturated aqueous NaHCO$_3$ (7 mL) is treated with a 20% solution of phosgene in toluene (0.5 mL, 0.9 mmol). After 1 hour, the mixture is diluted with H$_2$O (10 mL) and extracted with DCM (3×15 mL). The combined organic layers are washed with brine (10 mL), dried over MgSO$_4$, filtered and concentrated to provide 7-1.

To a solution of 7-1 (86 mg, 0.31 mmol) in DMF (3.5 mL) is added 7-2 (105.8 mg, 0.40 mmol) and DIPEA (0.32 mL, 1.84 mmol). After 2.5 hours, the mixture is concentrated. The crude material is purified by reversed phase C18 semi-preparative HPLC using a solvent gradient from 20-100% H$_2$O in MeCN to provide the title compound.

The following compound is synthesized in similar fashion from the appropriate intermediates:
Compound 109.

The following compounds are synthesized as above using intermediate O as described above.
Compounds 72-75.

The following compounds are synthesized as above using intermediates Pa or Pb as described above.
Compounds 100 and 101.

Example 8

Synthesis of 1-(4-Fluorophenyl)-1,5,6,7-tetrahydropyrazolo[4,3-b]pyridine-4-carboxylic acid 3-hydroxy-4-methanesulfonyl-benzylamide (Compound 43)

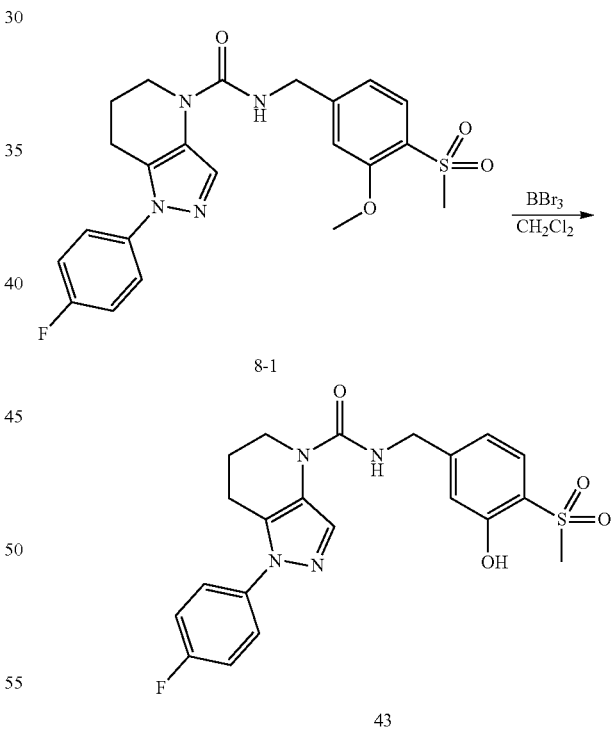

To a chilled (−78° C.) solution of 8-1 (0.04 g, 0.087 mmol) in DCM (5 mL) is added a 1M solution of BBr$_3$ (0.3 mL) in DCM. The mixture is slowly warmed to ambient temperature, quenched with saturated aqueous NaHCO$_3$ (10 mL) and extracted with EtOAc (3×10 mL). The combined organic layers are washed with brine (3×5 mL), dried over magnesium sulfate, filtered and concentrated. The crude material is crystallized from EtOAc-hexanes to provide the title compound.

The following compounds are synthesized in similar fashion from the appropriate intermediates:
Compounds 85, 96 and 106.

Example 9

Synthesis of 1-(4-Fluorophenyl)-5,5-dimethyl-1,5,6,7-tetrahydro-pyrazolo[4,3-b]pyridine-4-carboxylic acid [(S)-1-(2-methanesulfonyl-pyridin-4-yl)-butyl]-amide (Compound 119)

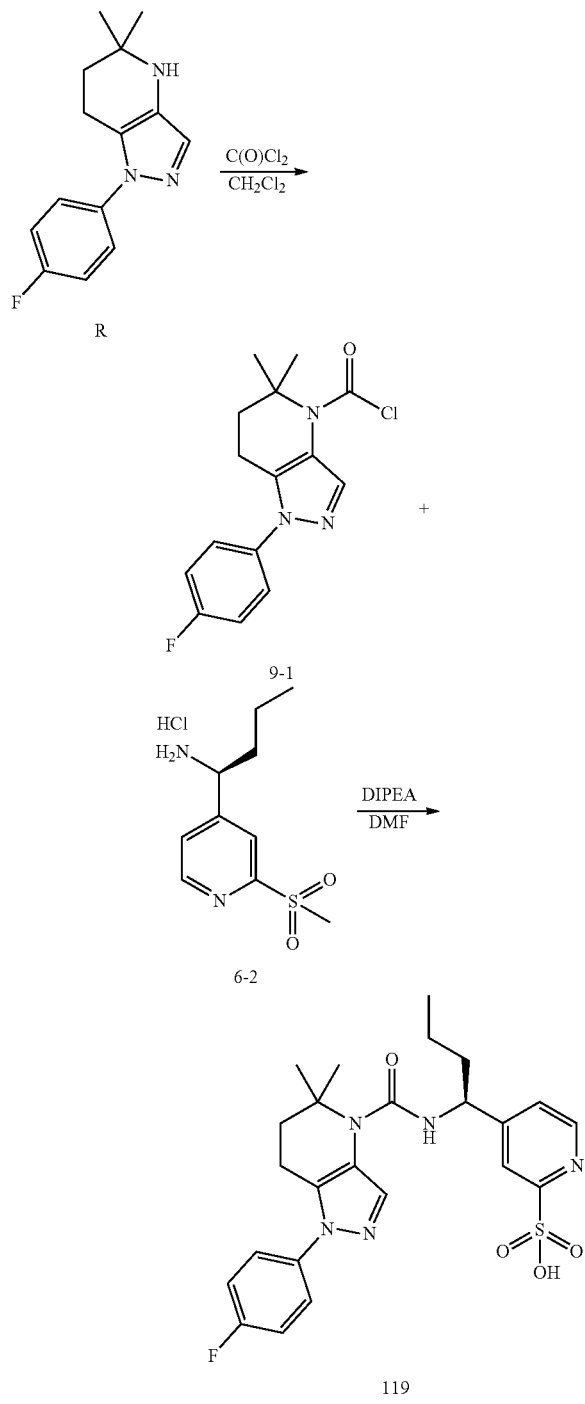

To a solution of R (30 mg, 0.12 mmol) in DCM (10 mL) and saturated aqueous $NaHCO_3$ (3 mL) is added a solution of 20% phosgene in toluene (0.4 mL, 0.8 mmol). After 30 minutes, additional 20% phosgene (0.4 mL, 0.8 mmol) in toluene is added. After 2 hours, the mixture is diluted with water and the DCM layer separated. The aqueous is extracted with DCM (2×10 mL). The combined organic layers are dried over $Na_2SO_4$, filtered and concentrated to provide the title compound.

To a solution of 9-1 in DMF (3 mL) is added 6-2 (0.050 g, 0.15 mmol) followed by DIPEA (0.1 mL, 0.6 mmol). After 18 hours, the mixture is poured into saturated aqueous $NH_4Cl$ (10 mL) and extracted with EtOAc (4×10 mL). The combined organic layers are washed with saturated aqueous $NH_4Cl$ (15 mL), brine (5 mL), dried over $Na_2SO_4$, filtered and concentrated. The crude material is purified by silica gel chromatography eluting with a gradient of 0-100% EtOAc in heptane to provide the title compound.

The following compounds are synthesized in similar fashion from intermediate D:

Compounds 98, 99, 120, 121.

The following compounds are synthesized in similar fashion from intermediate J:

Compounds 53, 54, 55, 70, 80, 81, 91, 107. Compounds 80 and 81 represent two diastereomers with opposite configuration at the methyl substituent.

The following compounds are synthesized in similar fashion from intermediate K:

Compounds 56, 57 and 58. Compounds 56 and 57 represent two diastereomers with opposite configuration at the trifluoromethyl substituent.

The following compounds are synthesized in similar fashion from intermediate K-A: Compounds 56, 61, 64, 68, 92, 94, 97, and 104.

The following intermediates are synthesized in similar fashion from intermediate K-A:

(S)-1-(4-fluorophenyl)-5-trifluoromethyl-1,5,6,7-tetrahydro-pyrazolo[4,3-b]pyridine-4-carboxylic acid [(S)-1-(5-bromo-2-fluorophenyl)-butyl]-amide, (S)-1-(4-fluorophenyl)-5-trifluoromethyl-1,5,6,7-tetrahydro-pyrazolo[4,3-b]pyridine-4-carboxylic acid [(S)-1-(3-bromo-4-methoxy-phenyl)-propyl]-amide, (S)-1-(4-fluorophenyl)-5-trifluoromethyl-1,5,6,7-tetrahydro-pyrazolo[4,3-b]pyridine-4-carboxylic acid [(S)-1-(4-bromo-3-methoxy-phenyl)-propyl]-amide, (S)-1-(4-fluorophenyl)-5-trifluoromethyl-1,5,6,7-tetrahydro-pyrazolo[4,3-b]pyridine-4-carboxylic acid [(S)-1-(3-bromo-5-fluorophenyl)-butyl]-amide The following compound is synthesized in similar fashion from intermediate M:

Compound 93.

The following compound is synthesized in similar fashion from intermediate Q:

Compounds 111, 112 and 113.

The following compound is synthesized in similar fashion from intermediate S:

Compound 103.

The following compound is synthesized in similar fashion from intermediate U:

Compound 76, 78, 79, 83.

The following compound is synthesized in similar fashion from intermediate V:
Compound 102.

Example 10

Synthesis of 1-(4-Fluorophenyl)-4-[(S)-1-(2-methanesulfonyl-pyridin-4-yl)-butylcarbamoyl]-4,5,6,7-tetrahydro-1H-pyrazolo[4,3-b]pyridine-6-carboxylic acid ethyl ester (Compound 114)

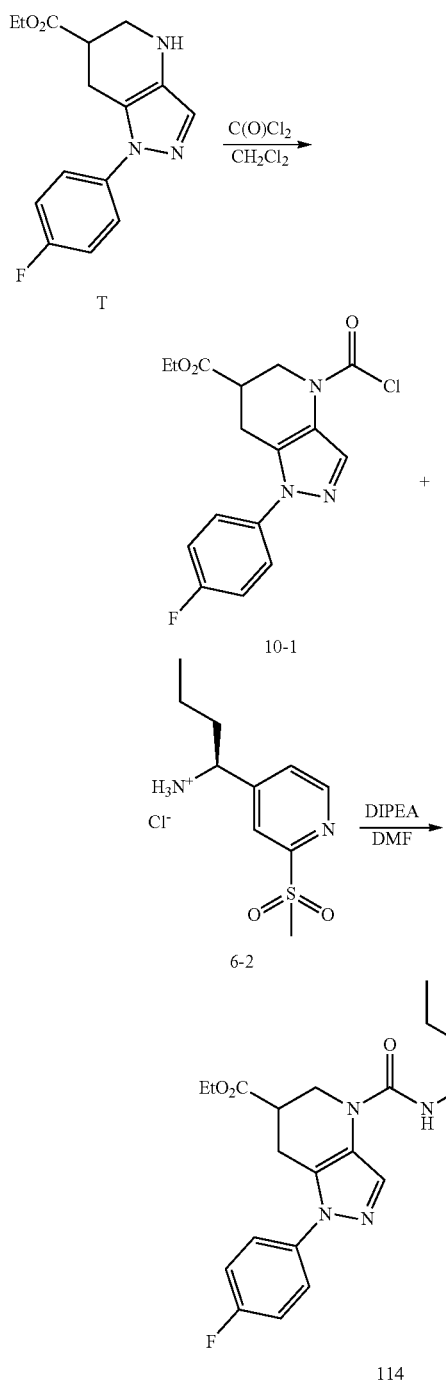

To a chilled (0° C.) solution of T (300.0 mg, 1.04 mmol) in DCM (7 mL) is added saturated aqueous $NaHCO_3$ (2 mL) followed by a solution of 20% phosgene (635 µL, 1.20 mmol) in toluene. After 1 hour, the reaction is diluted with water (20 mL) and extracted with DCM (2×20 mL). The combined organic layers are washed with brine (20 mL), dried over $Na_2SO_4$, filtered and concentrated to provide 10-1.

To a solution of 10-1 (360 mg, 1.02 mmol) in DMF (6 mL) is added 6-2 (291 mg, 1.10 mmol) and DIPEA (524 µL, 3.01 mmol). After 18 hours, the reaction is quenched with saturated aqueous $NH_4Cl$ (20 mL) and extracted with EtOAc (2×25 mL). The combined organics are washed with brine (2×15 mL), dried with $Na_2SO_4$ and concentrated. The residue is purified by silica gel chromatography using a gradient of 30-80% EtOAc in heptane to provide the title compound.

Example 11

Synthesis of 1-(4-Fluorophenyl)-4-[(S)-1-(2-methanesulfonyl-pyridin-4-yl)-butylcarbamoyl]-4,5,6,7-tetrahydro-1H-pyrazolo[4,3-b]pyridine-6-carboxylic acid (Compound 115)

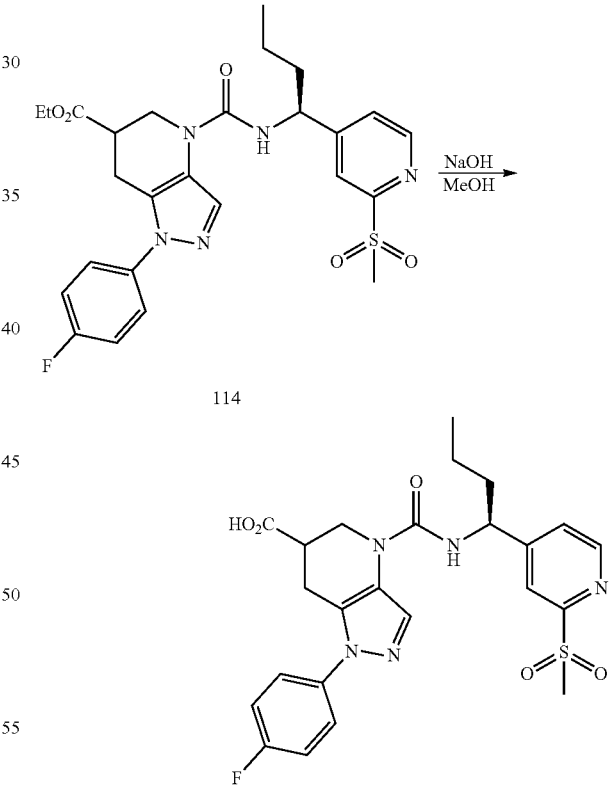

To a stirred solution of 114 (310 mg, 0.57 mmol) in MeOH (7 mL) is added 2M aqueous NaOH (3 mL). After 4 hours, the methanol is concentrated and the aqueous solution is acidified with 2N HCl solution to pH=4 and extracted with EtOAc (25×2). The combined organic layers are washed with brine (20 mL), dried over $Na_2SO_4$ and concentrated to provide the title compound.

Example 12

Synthesis of 1-(4-Fluorophenyl)-1,5,6,7-tetrahydro-pyrazolo[4,3-b]pyridine-4,6-dicarboxylic acid 4-{[(S)-1-(2-methanesulfonyl-pyridin-4-yl)-butyl]-amide}6-methylamide (Compound 117)

Example 13

Synthesis of 1-{(R)-1-[1-(4-fluorophenyl)-5-methyl-1,5,6,7-tetrahydro-pyrazolo[4,3-b]pyridine-4-carbonyl]-2-methyl-1-propyl}-3-(2-hydroxy-2-methyl-propyl)-urea (Compound 118)

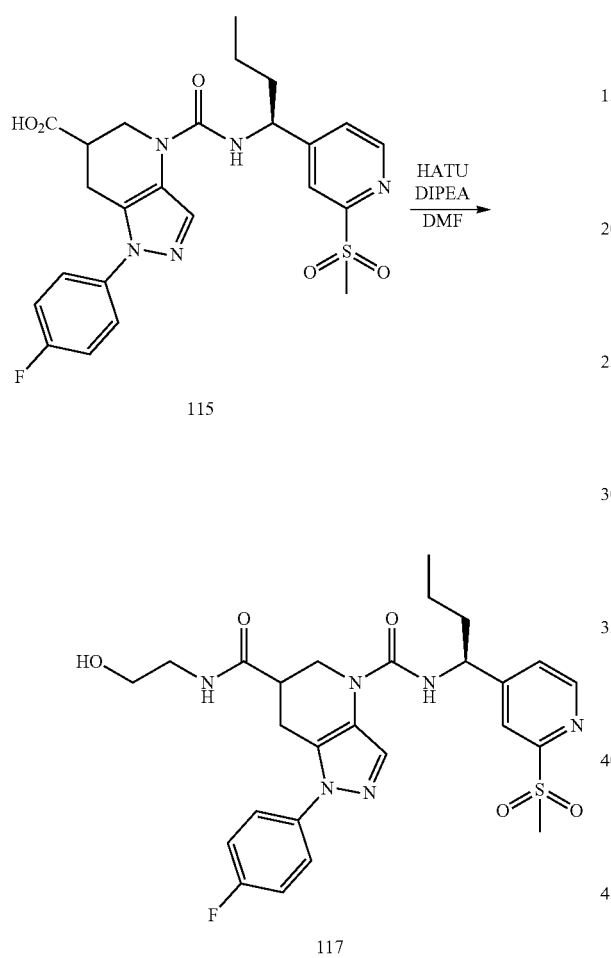

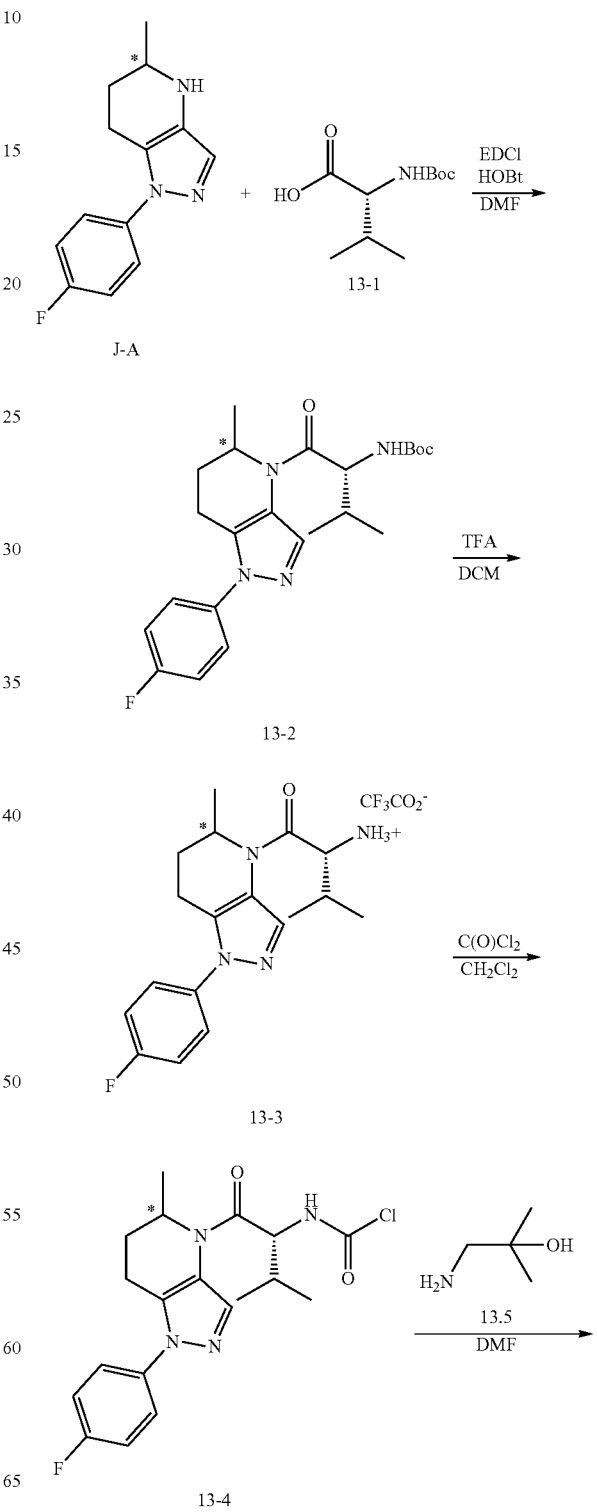

To a solution of 115 (70.0 mg, 0.14 mmol) in DMF (4 mL) is added HATU (53.2 mg, 0.14 mmol) and DIPEA (45 µL, 0.26 mmol). After 10 minutes, ethanolamine (11.0 mg, 0.18 mmol) is added. After 18 hours, the reaction is quenched with water (15 mL) and the mixture is extracted with EtOAc (3×15 mL). The combined organic layers are washed with brine (2×10 mL), dried over $Na_2SO_4$ and concentrated. The residue is purified by reversed phase prep-HPLC. The combined fractions from the column are concentrated and the aqueous solution is made basic with saturated aqueous $NaHCO_3$ and extracted with EtOAc (3×5 mL). The combined organic layers are dried over $Na_2SO_4$ and concentrated to provide the title compound.

The following compound is synthesized in similar fashion from 115:

Compound 116.

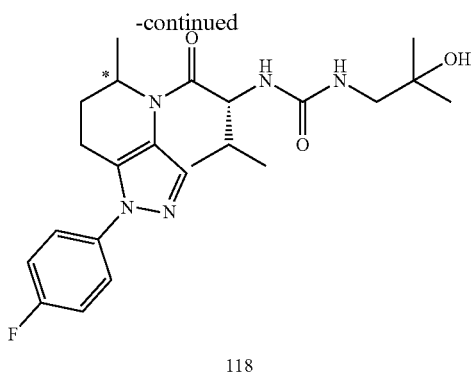

118

To a stirred solution of the 13-1 (155 mg, 0.713 mmol), J-A (150 mg, 0.65 mmol) and HOBt (219 mg, 1.62 mmol) in DMF (5 mL) is added with EDCI (274 mg, 1.43 mmol). After 30 minutes, DIPEA (450 µL) is added. After 5 days, the mixture is concentrated, diluted with EtOAc (300 mL), and washed with 1 N NaOH (3×100 mL), saturated aqueous NH$_4$Cl (2×100 mL), saturated aqueous NaHCO$_3$ (100 mL), and brine (100 mL). The organic layer is dried over magnesium sulfate, filtered and concentrated. The residue is purified by silica gel chromatography using a gradient of 0-10% MeOH in DCM to provide 13-2.

To a stirred solution of 13-2 (153 mg, 0.355 mmol) in DCM (4 mL) is added TFA (1.0 mL, 13 mmol). After 16 hours, the mixture is concentrated to provide 13-3.

To a chilled (0° C.) solution of 13-3 (196 mg, 0.350 mmol) in DCM (5 mL) is added saturated aqueous NaHCO$_3$ (5 mL) followed by a 20% solution of phosgene (280 µL, 0.53 mmol) in toluene. After 3 hours, the aqueous layer is separated and extracted with DCM (3×2 mL). The combined organic layers are dried over magnesium sulfate, filtered and concentrated to provide 13-4.

To a stirred solution of 13-4 (122 mg, 0.310 mmol) in DMF (2 mL) is added 13-5 (41.5 mg, 0.466 mmol) and DIPEA (217 µL, 1.24 mmol). After 20 hours, the mixture is partitioned between DCM (20 mL) and saturated aqueous NH$_4$Cl (20 mL). The organic layer is extracted with brine (20 mL), dried over magnesium sulfate, filtered and concentrated. The residue is purified by RP-HPLC on a C18 semi-preparative column using a gradient of 5-95% MeCN in H$_2$O containing 0.1% TFA over 20 minutes. The combined desired fractions are neutralized with saturated aqueous NaHCO$_3$, concentrated to remove MeCN, and extracted with EtOAc (3×100 mL). The combined organic layers are washed with brine (50 mL), dried over magnesium sulfate, filtered and concentrated to provide the title compound.

Assessment of Biological Properties

Compounds are assessed for the ability to block the interaction of CCR1 and MIP-1α in a functional cellular assay measuring calcium flux in CCR1 transfected cells.

Method A: Non-adherent cells purchased from Chemicon Corporation (HTS005C), stably expressing recombinant CCR1 and G-alpha-16 are grown in RPMI 1640 medium (Mediatech 10-080-CM) supplemented with 10% heat-inactivated FBS, 0.4 mg/mL Geneticin and penicillin/streptomycin. On the day of the assay, the cells are transferred to a beaker and dye-loaded in bulk using a Fluo-4 NW Calcium Assay Kit with probenecid (Invitrogen F36205) at 0.8E6 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells are allowed to incubate 1 hour in the dark at room temperature. The plates are transferred to the FLIPR TETRA where MIP-1 alpha in 1% BSA is added at the EC80 final concentration. Wells+/−MIP-1 alpha containing diluted DMSO instead of compound serve as the controls. Intracellular calcium flux is recorded on the FLIPR TETRA, using excitation at 470/495 nm and emission at 515/575 nm. Data are analyzed using Activity Base software.

Method B: Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells+/−MIP-1alpha containing diluted DMSO instead of compound serve as the controls. Data are analyzed using Activity Base software.

In general, the preferred potency range (IC$_{50}$) of compounds in one or both of the above assays is between 0.1 nM and 3 µM, and the most preferred potency range is 0.1 nM to 50 nM. Results from both assays are comparable as shown by selected compounds.

Representative compounds of the invention have been tested in one or both of the above assay variations and have shown activity as CCR1 antagonists.

TABLE II

| Example# | Method A IC$_{50}$ (nM) | Method B IC$_{50}$ (nM) |
|---|---|---|
| 2 |  | 453 |
| 3 |  | 126 |
| 4 |  | 283 |
| 5 |  | 90 |
| 6 |  | 125 |
| 7 |  | 183 |
| 8 |  | 266 |
| 9 |  | 108 |
| 10 |  | 266 |
| 11 |  | 610 |
| 12 |  | 138 |
| 13 |  | 45 |
| 14 |  | 102 |
| 15 |  | 115 |
| 16 |  | 12 |
| 17 |  | 1 |
| 18 |  | 131 |
| 19 |  | 395 |
| 20 |  | 91 |
| 21 |  | 1 |
| 22 | 22 | 5 |
| 23 | 31 | 22 |
| 24 | 0.6 |  |
| 25 | 51 | 65 |
| 26 | 6 | 4 |
| 27 |  | 68 |

TABLE II-continued

| Example# | Method A IC$_{50}$ (nM) | Method B IC$_{50}$ (nM) |
|---|---|---|
| 28 | 40 | 10 |
| 29 |  | 16 |
| 30 |  | 94 |
| 31 | 3 | 1 |
| 32 |  | 34 |
| 33 | 19 |  |
| 34 | 20 |  |
| 35 | 4 |  |
| 36 | 3 | 3 |
| 37 |  | 40 |
| 38 | 11 | 2 |
| 39 | 0.2 | 0.4 |
| 40 | 33 | 3 |
| 41 | 6 | 2 |
| 42 | 0.4 | 0.2 |
| 43 |  | 25 |
| 44 |  | 18 |
| 45 | 1 | 0.6 |
| 46 | 0.2 | 0.2 |
| 47 | 0.4 | 0.2 |
| 48 | 19 | 2 |
| 49 | 12 | 2 |
| 50 | 4 | 0.9 |
| 51 | 14 | 3 |
| 52 |  | 128 |
| 53 |  | 1280 |
| 54 |  | 684 |
| 55 | 13 | 12 |
| 56 | 10 | 6 |
| 58 |  | 84 |
| 59 | 0.4 | 0.6 |
| 60 | 0.5 | 0.3 |
| 61 | 12 | 8 |
| 62 | 1 | 1 |
| 63 | 14 | 14 |
| 64 |  | 1850 |
| 65 |  | 330 |
| 67 |  | 194 |
| 68 |  | 205 |
| 69 |  | 11 |
| 70 |  | 5 |
| 71 |  | 0.3 |
| 72 |  | 344 |
| 75 |  | 640 |
| 77 |  | 37 |
| 78 |  | 4 |
| 79 |  | 2 |
| 80 |  | 31 |
| 81 |  | 4 |
| 82 |  | 23 |
| 83 |  | 1258 |
| 84 |  | 14 |
| 85 |  | 23 |
| 86 |  | 2 |
| 87 |  | 10 |
| 88 |  | 52 |
| 89 |  | 34 |
| 90 |  | 6 |
| 91 |  | 1442 |
| 93 |  | 18 |
| 94 |  | 57 |
| 95 |  | 6 |
| 96 |  | 7 |
| 97 |  | 5 |
| 98 |  | 1572 |
| 99 |  | 1500 |
| 102 |  | 0.6 |
| 103 |  | 0.7 |
| 104 |  | 57 |
| 105 |  | 5 |
| 106 |  | 11 |
| 107 |  | 8 |
| 108 |  | 9 |
| 109 |  | 11 |
| 111 |  | 22 |
| 112 |  | 65 |
| 114 |  | 0.7 |
| 115 |  | 23 |
| 116 |  | 1 |
| 117 |  | 1 |

Method of Use

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) JBC 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) Ann Neurol 54 p. 638), asthma (Jouber et al. (2008) J. Immun 180 p. 1268), chronic kidney disease (Topham et al. (1999) J. Clin. Invest. 104 p. 1549), sepsis (He et al. (2007) Am J. Physio 292 p. G1173), autoimmune myocarditis (Futamats et al. (2006) J Mol Cell Cardiology 40 p. 853) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg/kg to about 100 mg/kg of body weight per dosage of a compound of the invention; preferably, from about 0.1 mg/kg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I)

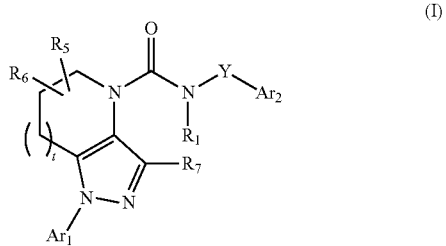

wherein
t is 0, 1 or 2 such that the nitrogen containing ring in the formula (I) can be 5, 6 or 7 membered ring fused to the pyrazole ring to form a bicyclic ring system;
$Ar_1$ is carbocycle, heteroaryl or heterocyclyl each optionally substituted by one to three $R_a$;
$Ar_2$ is carbocycle, heteroaryl or heterocyclyl, each optionally substituted by one to three $R_b$;
Y is a bond or $(CR_2R_3)_m$;
$R_1$ is hydrogen, $C_{1-6}$ alkyl or $C_{1-6}$ alkoxy$C_{1-6}$ alkyl;
$R_2$, $R_3$ are each independently hydrogen, $C_{1-6}$ alkyl or $C_{2-6}$ alkenyl, wherein the $C_{1-6}$ alkyl or $C_{2-6}$ alkenyl is optionally partially or fully halogenated or substituted with one to three groups independently selected from hydroxyl, $-CO_2C_{1-6}$ alkyl, $-C(O)N(R_e)(R_f)$, $-N(R_e)(R_f)$, and heterocyclyl;
or $R_2$, $R_3$ can form a carbocycle, or heterocycle each optionally substituted by one to three $R_g$ provided that $R_2$ and $R_3$ are on the same carbon atom,
$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4-S(O)_m-NH-$, $R_4-NH-S(O)_m-$, aryl or carboxyl;
$R_b$ is hydroxyl, carboxyl, halogen, $-(CH_2)_n-CN$, $-(CH_2)_n-CO_2C_{1-6}$alkyl, nitro, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)-, $-(CH_2)_n-NR_cR_d$, $R_4-S(O)_m(CH_2)_{0-1}-$, $R_4-S(O)_m-NR_e-$, $R_4-NR_e-S(O)_m(CH_2)_{0-1}-$, $-NR_f-C(O)-R_e$, $-(CH_2)_x-C(O)-(CH_2)_n-NR_cR_d$, heterocyclyl, aryl or heteroaryl, each $R_b$ is optionally substituted with 1 to 3 halogen, $C_{1-6}$ alkyl, $C_{1-6}$ acyl, $C_{1-6}$ alkoxycarbonyl, $C_{1-6}$ alkyl-$S(O)_m-$, aryl or carboxyl;
each $R_c$, $R_d$ are independently hydrogen, $C_{1-6}$ alkyl, $C_{1-6}$ acyl, $C_{3-10}$ cycloalkyl, $C_{1-6}$ alkoxy, hydroxyC$_{1-6}$ alkyl, $C_{1-6}$ alkylC$_{1-6}$ alkoxy, $C_{1-6}$ alkylsulfonyl, $C_{1-6}$ alkoxycarbonylC$_{0-3}$alkyl or $-(CH_2)_n-NR_eR_f$;
each $R_e$, $R_f$ are independently hydrogen, $C_{1-6}$ alkyl, $C_{3-10}$ cycloalkyl, $C_{1-6}$ alkoxy, $C_{1-6}$ alkoxyC$_{1-6}$alkyl, mono- or di-C$_{1-6}$alkylaminoC$_{1-6}$alkyl, hydroxyC$_{1-6}$ alkyl or $C_{1-6}$ acyl;
$R_g$ is $C_{1-6}$ alkyl, wherein the $C_{1-6}$ alkyl is optionally partially or fully halogenated, $C_{2-6}$ alkenyl, carbocycle, $C_{1-6}$ alkoxy, hydroxyC$_{1-6}$ alkyl, cyano, halogen, hydroxyl, $-(CH_2)_n-CO_2C_{1-6}$ alkyl, $-(CH_2)_n-C(O)N(R_e)(R_f)$, $-(CH_2)_n-N(R_e)(R_f)$ or oxo;
$R_4$ is hydrogen, heterocyclyl or $C_{1-6}$ alkyl optionally substituted by $C_{1-4}$ alkoxy, hydroxyl, heterocyclyl, heteroaryl or aryl each ring is further optionally substituted with 1 to 3 $C_{1-6}$ alkyl, $C_{3-6}$cycloalkyl, $C_{1-6}$alkoxy, halogen, hydroxyl, oxo, carboxyl, $-C(O)NR_eR_f$, amino, mono- or di-$C_{1-6}$ alkylamino, $C_{1-6}$ alkoxycarbonyl or $C_{1-6}$ acylamino;
each n, x are independently 0-3;
each m is independently 0-2;
$R_5$ is covalently attached at the 5, 6 or 7 position and is hydrogen, $C_{1-6}$ alkyl, $C_{3-6}$cycloalkyl, heterocyclyl $(CH_2)_{0-1}$, mono- or di-$C_{1-6}$ alkylamino, mono- or di-$C_{1-6}$alkylamino$(CH_2)_{2-3}$N$(R_e)-$, $C_{1-6}$alkylCO$_2-$, carboxyl, $N(R_e)(R_f)-C(O)-$, cyano, $R_4-S(O)_m-$, $R_4-NR_e-S(O)_m-$, aryl or heteroaryl each optionally substituted with $C_{1-6}$ alkyl, $C_{3-6}$cycloalkyl, $C_{1-6}$alkoxy, halogen, hydroxyl, oxo, carboxyl, $-C(O)NR_eR_f$, amino, mono- or di-$C_{1-6}$ alkylamino, $C_{1-6}$ alkoxycarbonyl or $C_{1-6}$ acylamino;
$R_6$ is covalently attached at the 5, 6 or 7 position and is hydrogen, $C_{1-6}$ alkyl, each optionally substituted with 1 to 3 $C_{1-6}$ alkyl, or halogen;
or $R_5$, $R_6$ can form a $C_{3-6}$ cycloalkyl ring provided that $R_5$ and $R_6$ are on the same carbon atom,
$R_7$ is hydrogen or $C_{1-6}$ alkyl;
or a pharmaceutically acceptable salt thereof;
wherein each alkyl group defined above can be optionally partially or fully halogenated.

2. The compound according to claim 1 and wherein
$Ar_1$ is aryl substituted by one to three $R_a$;
$Ar_2$ is aryl or heteroaryl, each optionally substituted by one to three $R_b$;
Y is $(CR_2R_3)_m$;
$R_1$ is hydrogen;
each $R_e$, $R_f$ are independently hydrogen, $C_{1-6}$ alkyl or hydroxy$C_{1-6}$ alkyl;
$R_2$, $R_3$ are each independently hydrogen, $C_{1-6}$ alkyl or $C_{2-6}$ alkenyl, wherein the $C_{1-6}$ alkyl or $C_{2-6}$ alkenyl is optionally partially or fully halogenated,
or $R_2$, $R_3$ can form a $C_{3-7}$ cycloalkyl ring provided that $R_2$, $R_3$ are attached to the same carbon atom,
$R_5$ is hydrogen, $C_{1-6}$alkyl$CO_2$—, carboxyl, $N(R_e)(R_f)$—C(O)— or $C_{1-6}$ alkyl optionally partially or fully halogenated;
$R_6$ is hydrogen, $C_{1-6}$ alkyl;
$R_7$ is hydrogen.

3. The compound according to claim 2 and wherein
$Ar_1$ is phenyl substituted by one to three $R_a$;
$Ar_2$ is phenyl or heteroaryl chosen from furanyl, pyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, quinolinyl, isoquinolinyl, quinazolinyl, indazolyl, indolyl, isoindolyl, benzofuranyl, benzopyranyl, pyrrolopyridinyl and benzodioxolyl;
each optionally substituted by one to three $R_b$.

4. The compound according to claim 1 and wherein
$Ar_2$ is phenyl, benzyl, phenethyl or heteroaryl chosen from pyridinyl, pyrimidinyl, pyridazinyl and pyrazinyl;
each optionally substituted by one to three $R_b$.

5. The compound according to claim 4 and wherein
$Ar_2$ is phenyl, benzyl, phenethyl or pyridinyl;
each optionally substituted by one to three $R_b$.

6. The compound according to claim 5 and wherein
$R_b$ is halogen, $C_{1-5}$ alkyl optionally halogenated, $C_{1-5}$ alkoxy, hydroxyl, $R_4$—S(O)$_m$— or $R_4$—NR$_e$—S(O)$_m$—;
$R_4$ is morpholinyl, thiomorpholinyl, pyrrolidinyl, piperadinyl, piperazinyl, dioxalanyl, dioxanyl, tetrahydropyranyl, tetrahydrofuranyl or $C_{1-4}$ alkyl optionally substituted by $C_{1-4}$ alkoxy, morpholinyl, thiomorpholinyl, pyrrolidinyl, piperadinyl, piperazinyl, dioxalanyl, dioxanyl, tetrahydropyranyl or tetrahydrofuranyl;
$R_e$ is hydrogen or $C_{1-3}$ alkyl or hydroxy$C_{1-6}$ alkyl;
$R_2$, $R_3$ are each independently hydrogen or $C_{1-6}$ alkyl optionally partially or fully halogenated,
or $R_2$, $R_3$ can form a $C_{3-6}$ cycloalkyl ring provided that $R_2$, $R_3$ are attached to the same carbon atom.

7. The compound according to claim 6 and wherein
$R_b$ is halogen, $C_{1-3}$ alkyl optionally halogenated, $C_{1-3}$ alkoxy, hydroxyl, $R_4$—S(O)$_m$— or $R_4$—NR$_e$—S(O)$_m$—;
$R_4$ is $C_{1-3}$ alkyl substituted by $C_{1-3}$ alkoxy, morpholinyl or tetrahydropyranyl;
$R_2$, $R_3$ are each independently hydrogen or $C_{1-6}$ alkyl optionally partially or fully halogenated,
or $R_2$, $R_3$ can form a $C_{3-5}$ cycloalkyl ring provided that $R_2$, $R_3$ are attached to the same carbon atom.

8. The compound according to claim 7 and wherein
$Ar_1$ is phenyl substituted by one to three halogen;
$Ar_2$ is phenyl or pyridinyl;

$R_b$ is —OCH$_3$, —CH$_3$, F, Cl, Br, —CF$_3$, hydroxyl, —S(O)$_2$—CH$_3$, —S(O)$_2$—NH—CH$_3$, —S(O)$_2$—N(CH$_3$)$_2$, —S(O)$_2$—NH—(CH$_2$)$_2$—OCH$_3$, —S(O)$_2$—NH—CH(CH$_3$)—CH$_2$OH,

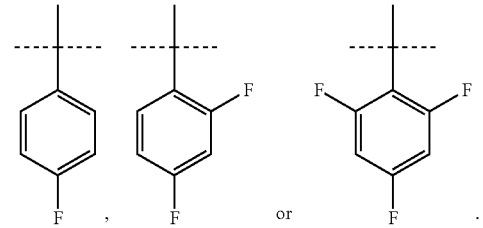

$R_2$, $R_3$ are each independently hydrogen, $C_{1-6}$ alkyl,
or $R_2$, $R_3$ can form a cyclopropyl ring provided that $R_2$, $R_3$ are attached to the same carbon atom,
$R_5$ is hydrogen, —CH$_3$, —CF$_3$, —C(O)$_2$CH$_2$CH$_3$, —C(O)NHCH$_3$ or —C(O)NH(CH)$_2$OH;
$R_6$ is hydrogen, —CH$_3$.

9. The compound according to claim 8 and wherein
$Ar_1$ is

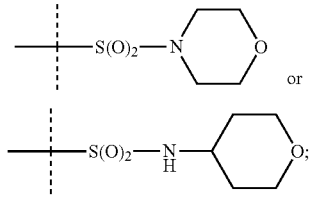

10. The compound according to claim 9 and wherein
$Ar_1$ is

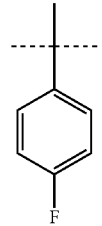

11. The compound according to claim 6 and wherein
$Ar_2$ is

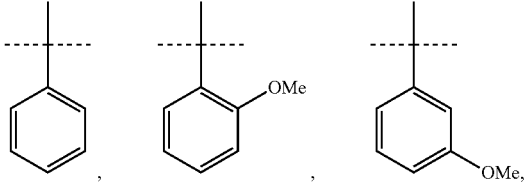

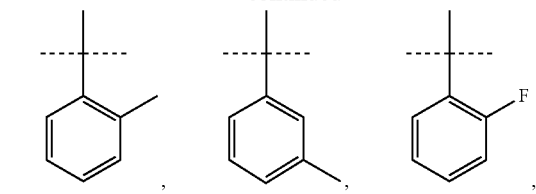
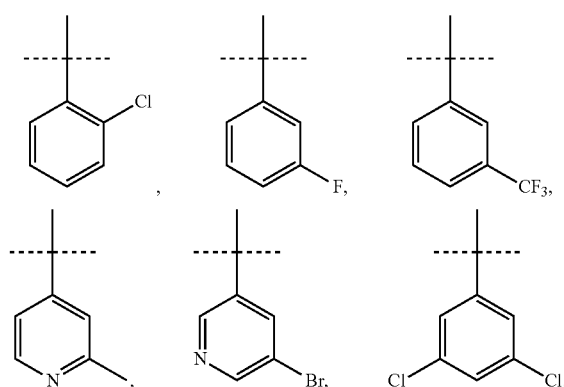
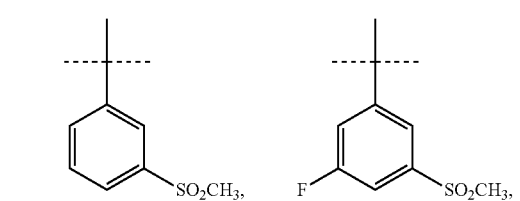
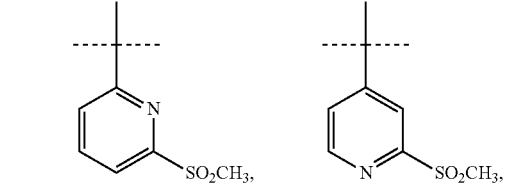
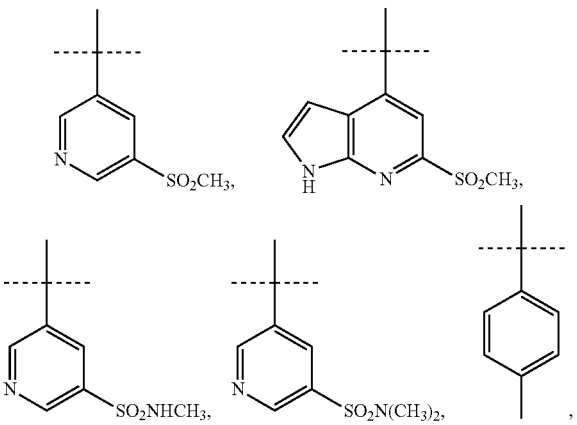
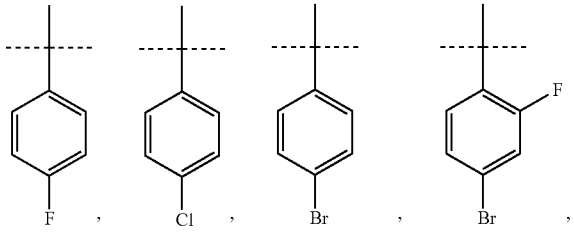
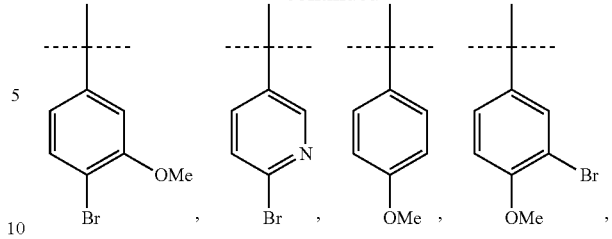
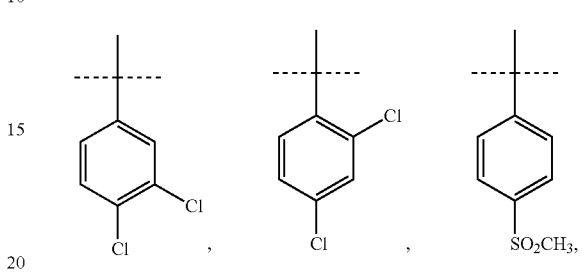
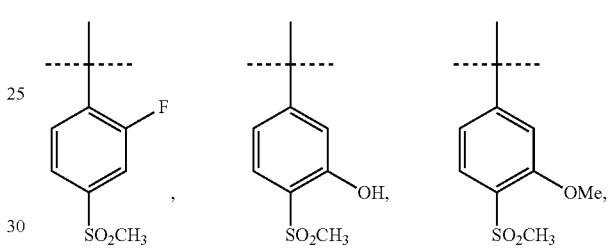
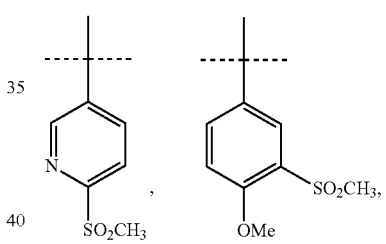
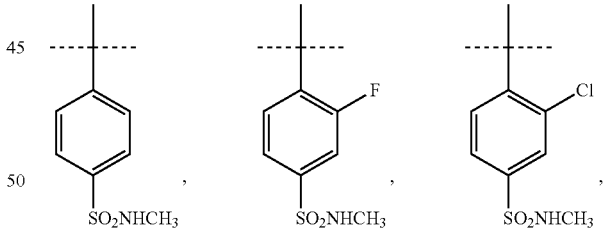
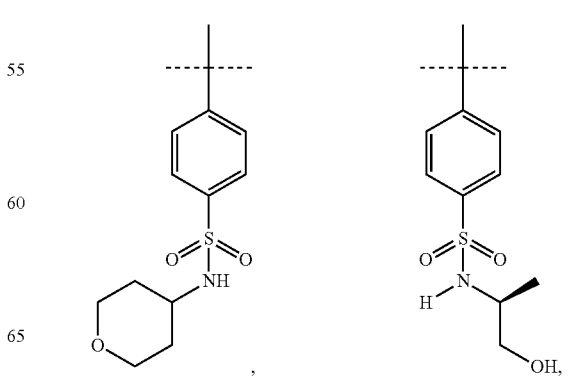

133
-continued
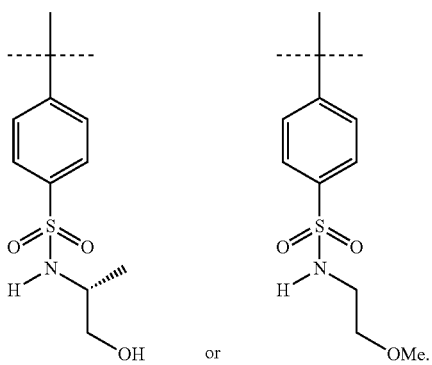
12. A compound chosen from
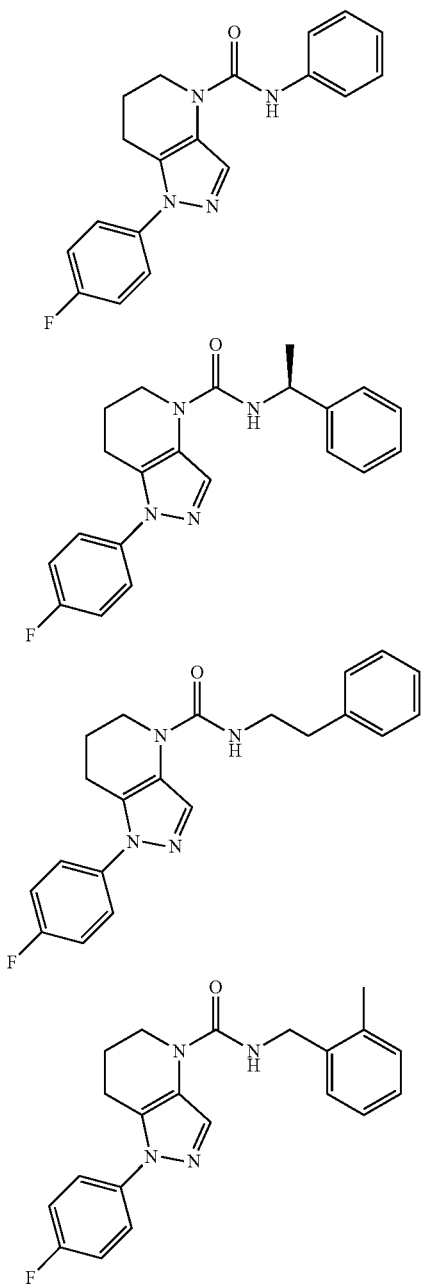
134
-continued
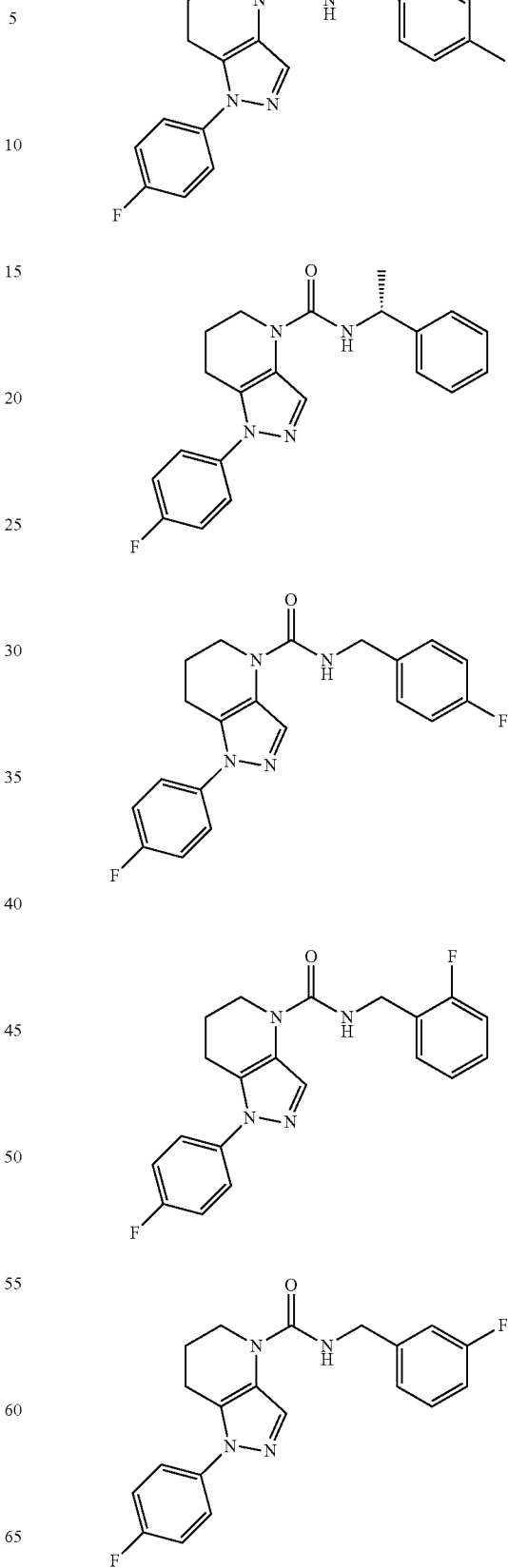

135
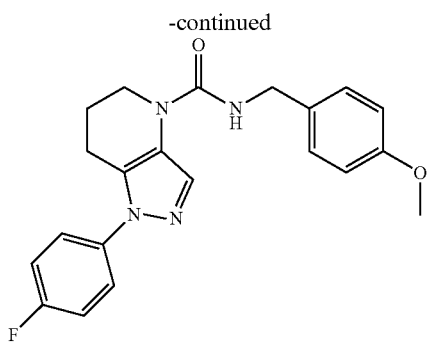
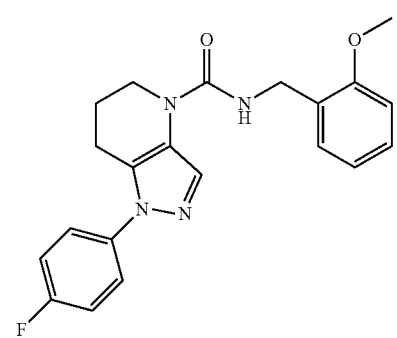
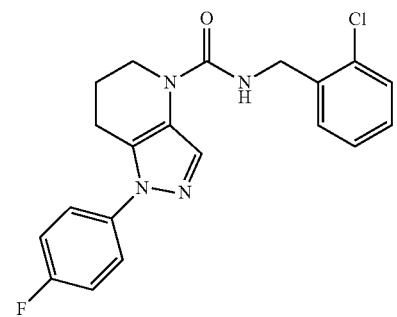
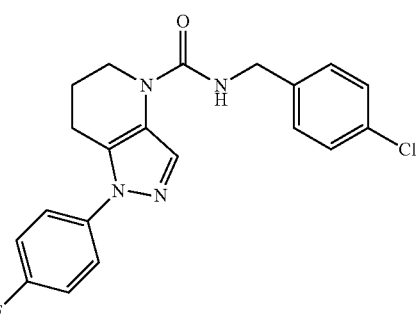
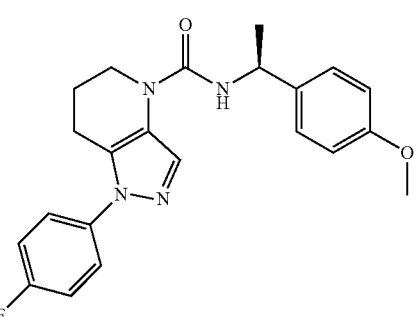
136
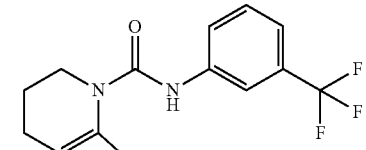
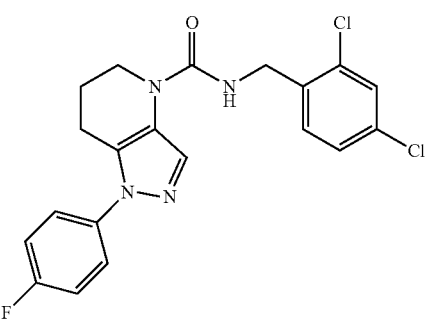
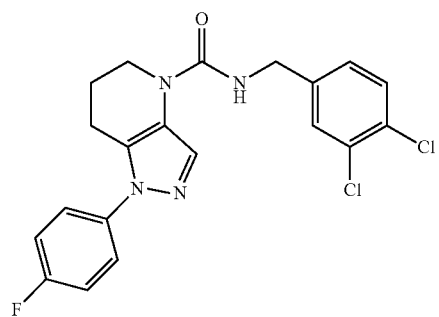
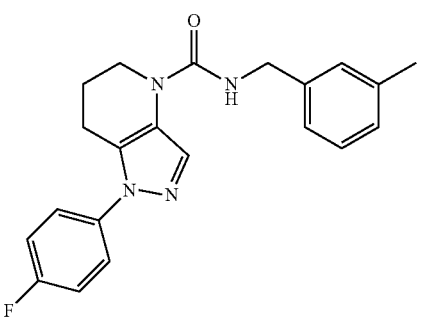
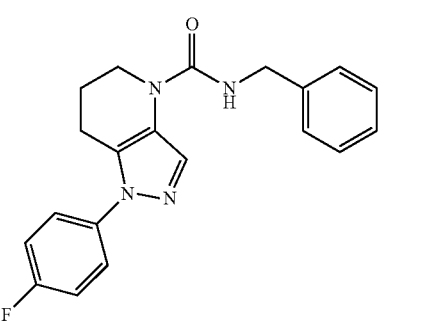

137
-continued
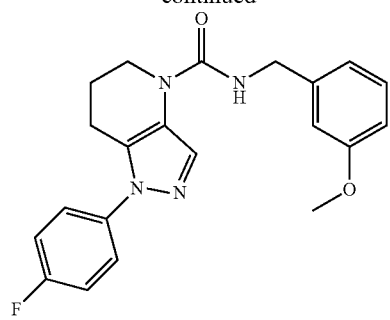
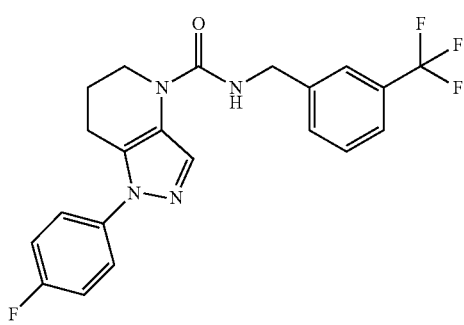
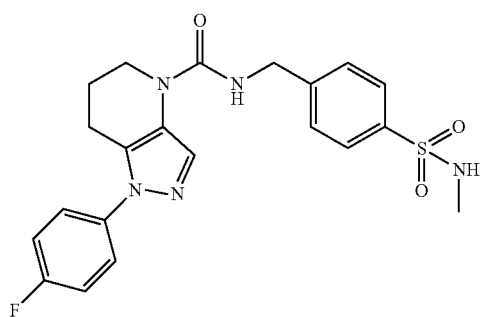
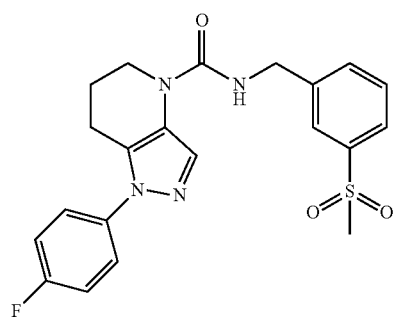
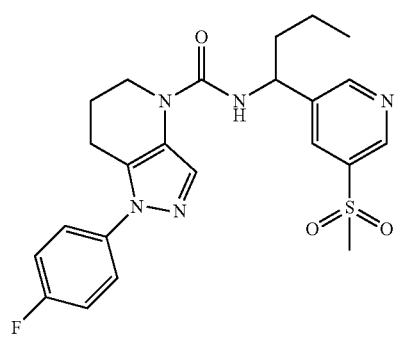
138
-continued
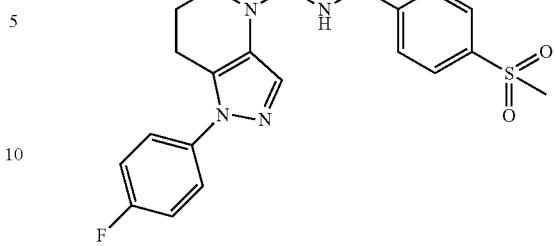
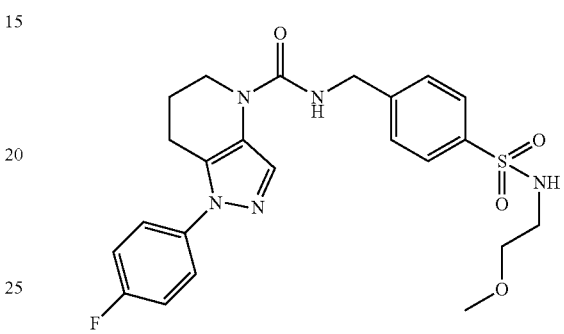
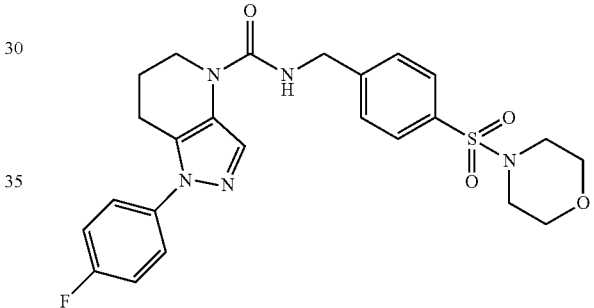
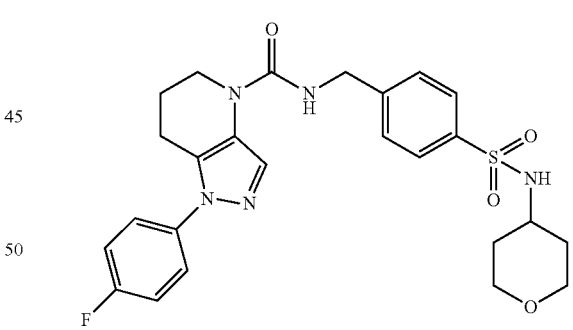
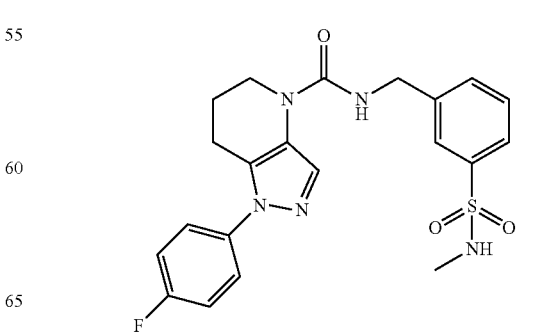

139
-continued
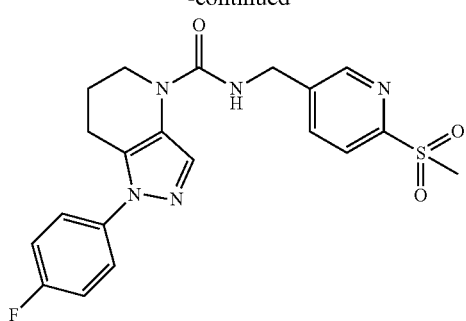
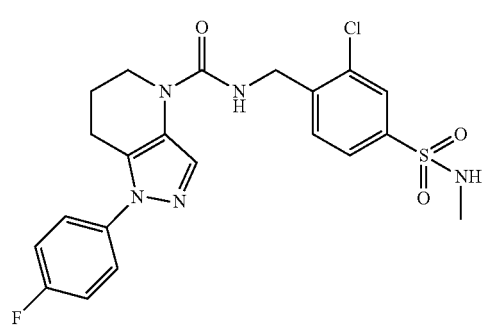
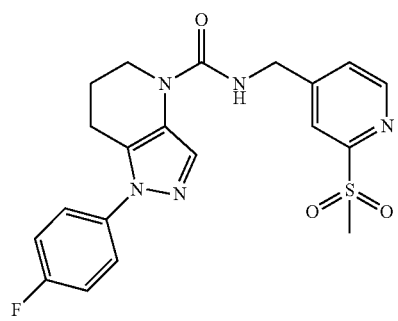
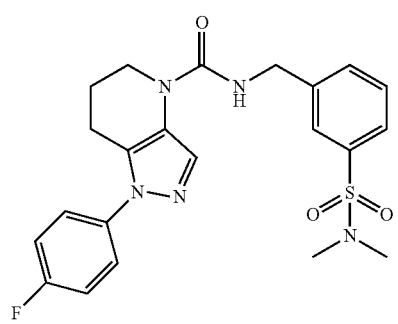
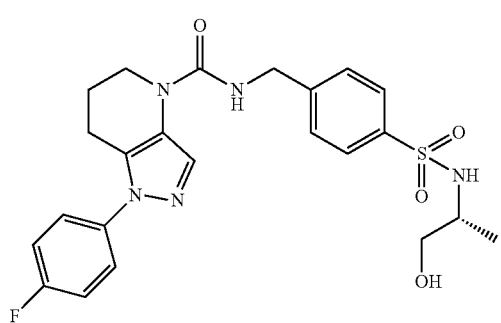
140
-continued
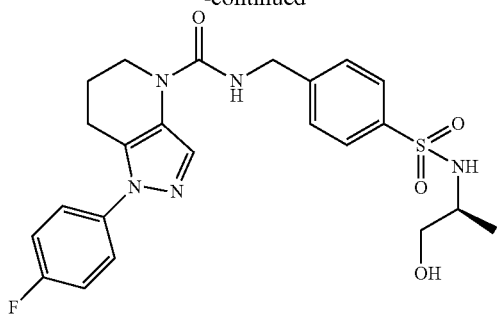
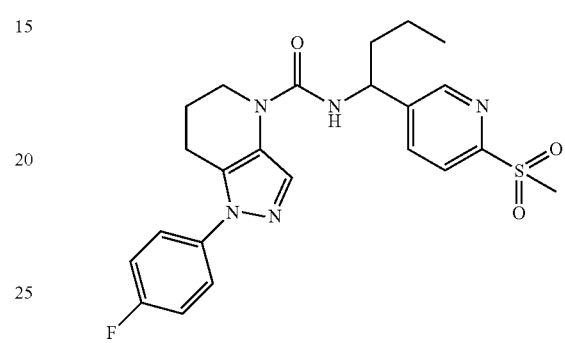
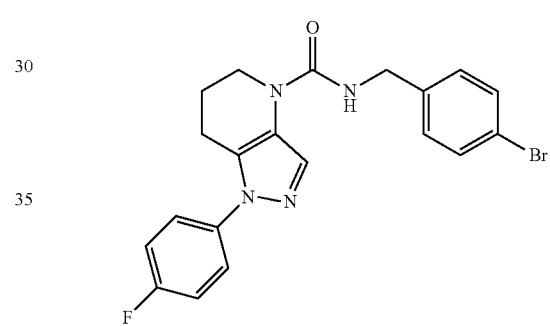
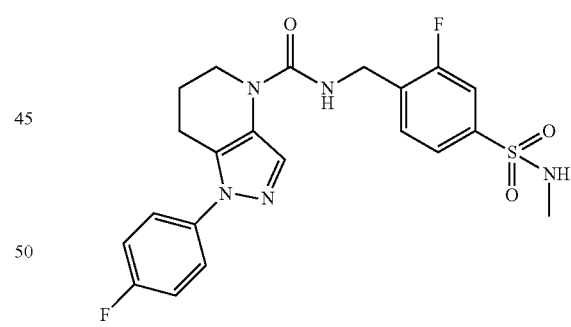
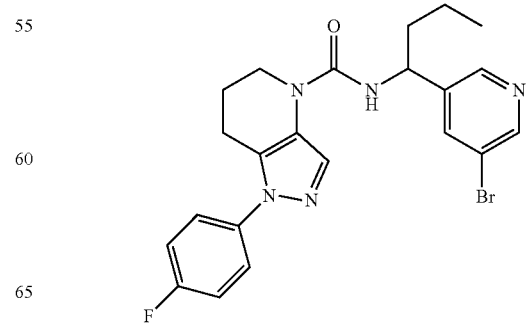

141
-continued
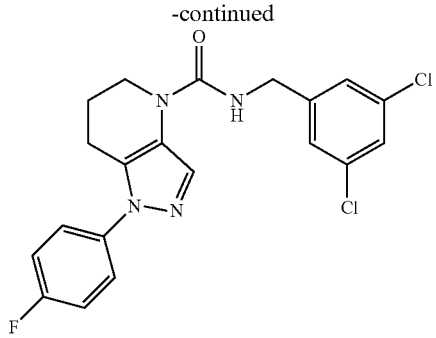
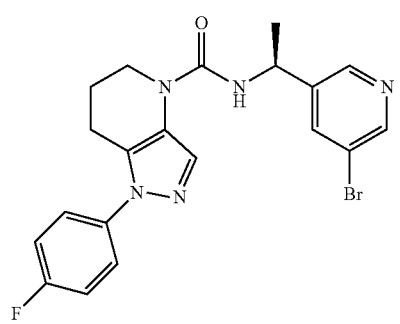
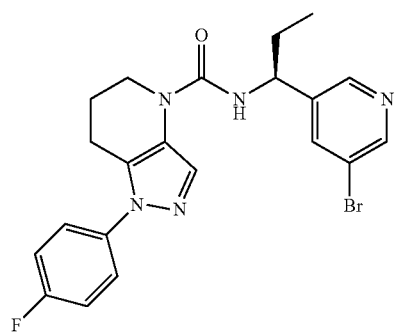
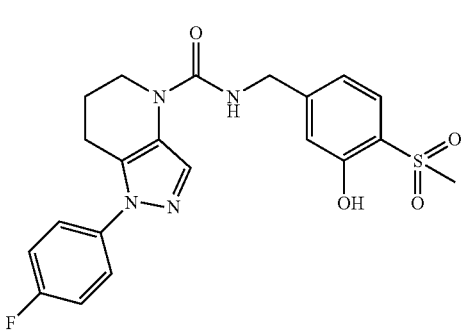
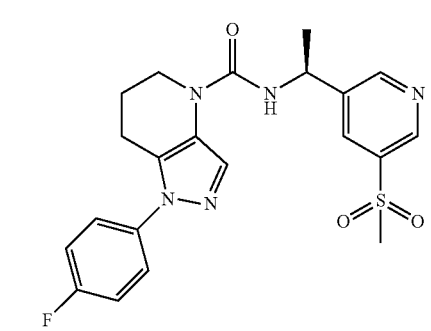
142
-continued
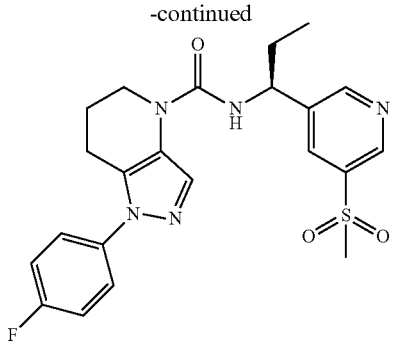
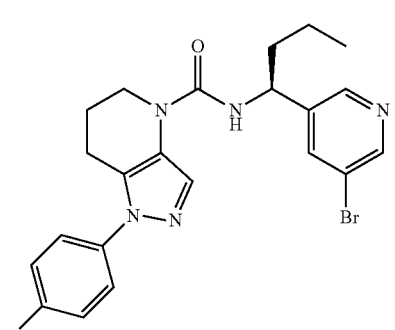
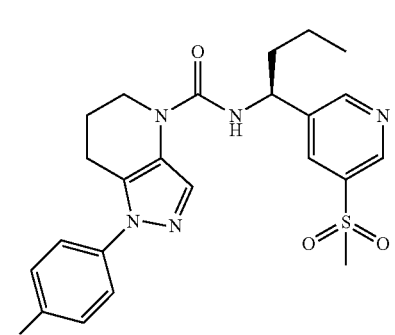
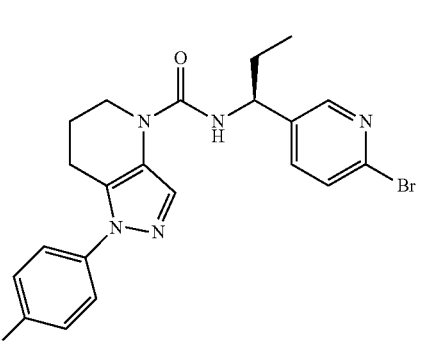
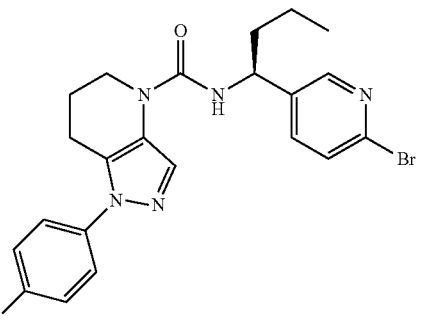

143
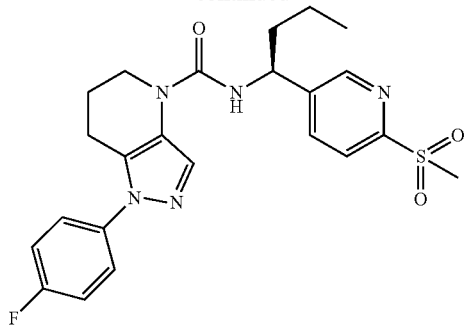
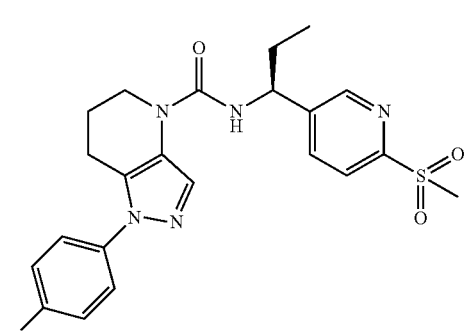
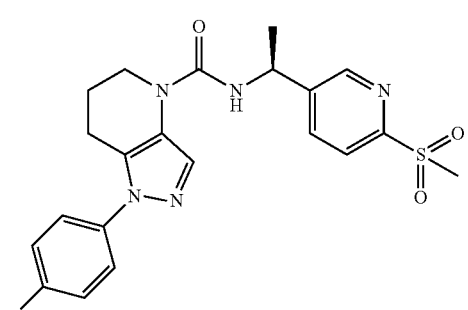
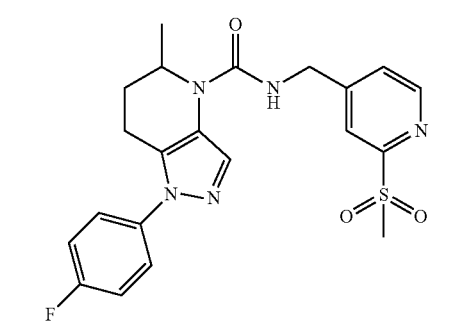
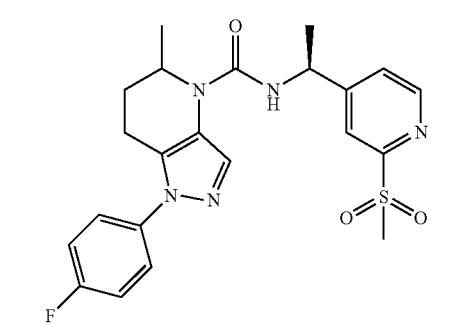
144
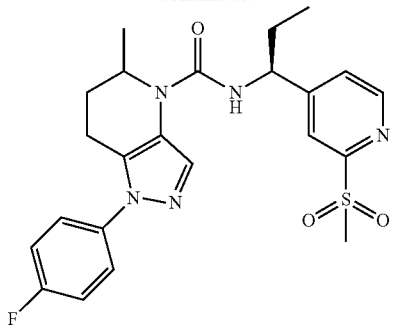
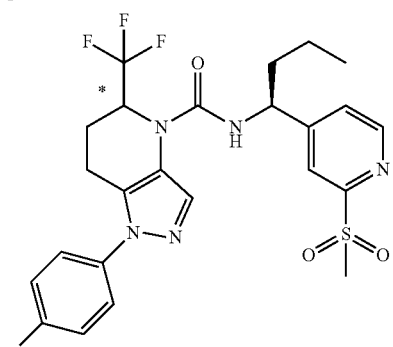
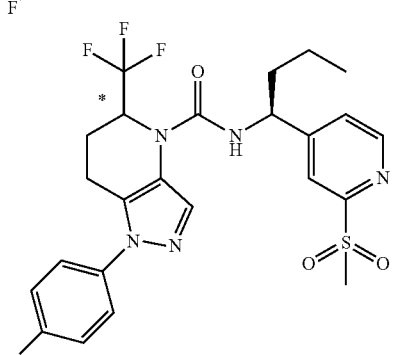
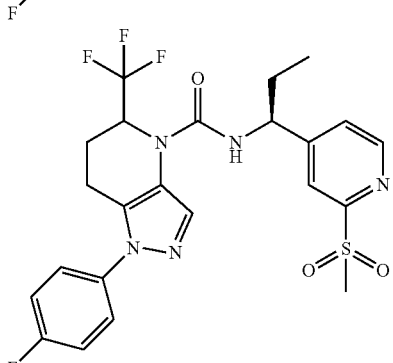
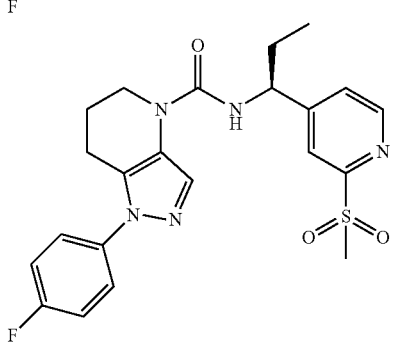

-continued
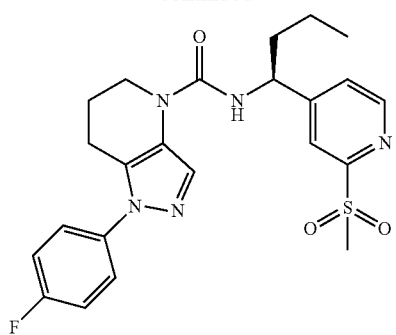
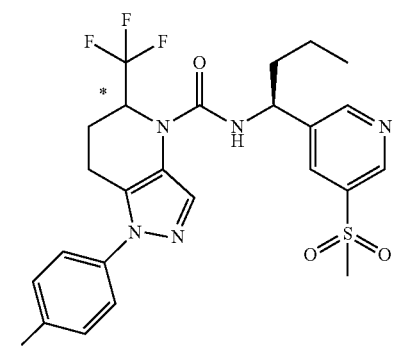
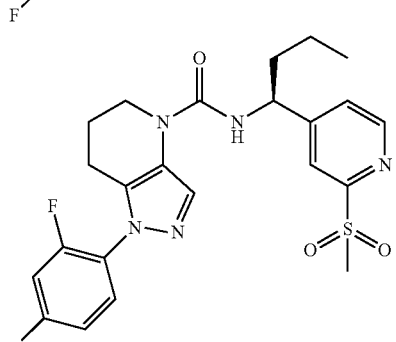
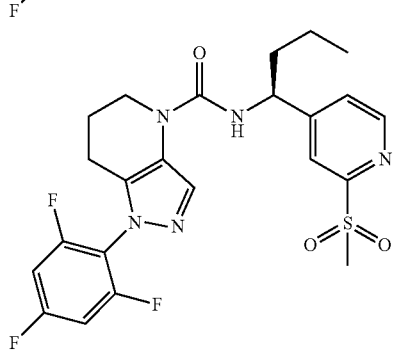
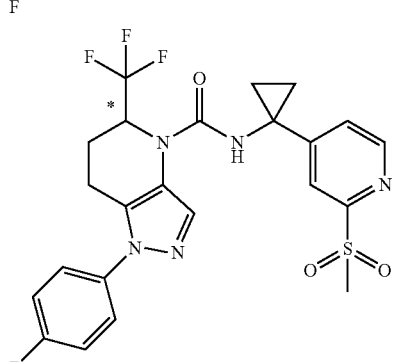
-continued
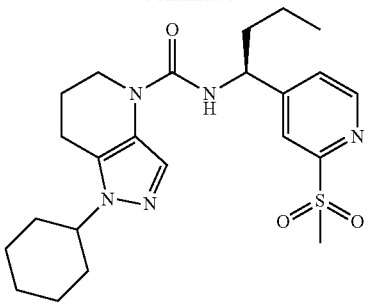
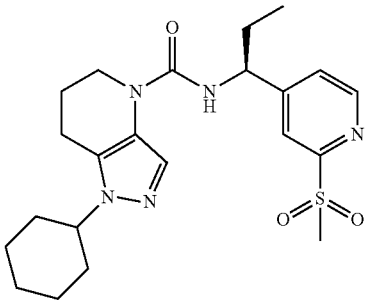
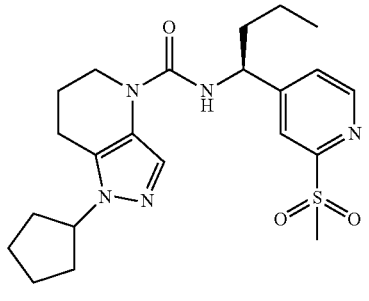
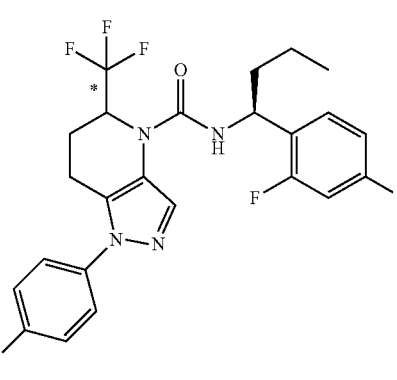
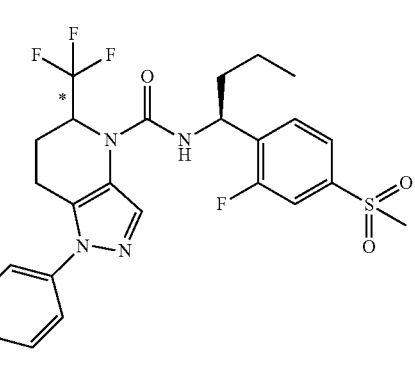

147
-continued
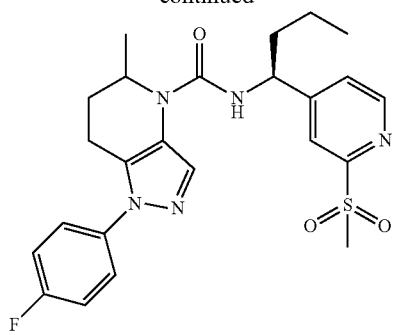
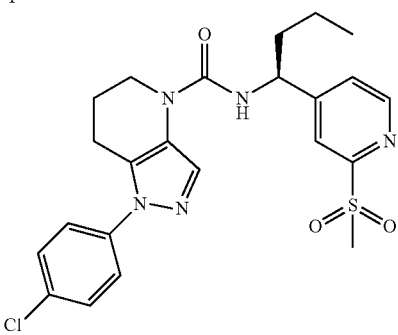
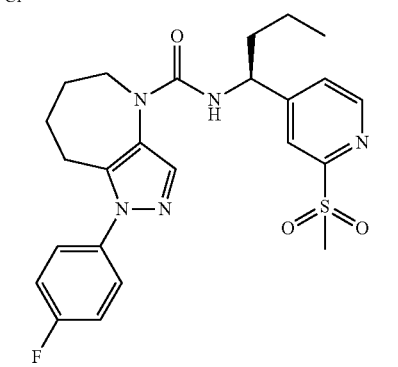
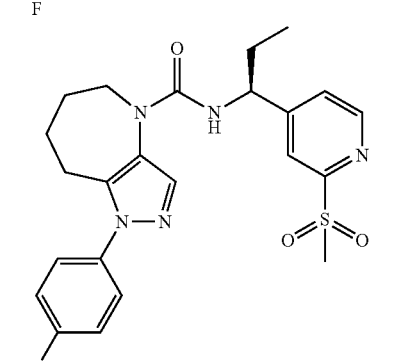
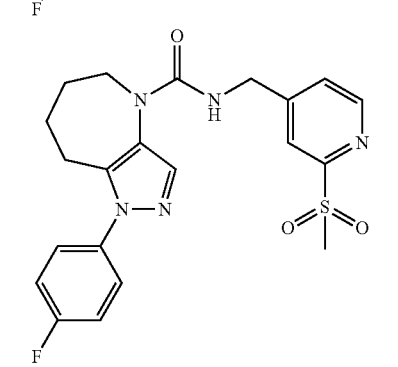
148
-continued
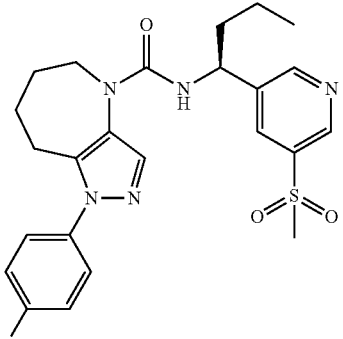
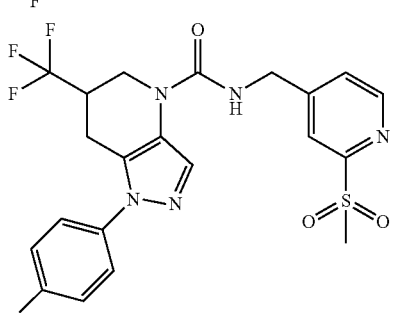
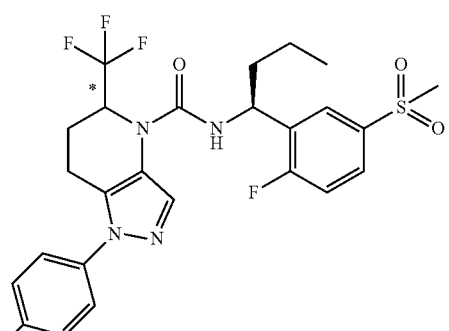
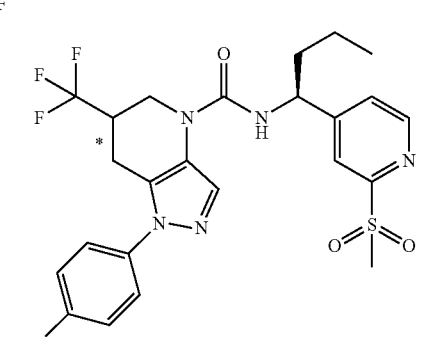
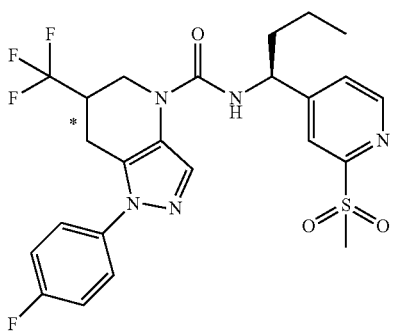

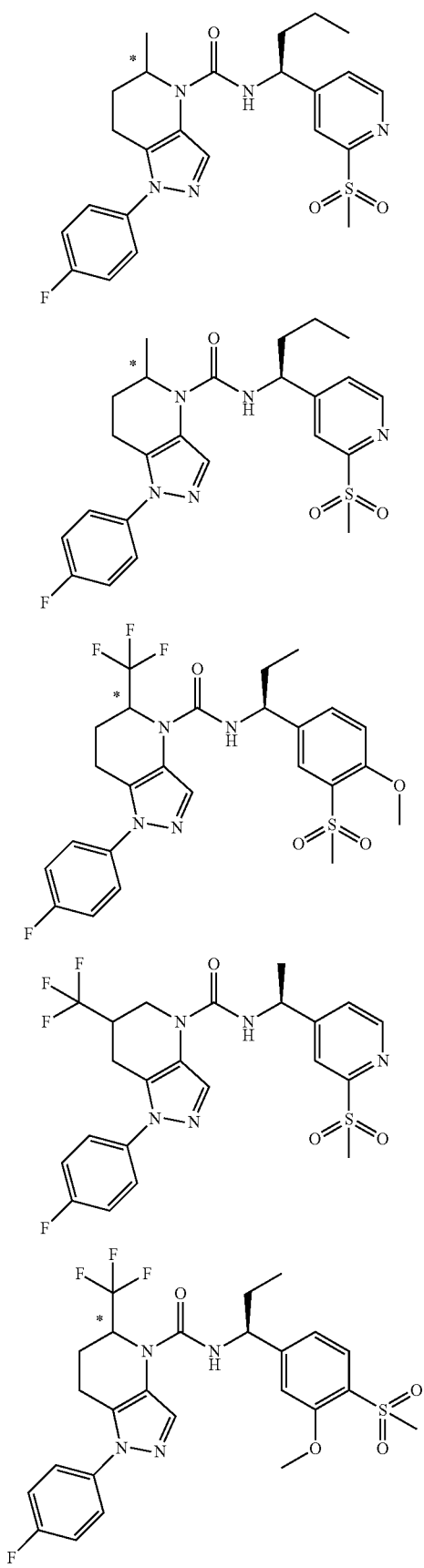
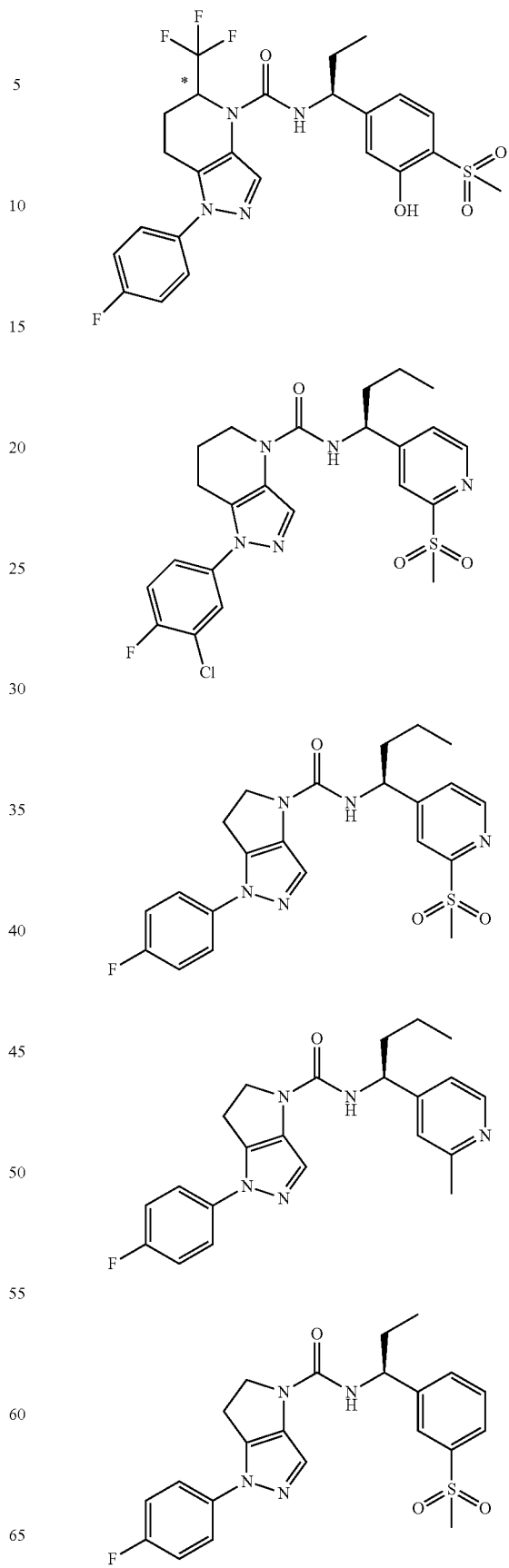

151
-continued
152
-continued
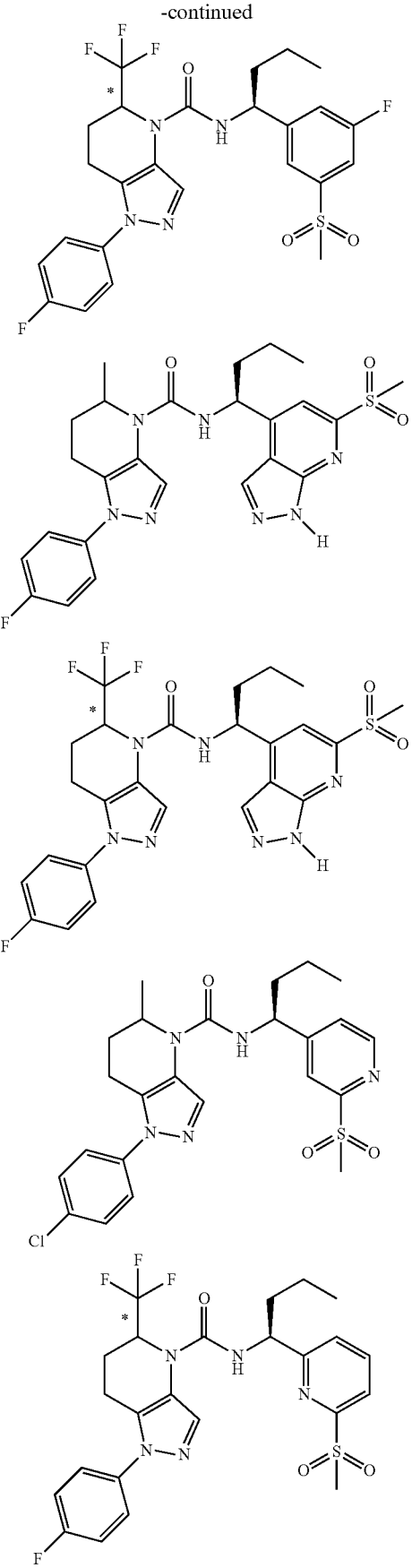
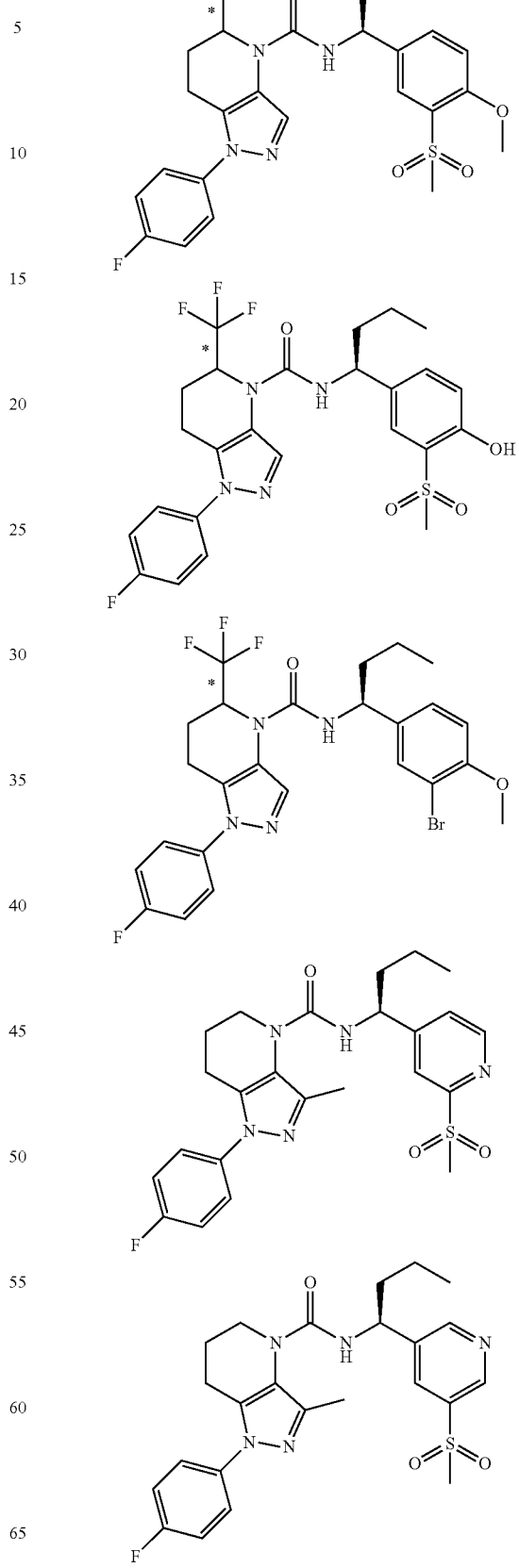

153
-continued
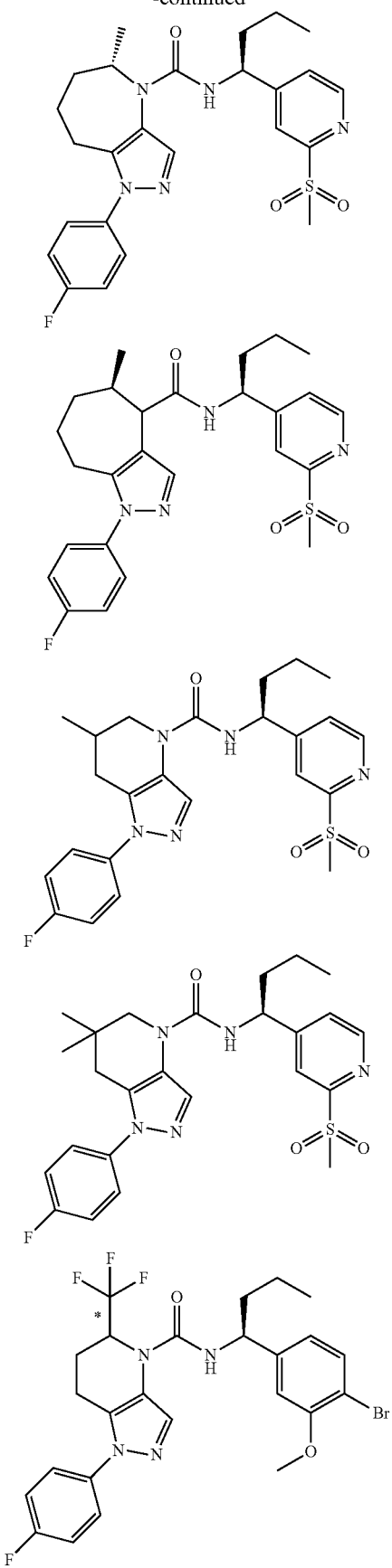
154
-continued
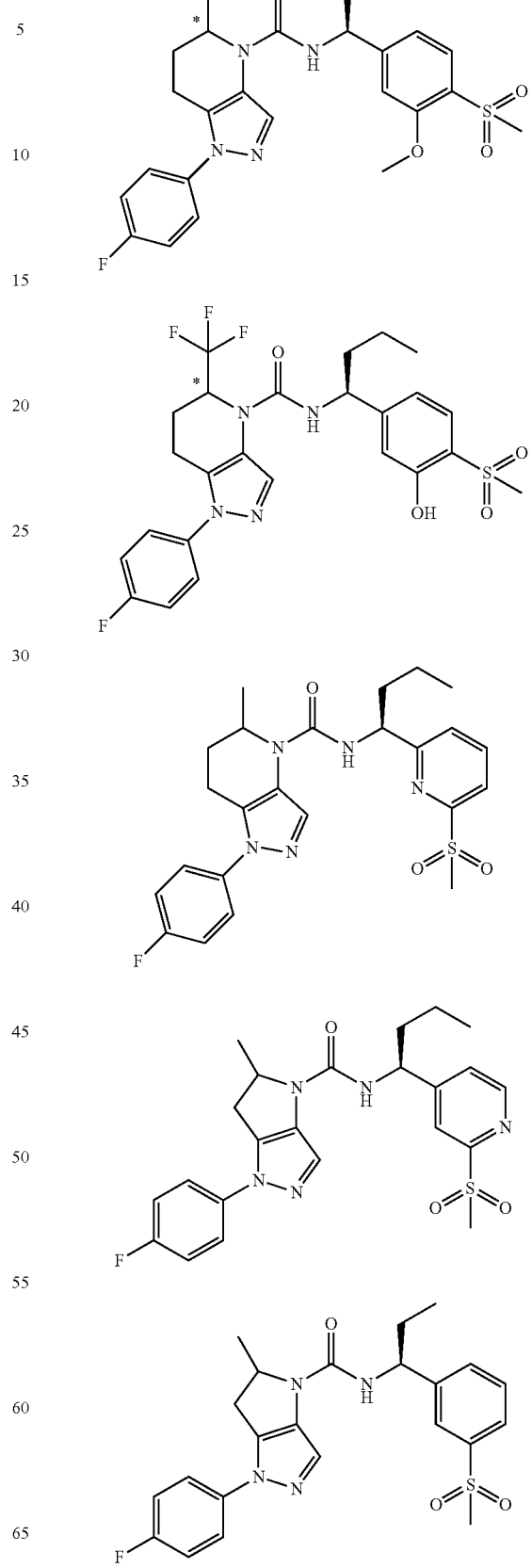

155
-continued
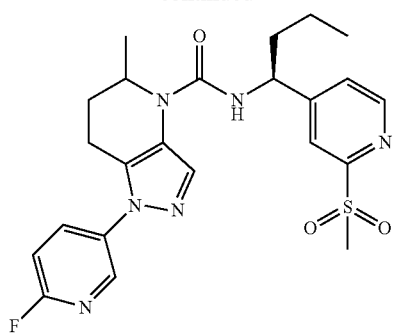
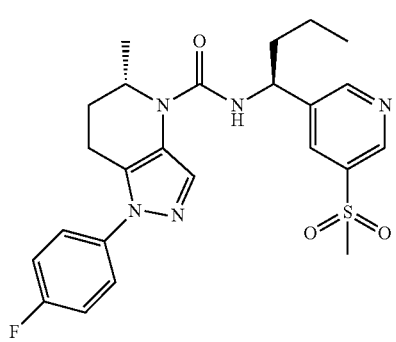
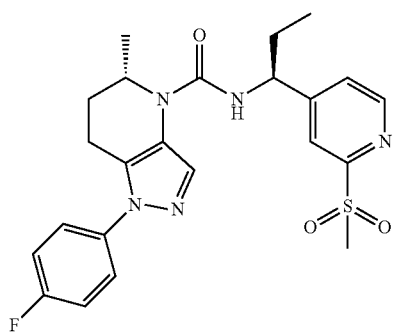
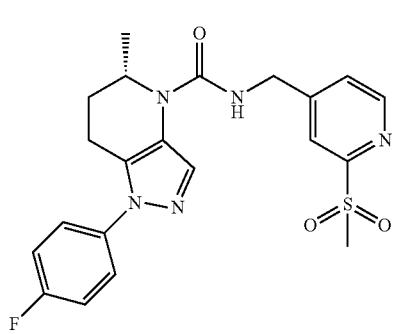
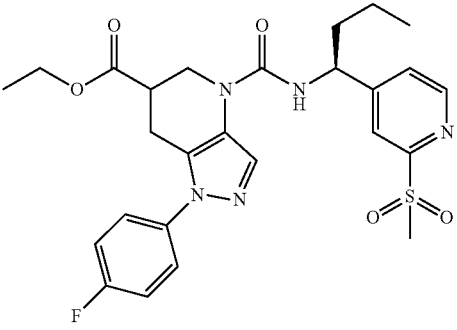
156
-continued
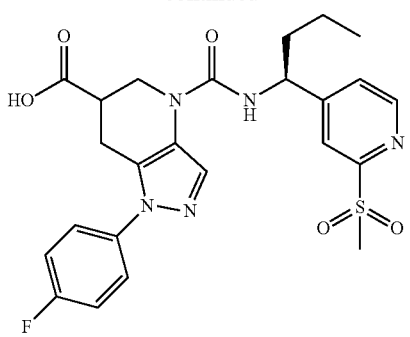
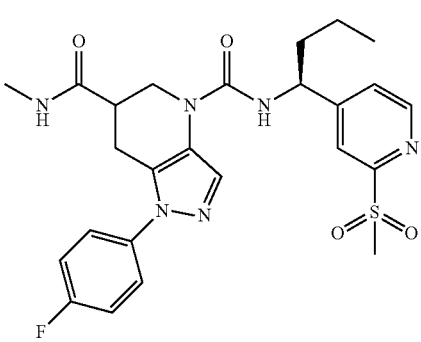
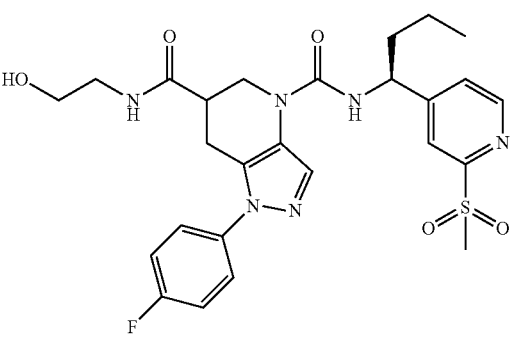
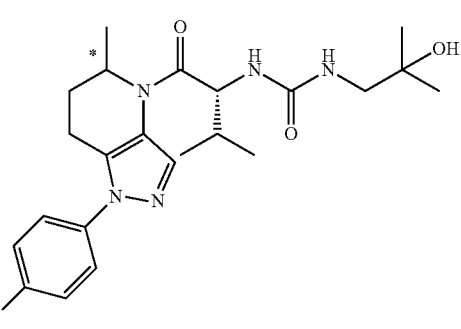
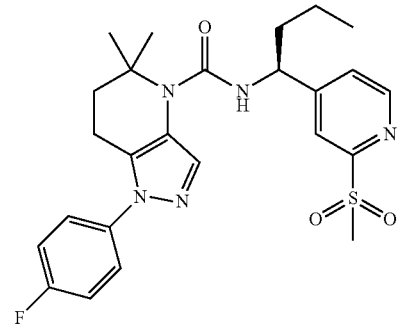

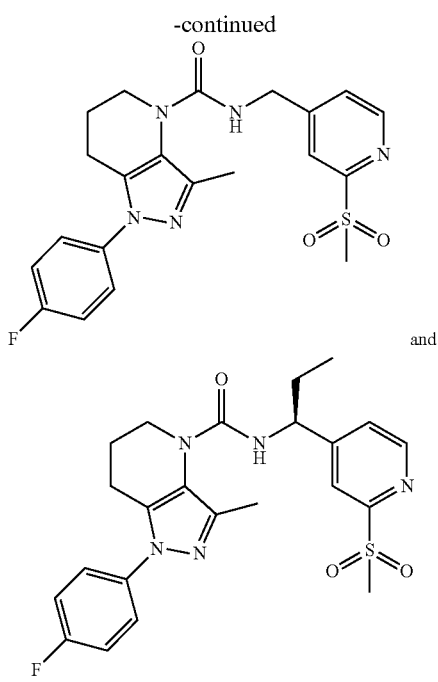

or a pharmaceutically acceptable salt thereof.

13. A pharmaceutical composition comprising a pharmaceutically effective amount of a compound according to claim 1 and one or more pharmaceutically carriers and/or adjuvants.

14. A method of treating chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease, Alzheimer's disease, asthma, chronic kidney disease, sepsis, autoimmune myocarditis and systemic lupus erythematosus, comprising administering to a patient a pharmaceutically effective amount of a compound according to claim 1.

15. The method according to claim 14 wherein the treatment is for rheumatoid arthritis and multiple sclerosis.

16. The method according to claim 14 wherein the treatment is for rheumatoid arthritis.

17. The method according to claim 15 wherein the treatment is for multiple sclerosis.

* * * * *